United States Patent
Goodnow, Jr. et al.

(10) Patent No.: US 9,447,035 B2
(45) Date of Patent: Sep. 20, 2016

(54) INTEGRIN ANTAGONIST CONJUGATES FOR TARGETED DELIVERY TO CELLS EXPRESSING VLA-4

(71) Applicant: Hoffmann-La Roche Inc., Nutley, NJ (US)

(72) Inventors: Robert Alan Goodnow, Jr., Gillette, NJ (US); Matthew Michael Hamilton, Hackettstown, NJ (US); Achyutharao Sidduri, Livingston, NJ (US)

(73) Assignee: Hoffmann-La Roche Inc., Nutley, NJ (US)

( * ) Notice: Subject to any disclaimer, the term of this patent is extended or adjusted under 35 U.S.C. 154(b) by 0 days.

(21) Appl. No.: 14/373,704

(22) PCT Filed: Jan. 24, 2013

(86) PCT No.: PCT/EP2013/051275
§ 371 (c)(1),
(2) Date: Jul. 22, 2014

(87) PCT Pub. No.: WO2013/110680
PCT Pub. Date: Aug. 1, 2013

(65) Prior Publication Data
US 2015/0031715 A1 Jan. 29, 2015

Related U.S. Application Data

(60) Provisional application No. 61/591,295, filed on Jan. 27, 2012, provisional application No. 61/670,295, filed on Jul. 11, 2012.

(51) Int. Cl.
| | |
|---|---|
| *C07D 207/452* | (2006.01) |
| *C07C 327/28* | (2006.01) |
| *C07D 403/12* | (2006.01) |
| *C07D 239/54* | (2006.01) |
| *A61K 49/00* | (2006.01) |

(52) U.S. Cl.
CPC ......... *C07C 327/28* (2013.01); *A61K 49/0043* (2013.01); *C07D 207/452* (2013.01); *C07D 239/54* (2013.01); *C07D 403/12* (2013.01); *C07C 2101/08* (2013.01)

(58) Field of Classification Search
CPC ............ C07C 327/28; C07D 207/452; C07D 239/54; C07D 403/12; C07D 2101/08; A61K 49/0043
See application file for complete search history.

(56) References Cited

U.S. PATENT DOCUMENTS

| | | | |
|---|---|---|---|
| 6,229,011 B1 * | 5/2001 | Chen | C07C 233/87 544/171 |
| 6,380,387 B1 * | 4/2002 | Sidduri | C07K 5/06165 540/601 |
| 6,388,084 B1 * | 5/2002 | Kaplan | C07D 213/64 546/291 |
| 6,916,933 B2 * | 7/2005 | Kaplan | C07D 213/64 544/131 |
| 2002/0133015 A1 * | 9/2002 | Kaplan | C07D 213/64 546/261 |
| 2004/0127706 A1 * | 7/2004 | Kaplan | C07D 213/64 544/60 |
| 2013/0079383 A1 * | 3/2013 | Bennett | C07C 237/40 514/44 A |
| 2013/0197059 A1 * | 8/2013 | Goodnow, Jr. | C07C 327/06 514/44 A |
| 2013/0197205 A1 * | 8/2013 | Chin | A61K 47/4823 536/20 |
| 2015/0031715 A1 * | 1/2015 | Goodnow, Jr. | A61K 49/0043 514/274 |
| 2015/0038523 A1 * | 2/2015 | Goodnow, Jr. | A61K 47/48061 514/275 |
| 2015/0306130 A1 * | 10/2015 | Chin | A61K 47/4823 514/55 |

FOREIGN PATENT DOCUMENTS

| | | | | |
|---|---|---|---|---|
| CH | WO 9910313 A1 * | 3/1999 | | C07C 233/87 |
| CH | WO 0142225 A2 * | 6/2001 | | C07D 239/54 |
| WO | WO 2005112919 A2 * | 12/2005 | | A61K 31/403 |

OTHER PUBLICATIONS

J. Luo et al., 36 Cell, 823-837 (2009).*
T. Soussi 60 Cancer Research, 1777-1788 (2000).*
P. Lissoni et al, 7 Cancer Research, 397-401 (2009).*
National Cancer Institute (http://www.cancer.gov/) (Downloaded May 29, 2014).*
F. Bunz, Principles of Cancer Genetics 1-47, 1 (2008).*
P.K. Kuppen et al., 115 Histochemistry and Cell Biology, 67-72 (2001).*
D. Scheinberg et al., Management of Acute Leukemias, in 2 Cancer Principles & Practice of Oncology 2088, 2092 (V.T. DeVita, Jr. et al. eds., 7th ed., 2005).*
D. Druker et al., Chronic Myelogenous Leukema, in 2 Cancer Principles & Practice of Oncology 2121 (V.T. DeVita, Jr. et al. eds., 7th ed., 2005).*
S. O'Brien et al., Chronic Lymphoid Leukemias, in 2 Cancer Principles & Practice of Oncology 2133 (V.T. DeVita, Jr. et al. eds., 7th ed., 2005).*

(Continued)

*Primary Examiner* — Alexander R Pagano

(57) ABSTRACT

The invention relates to compounds of formula I: wherein R1, R2, and n are defined in the detailed description and claims. In particular, the present invention relates to the compounds of formula I for use in the manufacture and delivery of conjugated moieties such as small molecules, peptides, nucleic acids, fluorescent moieties, and polymers which are linked to VLA-4 integrin antagonists to target cells expressing VLA-4.

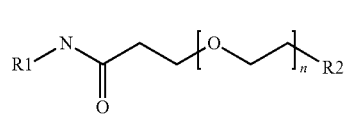

52 Claims, 11 Drawing Sheets

(56) References Cited

OTHER PUBLICATIONS

S. Faderi et al., Myelodysplastic Syndromes, in 2 Cancer Principles & Practice of Oncology 2133 (V.T. DeVita, Jr. et al. eds., 7th ed., 2005).*
H.A. Fine, Neoplasms of the Central Nervous System in, 2 Cancer Principles & Practice of Oncology 1834-1887 (V.T. DeVita, Jr. et al. eds., 5th ed., 2005).*
D. D'Ambrosio et al., 273 Journal of Immunological Methods 3-13 (2003).*
P.J. Koelink et al., 133 Pharmacology & Therapeutics, 1-18 (2012).*
E. R. Sutherland et al., 350 The New England Journal of Medicine, 2689-2697 (2004).*
S. Judge et al., 111 Pharmacology & Therapeutics, 224-259 (2006).*
V. Brinkmann et al., 9 Nature Reviews | Drug Discovery, 883-897 (2010).*
S. Fogarty et al., 1804 Biochimica et Biophysica Acta, 581-591 (2010).*
S Hariharan et al., 18 Annals of Oncology, 1400-1407 (2006).*
M. Klemke et al., 212 Journal of Cellular Physiology, 368-374 (2007).*
R.D. Carpenter et al., 52 Journal of Medicinal Chemistry, 14-19 (2009).*
B. Garmy-Susini et al., 70 Cancer Research, 3042-3051 (2010).*
M.C. Schmid et al., 71 Cancer Research, 6965-6975 (2011).*
N.J. Kenyon et al., 603 European Journal of Pharmacology 138-146 (2009).*
H. Yusuf-Makagiansar et al., 22 Medicinal Research Reviews, 146-167 (2002).*
H. Okigami et al., 559 European Journal of Pharmacology, 202-209 (2007).*
C.C. Feral et al., 57 Diabetes, 1842-1851 (2008).*
Z. Wang et al., 19 Drug Discovery Today, 145-150 (2014).*
U.K. Marelli et al., 3 Frontiers in Oncology, 1-12 (2013).*
R.D. Prasasya et al., 21 Seminars in Cancer Biology, 200-206 (2011).*
Kinase Inhibitors, Methods in Molecular Biology (B. Kuster ed., 2012).*
T.A. Denison et al., Heterogeneity of Cancers and Its Implication for Targeted Drug Delivery in, Cancer Targeted Drug Delivery an Elusive Dream, 337-362 (Y.H. Bae et al., eds., 2013).*
Steffen et al., 145 American Journal of Pathology, 189-201, 194 (1994).*

* cited by examiner

Table 1

Summaries of the composition of 5'-derivatized siRNA single and double strands

| Duplex-ID | Sense-ID | Sequence 5'-->3' | Antisense-ID | Sequence 5'-->3' |
|---|---|---|---|---|
| Duplex-1 | Sense-1 | GGAuGAAGuGGAGAuuAGudTsdT (SEQ ID NO.1) | Antisense-1 | ACuAAUCUCcACUUcAUCCdTsdT (SEQ ID NO 2) |
| Duplex-4 | Sense-4 | VLA-4 Ligand Reagent 8-(SC6)GGAuGAAGuGGAGAuuAGudTsdT | Antisense-1 | ACuAAUCUCcACUUcACUUcAUCCdTsdT |
| Duplex-5 | Sense-5 | VLA-4 Ligand Reagent 3-(SC6)GGAuGAAGuGGAGAuuAGudTsdT | Antisense-1 | ACuAAUCUCcACUUcAUCCdTsdT |
| Duplex-6 | Sense-6 | VLA-4 Ligand Reagent 1-(SC6)GGAuGAAGuGGAGAuuAGudTsdT | Antisense-1 | ACuAAUCUCcACUUcAUCCdTsdT |
| Duplex-7 | Sense-7 | VLA-4 Ligand Reagent 2-(SC6)GGAuGAAGuGGAGAuuAGudTsdT | Antisense-1 | ACuAAUCUCcACUUcAUCCdTsdT |
| Duplex-11 | Sense-11 | VLA-4 Ligand Reagent 11-(SC6)GGAuGAAGuGGAGAuuAGudTsdT | Antisense-1 | ACuAAUCUCcACUUcAUCCdTsdT |
| Duplex-12 | Sense-12 | VLA-4 Ligand Reagent 12-(SC6)GGAuGAAGuGGAGAuuAGudTsdT | Antisense-1 | ACuAAUCUCcACUUcAUCCdTsdT |
| Duplex-13 | Sense-13 | VLA-4 Ligand Reagent 9-(SC6)GGAuGAAGuGGAGAuuAGudTsdT | Antisense-1 | ACuAAUCUCcACUUcAUCCdTsdT |
| Duplex-14 | Sense-14 | VLA-4 Ligand Reagent 10-(SC6)GGAuGAAGuGGAGAuuAGudTsdT | Antisense-1 | ACuAAUCUCcACUUcAUCCdTsdT |

FIG. 1

Table 2

Analytical Data for small molecule siRNA conjugates

| Small Molecule | Target | Number | Sequence (5'--3') | Calc. Mass | Exp. Mass | IEX % FLP |
|---|---|---|---|---|---|---|
| VLA-4-1-PEG8-maleimide | Aha1 | Sense-6 | VLA-4 Ligand Reagent 2-(SC6)GGAuGAAGuGGAGAuuAGudTsdT | 8167.0 | 8167.0 | 91.4 |
| VLA-4-2-PEG4-maleimide | Aha1 | Sense-4 | VLA-4 Ligand Reagent 8-(SC6)GGAuGAAGuGGAGAuuAGudTsdT | 7978.71 | 7982.0 | 85.3 |
| VLA-4-1-PEG12-maleimide | Aha1 | Sense-5 | VLA-4 Ligand Reagent 3-(SC6)GGAuGAAGuGGAGAuuAGudTsdT | 8337.79 | 8342.3 | > 80 |
| VLA-4-1-PEG4-maleimide | Aha1 | Sense-6 | VLA-4 Ligand Reagent 1-(SC6)GGAuGAAGuGGAGAuuAGudTsdT | 7985.58 | 7990.0 | 71.9 |
| VLA-4-PEG4-maleimide | Aha1 | Sense-11 | VLA-4 Ligand Reagent 11-(SC6)GGAuGAAGuGGAGAuuAGudTsdT | 7982.18 | 7981,5 | 93.9 |
| VLA-4-PEG8-maleimide | Aha1 | Sense-12 | VLA-4 Ligand Reagent 12-(SC6)GGAuGAAGuGGAGAuuAGudTsdT | 8158.39 | 8158 | 87.0 |
| VLA-4-PEG4-maleimide | Aha1 | Sense-13 | VLA-4 Ligand Reagent 9-(SC6)GGAuGAAGuGGAGAuuAGudTsdT | 8059.14 | 8059 | 86.1 |
| VLA-4-PEG8-maleimide | Aha1 | Sense-14 | VLA-4 Ligand Reagent 10-(SC6)GGAuGAAGuGGAGAuuAGudTsdT | 8235.35 | 8234,8 | 93.7 |

FIG. 2

Table 3

Summary of siRNA sequences where in the 5'-antisense strand has been derivatized with Nu547

| Duplex-ID | Sense-ID | Sequence 5'—>3' | Antisense-ID | Sequence 5'—>3' |
|---|---|---|---|---|
| Duplex-24 | Sense-24 | VLA-4 Ligand Reagent 8-(SC6)GGAuGAAGuGGAGAuuAGudTsdT | Antisense-1 | (Nu547)ACuAAUCUCcACUUcAUCCdTsdT |
| Duplex-25 | Sense-25 | VLA-4 Ligand Reagent 3-(SC6)GGAuGAAGuGGAGAuuAGudTsdT | Antisense-1 | (Nu547)ACuAAUCUCcACUUcAUCCdTsdT |
| Duplex-26 | Sense-26 | VLA-4 Ligand Reagent 1-(SC6)GGAuGAAGuGGAGAuuAGudTsdT | Antisense-1 | (Nu547)ACuAAUCUCcACUUcAUCCdTsdT |
| Duplex-27 | Sense-27 | VLA-4 Ligand Reagent 2-(SC6)GGAuGAAGuGGAGAuuAGudTsdT | Antisense-1 | (Nu547)ACuAAUCUCcACUUcAUCCdTsdT |
| Duplex-31 | Sense-31 | VLA-4 Ligand Reagent 11-(SC6)GGAuGAAGuGGAGAuuAGudTsdT | Antisense-1 | (Nu547)ACuAAUCUCcACUUcAUCCdTsdT |
| Duplex-32 | Sense-32 | VLA-4 Ligand Reagent 12-(SC6)GGAuGAAGuGGAGAuuAGudTsdT | Antisense-1 | (Nu547)ACuAAUCUCcACUUcAUCCdTsdT |
| Duplex-33 | Sense-33 | VLA-4 Ligand Reagent 9-(SC6)GGAuGAAGuGGAGAuuAGudTsdT | Antisense-1 | (Nu547)ACuAAUCUCcACUUcAUCCdTsdT |
| Duplex-34 | Sense-34 | VLA-4 Ligand Reagent 10-(SC6)GGAuGAAGuGGAGAuuAGudTsdT | Antisense-1 | (Nu547)ACuAAUCUCcACUUcAUCCdTsdT |

FIG. 3

Table 4

Summary of small molecule-siRNA conjugate potencies in integrin antagonists assays and siRNA KD data

| Targeting Element | Configuration | | | siRNA derivative | Jurkat Cells/VCAM-1 Adhesion Assay (nM) | αVβ3 Adhesion Assay (nM) | LFA1 Adhesion Assay (nM) | AHA1 % KD |
| --- | --- | --- | --- | --- | --- | --- | --- | --- |
| | Small molecule Ligand Reagent | siRNA | Fluorochrome | | | | | |
| none | | AHA-1 | No | RD-03518 | > 200 | | | 98 |
| none | | AHA-1 | Nu547 | RD-05170 | > 200 | | | |
| VLA-4 Ligand 3-PEG 4 | VLA-4 Ligand Reagent 8 | AHA-1 | No | RD-04707 | 28 | | | 97 |
| VLA-4 Ligand 2-PEG 12 | VLA-4 Ligand Reagent 3 | AHA-1 | No | RD-04708 | 158 | | | 97 |
| VLA-4 Ligand 2-PEG 4 | VLA-4 Ligand Reagent 1 | AHA-1 | No | RD-04709 | 51 | | | 98 |
| VLA-4 Ligand 2-PEG 8 | VLA-4 Ligand Reagent 2 | AHA-1 | No | RD-04710 | 55 | | | 97 |
| VLA-4 Ligand 3-PEG 4 | VLA-4 Ligand Reagent 8 | AHA-1 | Nu547 | RD-04714 | 39 | | | 36 |
| VLA-4 Ligand 2-PEG 12 | VLA-4 Ligand Reagent 3 | AHA-1 | Nu547 | RD-04715 | 147 | | | 25 |
| VLA-4 Ligand 2-PEG 4 | VLA-4 Ligand Reagent 1 | AHA-1 | Nu547 | RD-04716 | 61 | | | 30 |
| VLA-4 Ligand 2-PEG 8 | VLA-4 Ligand Reagent 2 | AHA-1 | Nu547 | RD-04717 | 48 | | | 25 |
| VLA-4 Ligand 4-PEG 4 | VLA-4 Ligand Reagent 11 | AHA-1 | No | RD-04812 | 30 | | | |
| VLA-4 Ligand 4-PEG 8 | VLA-4 Ligand Reagent 12 | AHA-1 | No | RD-04813 | 24 | | | |
| VLA-4 Ligand 5-PEG 4 | VLA-4 Ligand Reagent 9 | AHA-1 | No | RD-04814 | 34 | | | |
| VLA-4 Ligand 5-PEG 8 | VLA-4 Ligand Reagent 10 | AHA-1 | No | RD-04815 | 44 | | | |
| VLA-4 Ligand 4-PEG 4 | VLA-4 Ligand Reagent 11 | AHA-1 | Nu547 | RD-04822 | 41 | | | |
| VLA-4 Ligand 4-PEG 8 | VLA-4 Ligand Reagent 12 | AHA-1 | Nu547 | RD-04823 | 23 | | | |
| VLA-4 Ligand 5-PEG 4 | VLA-4 Ligand Reagent 9 | AHA-1 | Nu547 | RD-04824 | 26 | | | |
| VLA-4 Ligand 5-PEG 8 | VLA-4 Ligand Reagent 10 | AHA-1 | Nu547 | RD-04825 | 31 | | | |
| VLA-4 small molecule | | | | 140 | 4 | | | |
| Negative assay reference | | FITC-22 | | | > 200 | | | |
| Negative assay reference | | FITC-23 | | | > 200 | | | |

FIG. 4

Table 5

Identity, characterization and binding potencies of FITC isomer labeled reagents

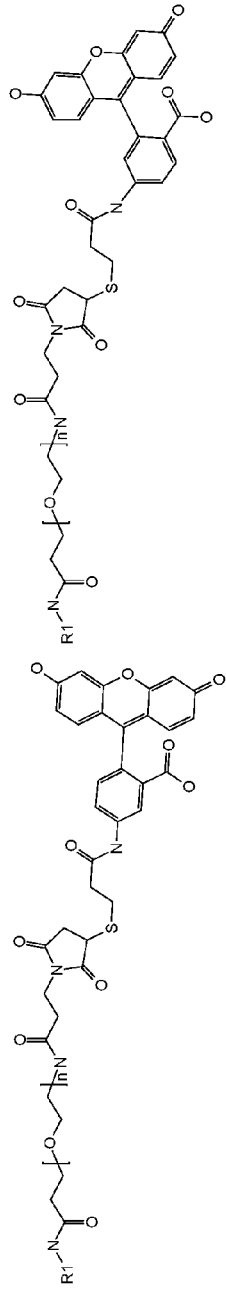

| Example | Targeting Element | Synthesis method: one pot or with corresponding targeting example | Jurkat Cells/VCAM-1 Adhesion Assay (IC50 nM) | αVβ3 Assay (IC50 nM) | LFA1 Adhesion Assay (IC50 nM) | Calc. Mass | Observed Mass |
|---|---|---|---|---|---|---|---|
| FITC-12 | VLA-4 Ligand 1-PEG8-FITC | VLA-4 Ligand Reagent 2 | 199 | | | 1502.47 | 1503.7 [M+H]+ |
| FITC-13 | VLA-4 Ligand 2-PEG4-FITC | VLA-4 Ligand Reagent 5 | 90 | | | 1433.16 | 1431.0 [M+H]+ |
| FITC-14 | VLA-4 Ligand 2 no linker: FITC amide | amide coupling of FITC carboxylate and VLA-4 ligand 2 | 15 | | | 956.0942 | 956.0937 (M+H)+ |
| FITC-15 | VLA-4 Ligand 5-PEG4-FITC | VLA-4 Ligand Reagent 9 | 175 | | | 1397.3 | 1398.2 [M+H]+ |
| FITC-16 | VLA-4 Ligand 5-PEG8-FITC | VLA-4 Ligand Reagent 10 | 178 | | | 1573.51 | 1573.6 [M+H]+ |
| FITC-22 | untargeted benzyl-PEG4-FITC | Method B (one pot) | 9,400 | | | 941.019 | 941.3269 (M+H)+ |
| FITC-23 | untargeted benzyl-PEG8-FITC | Method B (one pot) | >200 | | >10,000 | 1117.23 | 1117.4317 [M+H]+ |
| 142 | positive control | | | | 74 | | |
| 140 | positive control | | 4 | 2 | | | |
| 141 | positive control | | | | | | |

FIG. 5

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: siRNA targeting AHA1

<400> SEQUENCE: 1
ggaugaagug gagauuagut t                                        21

<210> SEQ ID NO 2
<211> LENGTH: 21
<212> TYPE: DNA
<213> ORGANISM: Artificial Sequence
<220> FEATURE:
<223> OTHER INFORMATION: siRNA targeting AHA1

<400> SEQUENCE: 2
acuaaucucc acuucaucct t                                        21
```

INTEGRIN ANTAGONIST CONJUGATES FOR TARGETED DELIVERY TO CELLS EXPRESSING VLA-4

This application is a National Stage Application of PCT/EP2013/051275 filed Jan. 24, 2013, which claims the benefit of U.S. Provisional Patent Application No. 61/591,295, filed Jan. 27, 2012 and U.S. Provisional Patent Application No. 61/670,666, filed Jul. 12, 2012. Each of these applications is hereby incorporated by reference herein in its entirety.

The present invention relates to the synthesis and reaction of potent and selective small molecule integrin antagonists containing appropriate linkers and functional groups for chemical reaction with other molecules which contain reactive nucleophiles such as thiols such that a covalent linkage is formed between a moiety to be conjugated and the targeting entity. The small molecule targeting antagonists bind to cognate receptor systems as VLA-4 antagonists to the VLA-4 dimer (as α4β1 antagonists to the Integrin α4β1 (Very Late Antigen-4 dimer). The covalently linked moiety includes small molecule therapeutics, polymers, peptides, and oligonucleotides. Included are 5'-thio-containing oligonucleotides for formation of 5'-thio-siRNA derivatives as a means to enable targeted delivery of said siRNAs. Such derivatized siRNAs in conjunction with appropriate transfection agents aid in the selective delivery of siRNAs to cells which express such integrin receptors, thereby preventing the expression of target genes through RNA interference (RNAi).

VLA-4 (Very Late Antigen-4, also called α4β1) is an integrin dimer. It is comprised of two subunits consisting of CD49d (alpha) and CD29 (beta). VLA-4 is expressed on leukocyte plasma membranes which bind to VCAM-1 on blood vessels (after activation by cytokines) helping the leukocytes adhere to vascular endothelium (contributing to atherosclerosis or other inflammatory diseases). Certain cancer cells may also express VLA-4 which bind to VCAM-1 adhering to the endothelium (increasing the risk of metastasis). Thus, compounds that bind to VLA-4 may block the interaction with VCAM-1 potentially treating or preventing diseases mediated by this interaction. Alternatively, compounds that bind to VLA-4 may be used in delivery formulations to deliver drugs, nucleic acids, or other therapeutic compounds to tissues or cells expressing VLA-4 for the treatment or prevention of disease.

RNA interference is a well-known process in which the translation of messenger RNA (mRNA) into protein is interfered with by the association or binding of complementary or partially complementary oligonucleotides such as small interfering RNA (siRNA), short hairpin RNA (shRNA), micro RNA (miRNA), or antisense oligonucleotides. siRNAs are double-stranded RNA molecules, usually ranging from 19-25 nucleotides in length that associate with a set of proteins in the cytoplasm known as RISC (RNA-induced silencing complex). RISC ultimately separates the double stranded siRNA allowing one strand to bind or associate with a complementary or partially complementary portion of an mRNA molecule after which the mRNA is destroyed by RISC or otherwise prevented from being translated—consequently suppressing the expression of the encoded protein or gene product.

One of the problems in using nucleic acids such as siRNA in therapeutic applications (especially for systemic administration in humans) has been in delivering the nucleic acids to: (1) particular target tissues or cell types and (2) to the cytoplasm of those cells (i.e., where the mRNA is present and translated into protein). Part of the delivery problem is based on the fact that nucleic acids are negatively charged and easily degraded (especially if unmodified), efficiently filtered by the kidney, and cannot be easily transported to the cytoplasm of the cells by themselves. Thus, a significant amount of research has focused on solving the delivery problem with various carriers and formulations including liposomes, micelles, peptides, polymers, conjugates and aptamers. See Ling et al, *Advances in Systemic siRNA Delivery*, Drugs Future 34(9): 721 (September 2009). Some of the more promising delivery vehicles have involved the use of lipidic systems including lipid nanoparticles. See Wu et al., *Lipidic Systems for In Vivo siRNA Delivery*, AAPS J. 11(4): 639-652 (December 2009); International Patent Application Publication No. WO 2010/042877 by Hope et al ("Improved Amino Lipids And Methods For the Delivery of Nucleic Acids"). However, a need remains for further improved targeting of siRNA; as well as other substances such as small molecules, peptides, other nucleic acids, fluorescent moieties, and polymers to particular target cells and to the cytoplasm of such cells.

The invention relates to compounds of formula I:

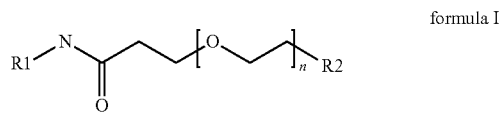

formula I wherein R1, R2, and n are defined in the detailed description and claims. In particular, the present invention relates to the compounds of formula I for the improved delivery of conjugated moieties such as small molecules, peptides, nucleic acids, fluorescent moieties, and polymers to target cells expressing the integrin α4β1 (Very Late Antigen-4) dimer for various therapeutic and other applications. The present invention also relates to methods of manufacturing and using such compounds.

BRIEF DESCRIPTION OF THE DRAWINGS

FIG. 1 is Table 1 showing the composition of particular 5'-derivatized siRNA single and double strands.

FIG. 2 is Table 2 showing analytical data for small molecule siRNA conjugates.

FIG. 3 is Table 3 showing the siRNA sequences wherein the 5'-antisense strand has been derivatized with Nu547.

FIG. 4 is Table 4 showing small molecule-siRNA conjugate potencies in integrin antagonists assays and siRNA KD data.

FIG. 5 is Table 5 showing the identity, characterization and binding potencies of FITC isomer labeled reagents.

Figure 6:
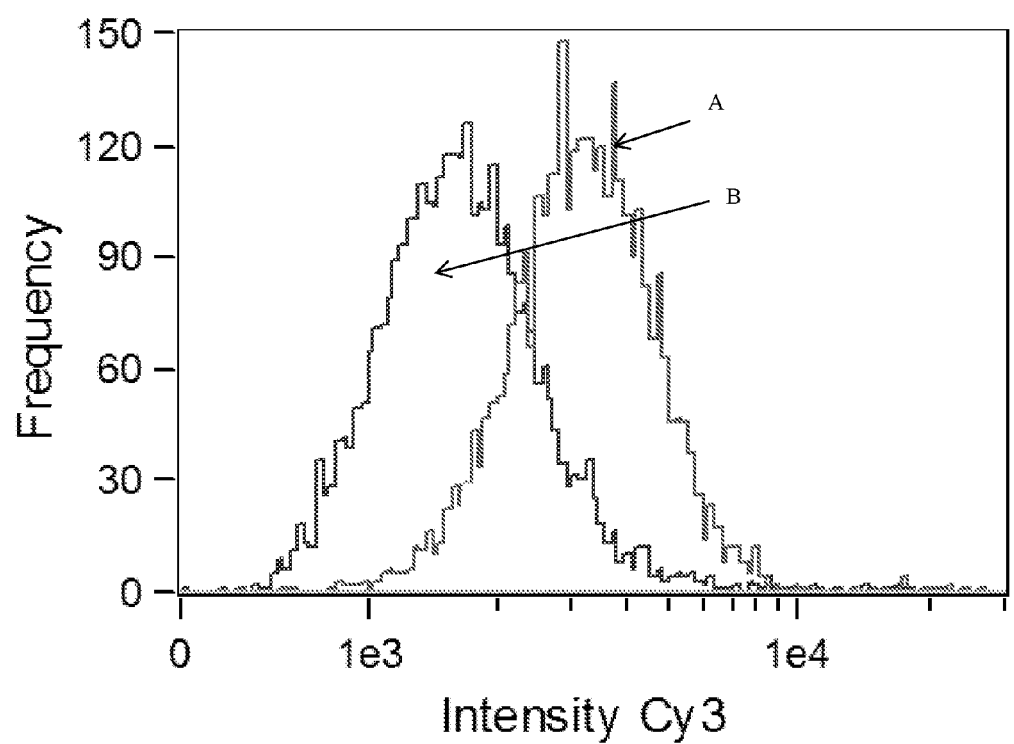
FIG. 6 shows a histogram ("B": Duplex-27 500 nM and Example 140 10 μM; "A": Duplex-27).
Figure 7:
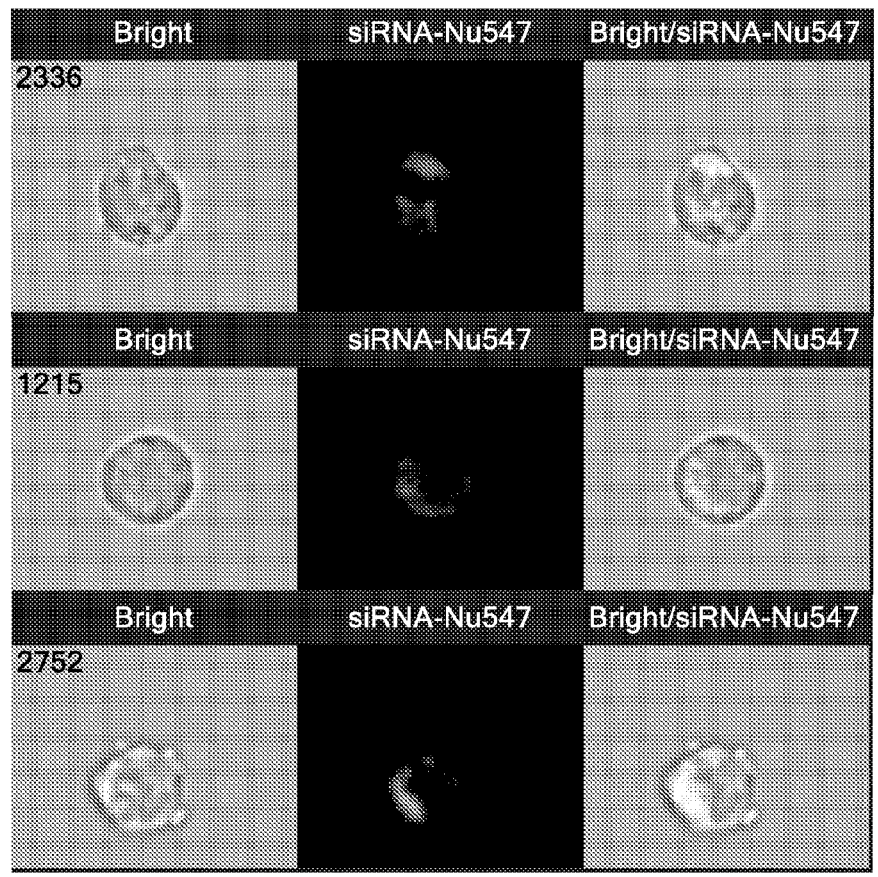
FIG. 7 shows representative siRNA uptake image (Duplex-27 (500 nM).
Figure 8:
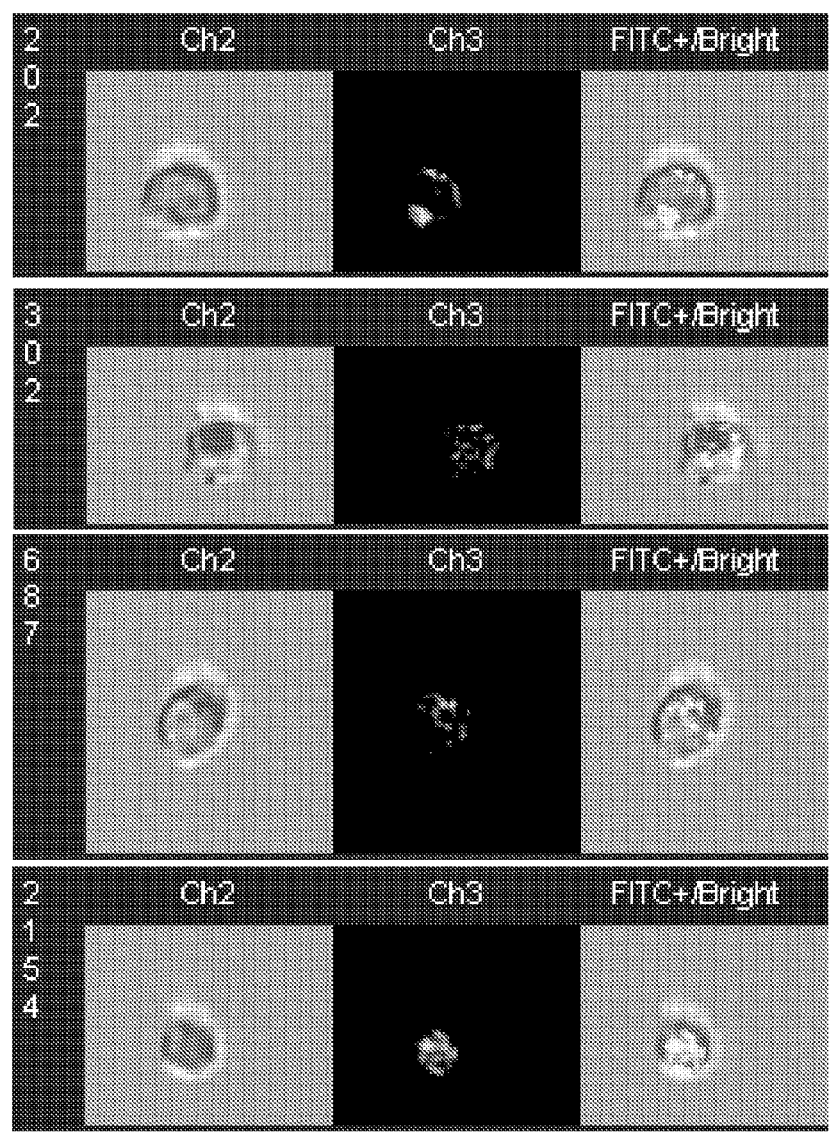
FIG. 8 shows images of Jurkat cells with FITC conjugated with Example FITC-5 (LFA-1 antagonist-labeled FITC) at 10 μM.
Figure 9:
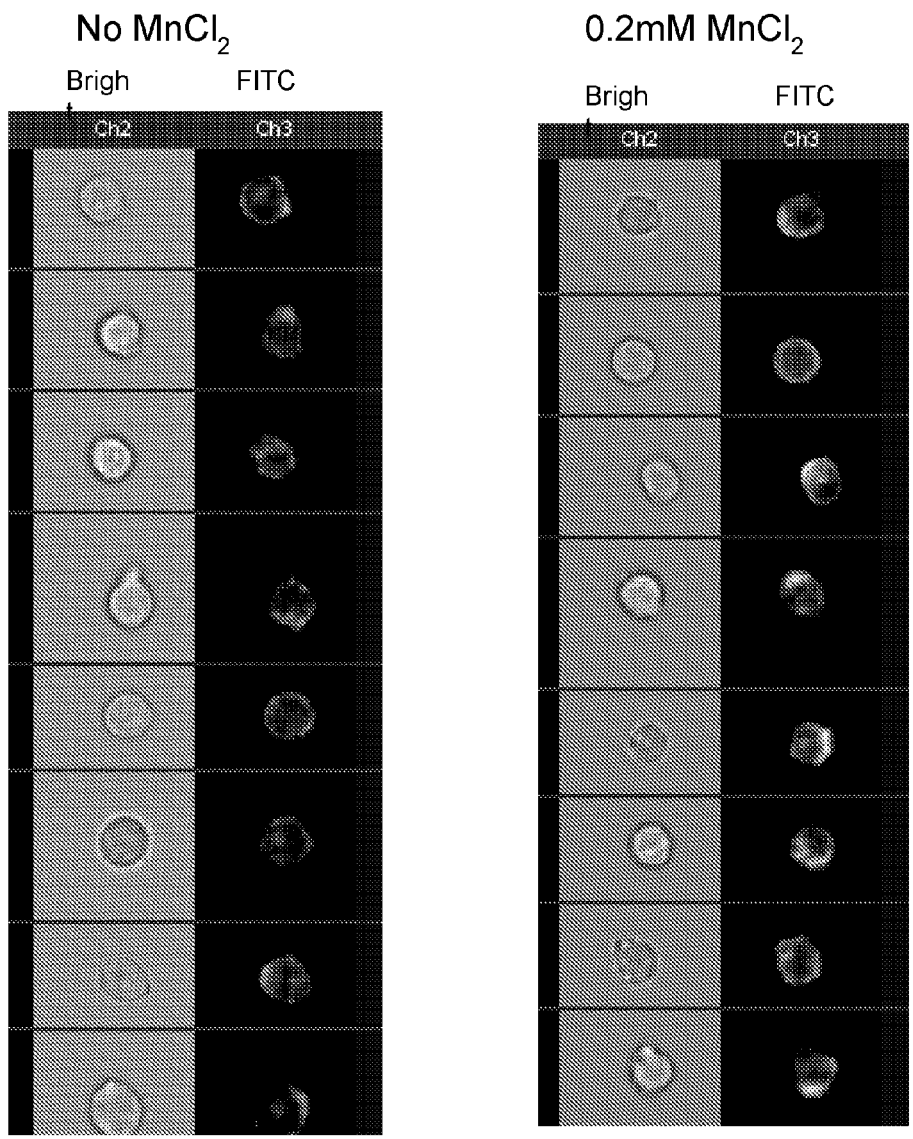
FIG. 9 shows images of Jurkat cells with FITC conjugated with Example FITC-14 (VLA-4 antagonist-labeled FITC) at 10 μM. The histogram indicates a shift in presence of the siRNA duplex with a VLA-4 targeting element. In the presence of VLA-4 antagonist example 140, this shift is oblated.

Unless otherwise indicated, the following specific terms and phrases used in the description and claims are defined as follows:

The term "moiety" refers to an atom or group of chemically bonded atoms that is attached to another atom or molecule by one or more chemical bonds thereby forming part of a molecule. For example, the variables R1 and R2 of formula I refer to moieties that are attached to the structure shown in formula I by a covalent bond where indicated.

The term "conjugated moiety" refers to moiety which is a therapeutic or useful compound, peptide, polymer, small molecule, fluorescent moiety, oligonucleotide or nucleic acid. Examples include drugs, therapeutic peptides, antisense oligonucleotides, siRNA, and fluorescein isothiocyanate (FITC).

Unless otherwise indicated, the term "hydrogen" or "hydro" refers to the moiety of a hydrogen atom (—H) and not $H_2$.

The term "halogen" refers to a moiety of fluoro, chloro, bromo or iodo.

The term "alkyl" refers to an aliphatic straight-chain or branched-chain saturated hydrocarbon moiety having 1 to 25 carbon atoms.

The term "TFA" refers to trifluoroacetic acid.

Unless otherwise indicated, the term "a compound of the formula" or "a compound of formula" or "compounds of the formula" or "compounds of formula" means any compound selected from the genus of compounds as defined by the formula (including any pharmaceutically acceptable salt or ester of any such compound if not otherwise noted).

The term "pharmaceutically acceptable salts" refers to those salts which retain the biological effectiveness and properties of the free bases or free acids, which are not biologically or otherwise undesirable. Salts may be formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxalic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, N-acetylcystein and the like. In addition, salts may be prepared by the addition of an inorganic base or an organic base to the free acid. Salts derived from an inorganic base include, but are not limited to, the sodium, potassium, lithium, ammonium, calcium, and magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polyamine resins and the like. Depending on the substitution patterns, the compounds of the present invention may also exist as zwitterions.

The compounds of the present invention can be present in the form of pharmaceutically acceptable salts. The compounds of the present invention can also be present in the form of pharmaceutically acceptable esters (i.e., the methyl and ethyl esters of the acids of formula I to be used as prodrugs). The compounds of the present invention can also be solvated, i.e. hydrated. The solvation can be affected in the course of the manufacturing process or can take place i.e. as a consequence of hygroscopic properties of an initially anhydrous compound of formula I (hydration).

Compounds that have the same molecular formula but differ in the nature or sequence of bonding of their atoms or the arrangement of their atoms in space are termed "isomers." Isomers that differ in the arrangement of their atoms in space are termed "stereoisomers." Diastereomers are stereoisomers with opposite configuration at one or more chiral centers which are not enantiomers. Stereoisomers bearing one or more asymmetric centers that are non-superimposable mirror images of each other are termed "enantiomers." When a compound has an asymmetric center, for example, if a carbon atom is bonded to four different groups, a pair of enantiomers is possible. An enantiomer can be characterized by the absolute configuration of its asymmetric center or centers and is described by the R- and S-sequencing rules of Cahn, Ingold and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture".

The term "a therapeutically effective amount" means an amount of a compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention is contemplated. Supplementary active compounds can also be incorporated into the compositions.

In detail, the present invention relates to the compounds of formula I:

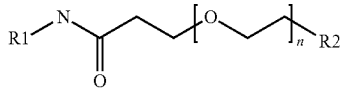

Formula I or pharmaceutically acceptable salts or esters thereof; wherein n is 1-24 and wherein:

R1 is selected from the group consisting of:
(1) a compound of the formula:

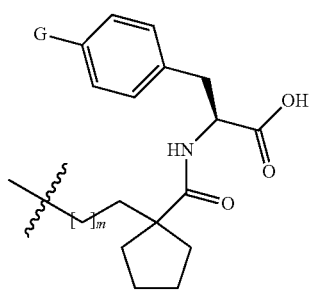

wherein m is 0-3 and G is selected from the group consisting of:

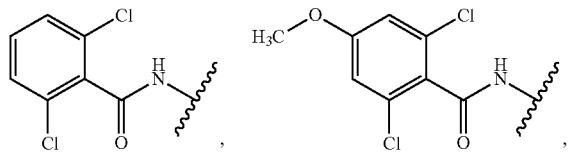

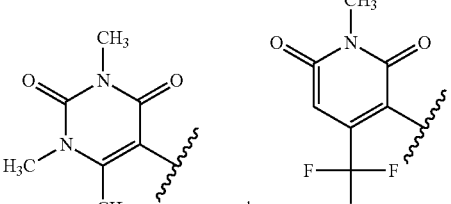

, and (3) a compound of the formula:

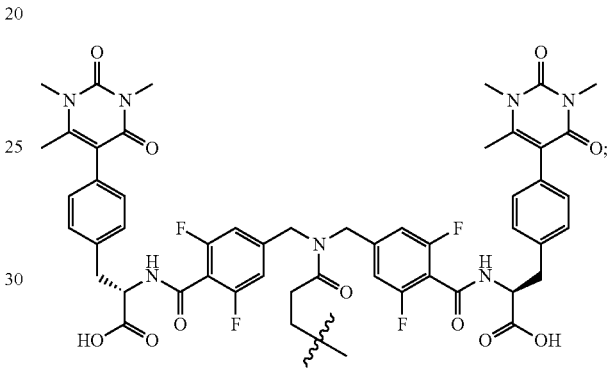

R2 is selected from the group consisting of:
(1) a compound of the formula:

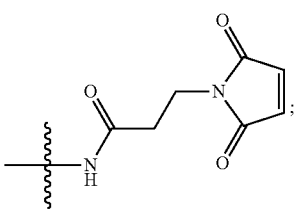 [SMILES: *NC(=O)CCN1C(=O)C=CC1=O]

(2) a compound of the formula:

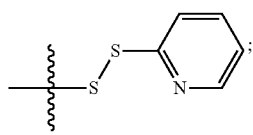 [SMILES: *SSc1ccccn1]

(3) a compound of the formula:

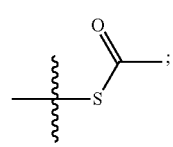

and

, and (2) a compound of the formula:

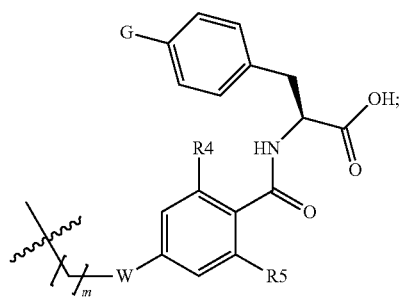

wherein m is 0-3, R4 and R5 are independently hydrogen or halogen, W is O or CH$_2$, and G is selected from the group consisting of:

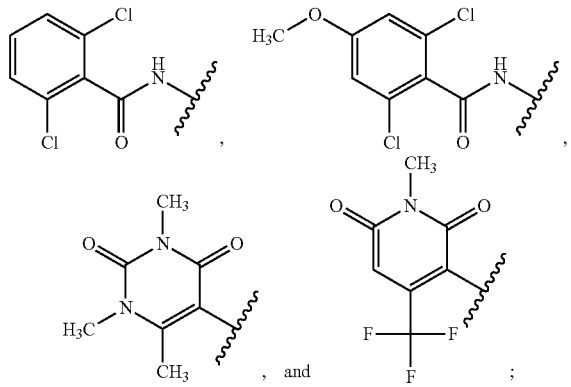

(4) a compound of the formula:

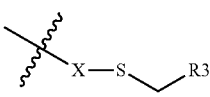

wherein R3 is a conjugated moiety and X represents either sulfur or a compound of the formula:

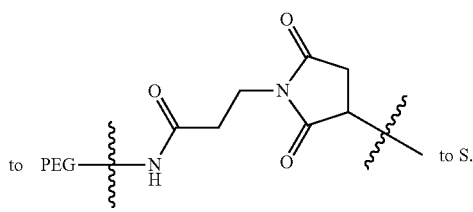

As used in the above structures, the symbol ⁂ is used to indicate where the structure or moiety is attached to the base molecule by a covalent bond. In addition, the phrase "to PEG" or "to S" or similar language used in combination with the above symbol, indicates where or how the structure or moiety is attached to the base molecule if there a multiple attachment points. For example, if R2 is a compound of the formula:

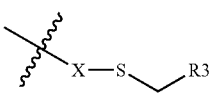

wherein X is a compound of the formula:

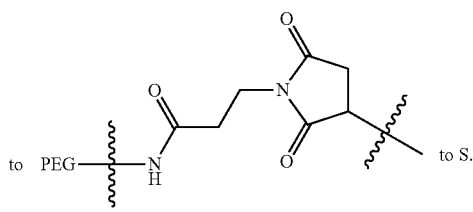

then the structure based upon formula I would be:

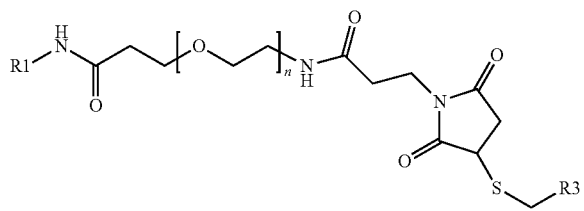

wherein R1, R3, and n are as defined in formula I.

The present invention also relates to methods of manufacturing and using the compounds of formula I as well as pharmaceutical compositions containing such compounds. The compounds of formula I are useful in improving the delivery of small molecules, proteins, nucleic acids, polymers, fluorescent markers, and other substances to target cells expressing VLA-4 receptors. In particular embodiments, the present invention relates to compositions and formulations containing the compounds of formula I which are useful in delivering siRNA to the cytoplasm of target cells expressing VLA-4 receptors to inhibit the expression of certain target proteins through RNA interference.

In more particular embodiments, the invention relates to the use of the compounds of formula I for formulation to facilitate the delivery of nucleic acids such as siRNA to tumor cells and other cell types expressing VLA-4 receptors. Furthermore, the use of the compounds of formula I to synthesize delivery formulations to treat inflammation and proliferative disorders, like cancers, is part of the invention.

R1 represents small molecule integrin antagonists which target the compounds of formula I to VLA-4 integrin receptor complexes, thereby facilitating their delivery to cells that express such receptors.

In particular embodiments, the small molecule integrin antagonist targeting moieties of R1 are attached at a position such that the affinity of binding of the small molecule to the integrin receptor is not substantially reduced relative to the free small molecule integrin antagonist. The R1 moieties of formula I target the VLA-4 (Integrin α4β1 or the Very Late Antigen-4) dimer.

In particular embodiments, R1 is a VLA-4 targeting moiety of the formula:

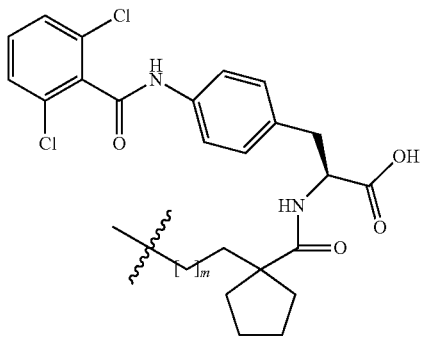

or a pharmaceutically acceptable salt or ester thereof, wherein m is 0-3.

In other particular embodiments, R1 is a VLA-4 targeting moiety of the formula:

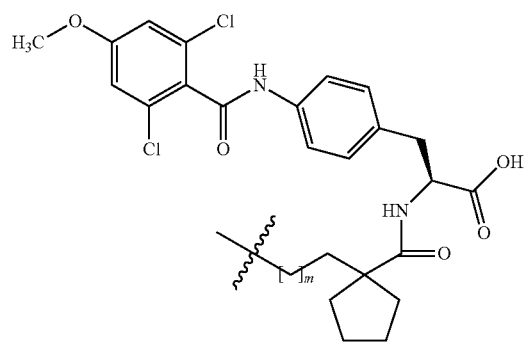

or a pharmaceutically acceptable salt or ester thereof, wherein m is 0-3.

In other particular embodiments, R1 is a VLA-4 targeting moiety of the formula:

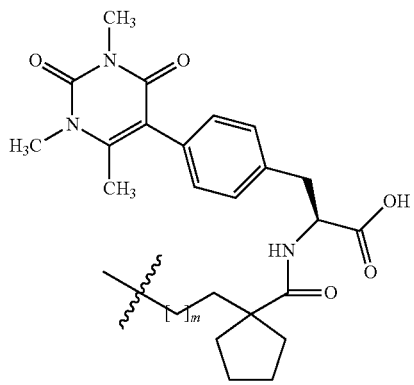

or a pharmaceutically acceptable salt or ester thereof, wherein m is 0-3.

In other particular embodiments, R1 is a VLA-4 targeting moiety of the formula:

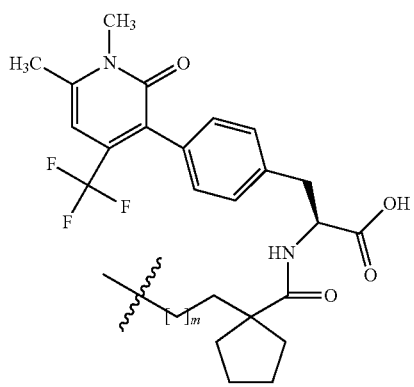

or a pharmaceutically acceptable salt or ester thereof, wherein m is 0-3.

In other embodiments, R1 is a VLA-4 targeting moiety of the formula:

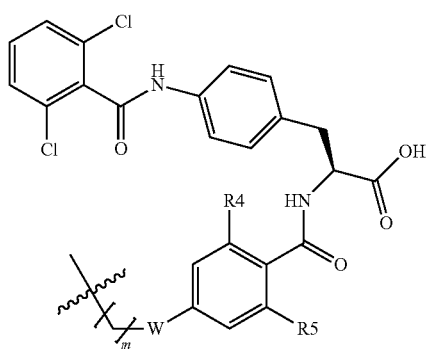

or a pharmaceutically acceptable salt or ester thereof, wherein m is 0-3, R4 and R5 are hydrogen or halogen, and W is O or $CH_2$.

In other particular embodiments, R1 is a VLA-4 targeting moiety of the formula:

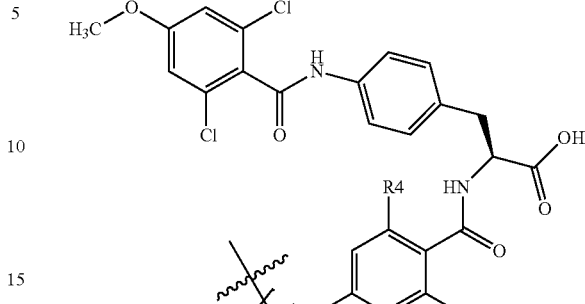

or a pharmaceutically acceptable salt or ester thereof, wherein m is 0-3, R4 and R5 are hydrogen or halogen, and W is O or $CH_2$.

In other particular embodiments, R1 is a VLA-4 targeting moiety of the formula:

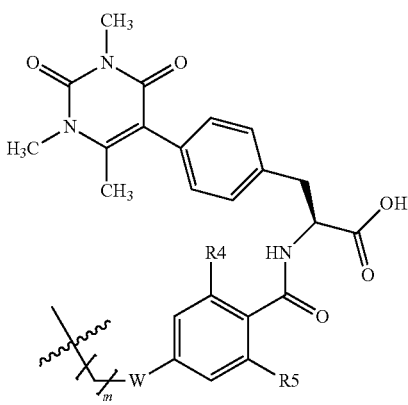

or a pharmaceutically acceptable salt or ester thereof, wherein m is 0-3, R4 and R5 are hydrogen or halogen, and W is O or $CH_2$.

In other particular embodiments, R1 is a VLA-4 targeting moiety of the formula:

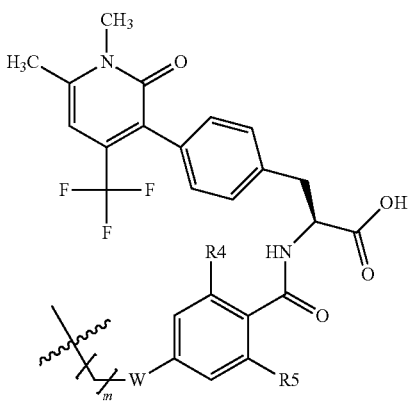

or a pharmaceutically acceptable salt or ester thereof,
wherein m is 0-3, R4 and R5 are hydrogen or halogen,
and W is O or CH$_2$.

In other particular embodiments, R1 is a VLA-4 targeting moiety of the formula:

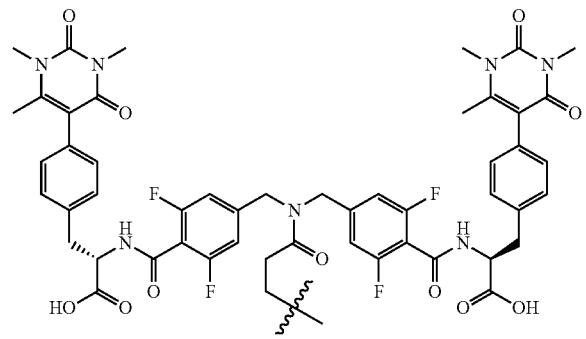 [SMILES: *CCC(=O)N(Cc1cc(F)c(C(=O)N[C@@H](Cc2ccc(-c3c(C)n(C)c(=O)n(C)c3=O)cc2)C(=O)O)c(F)c1)Cc1cc(F)c(C(=O)N[C@@H](Cc2ccc(-c3c(C)n(C)c(=O)n(C)c3=O)cc2)C(=O)O)c(F)c1]

or a pharmaceutically acceptable salt or ester thereof.

R2 may represent reactive moieties which can form covalent linkages with therapeutic or other useful compounds or conjugated moieties having strong nucleophiles such as thiol-containing molecules. Examples of such reactive moieties include moieties selected from the group consisting of:

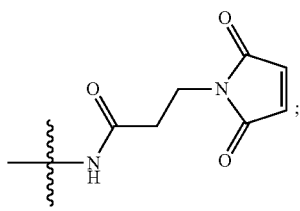

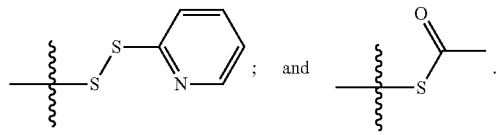

Alternatively, R2 may represent a moiety which is already attached to a conjugated moiety such as a therapeutic or other useful compound, protein, or oligonucleotide (R3). More specifically, R2 may represent a moiety of the formula:

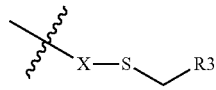

wherein R3 is a conjugated moiety and X represents either sulfur or a compound of the formula:

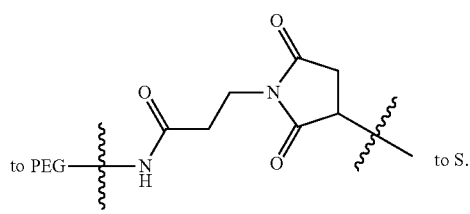

In particular embodiments, R3 represents an oligonucleotide. In more specific embodiments, R3 represents the 5'-end of the sense strand of an RNA molecule which may exist as a single strand or in a duplex such as a siRNA molecule. Such siRNA molecules, also known as RNAi agents, inhibit the expression of a target gene in a cell. In specific embodiments, R3 is a siRNA molecule that consists essentially of an oligoribonucleotide strand of between 15 and 30 nucleotides in length, wherein the 5' terminus of the sense oligoribonucleotide strand is coupled to R2 as shown in the above structures and is complementary to at least one portion of an mRNA corresponding to the target gene. In other embodiments, R3 is an oligonucleotide of DNA attached at its 5'-end. Such derivatized DNA may exist as a single strand or as one strand hybridized with a complementary strand of another oligonucleotide. The oligonucleotide strands can be either unmodified or modified for metabolic stability. Such modifications include, but are not limited to, substitutions at specific positions on the phosphate (e.g., phosphorothioate) and 2'-hydroxy (e.g., 2'-O-methyl and 2'-fluoro).

In particular embodiments, R2 of formula I represents —X—S—CH$_2$—R3 wherein R3 includes a sense strand of RNA as shown below in formula 5 (based on formula I):

5

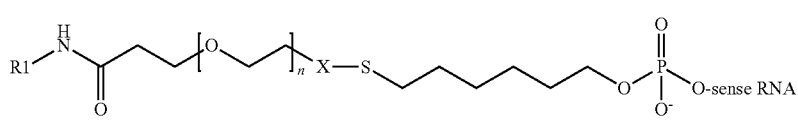

wherein R1, n, and X are as defined in formula I.

In other particular embodiments, the sense strand may be bound to an antisense strand.

In other specific embodiments, R2 represents —X—S—CH$_2$—R3 wherein R3 represents a small molecule or protein, thereby forming a covalently linked, specifically targeted entity of formula I.

In more specific embodiments, R2 represents —X—S—CH$_2$—R3 wherein R3 represents a therapeutic small molecule or protein.

In other specific embodiments, R2 represents —X—S—CH$_2$—R3 wherein R3 represents a fluorescent moiety useful for the visualization of these integrin receptor bindings using cellular microscopy techniques.

In other specific embodiments, R2 represents —X—S—CH$_2$—R3 wherein R3 represents a polymer having primary, reactive sulfides. More specifically, R3 may represent a cationic polymer useful for the complexation and delivery of siRNA to cell surfaces and the cytoplastic domains of cells.

In more particular embodiments, the present invention is directed to compounds of formula I wherein R3 is one of the structural isomers of fluorescein isothiocyanate (FITC) shown below:

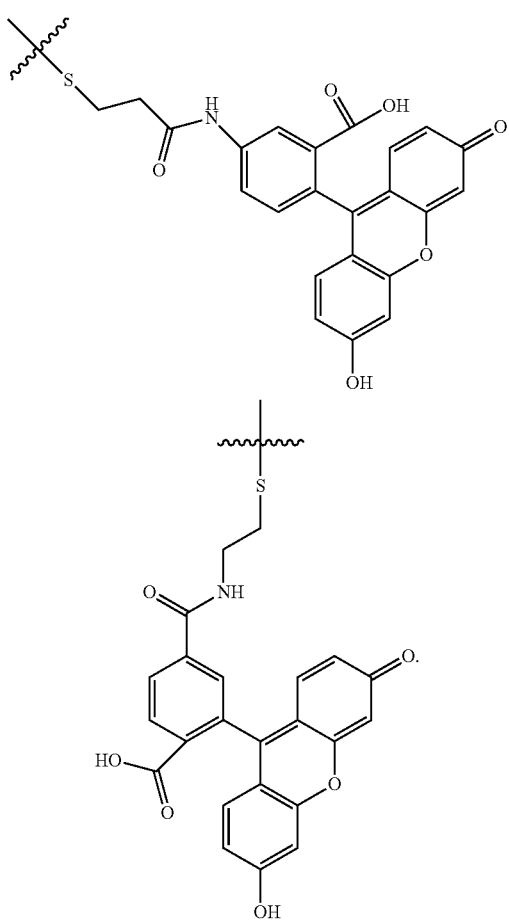 [SMILES: *SCCC(=O)Nc1ccc(-c2c3ccc(=O)cc-3oc3cc(O)ccc23)c(C(=O)O)c1 ; *SCCNC(=O)c1ccc(C(=O)O)c(-c2c3ccc(=O)cc-3oc3cc(O)ccc23)c1]

In other more particular embodiments, the present invention is directed to compounds of formula I wherein R3 is one of the structural isomers of FITC-14 shown below:

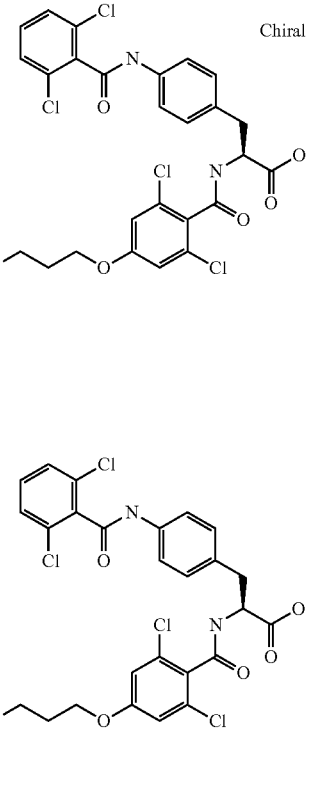

In other embodiments, the present invention is directed to a compound of formula I wherein n is 9-13, preferably 12.

In more specific embodiments, the present invention is directed to a compound of formula I selected from the group consisting of one of the following compounds (or a pharmaceutically acceptable salt or ester thereof):

VLA-4 Ligand Reagent 1
(S)-3-[4-(2,6-dichlorobenzoylamino)phenyl]-2-[[1-[2-[3-[2-[2-[2-[2-[3-(2,5-dioxo-2,5-dihydropyrrol-1-yl)propionylamino]ethoxy]ethoxy]ethoxy]ethoxy]propionylamino]ethyl]cyclopentanecarbonyl]amino] propionic acid;

VLA-4 Ligand Reagent 2
(S)-3-[4-(2,6-dichlorobenzoylamino)phenyl]-2-[[[1 -[2-3-[2-[2-[2-[2-[2-[2-[2-[3-(2,5-dioxo-2,5-dihydropyrrol-1-yl)propionylamino]-ethoxy]ethoxy]ethoxy] ethoxy]ethoxy]ethoxy]ethoxy]ethoxy]propionylamino] ethyl]cyclopentyl]carbonyl]amino]propionic acid;

VLA-4 Ligand Reagent 3
(S)-3-[4-(2,6-dichlorobenzoylamino)phenyl]-2-[[1-[2-[3-[2-[2-[2-[2-[2-[2-[2-[2]2[2- [2-[3-(2,5-dioxo-2,5-dihydropyrrol-1-yl)propionylamino]-ethoxy]ethoxy]ethoxy]ethoxy]ethoxy]ethoxy]ethoxy]ethoxy]ethoxy]ethoxy]ethoxy]ethoxy]propionylamino]ethyl] cyclopentanecarbonyl]amino]propionic acid;

VLA-4 Ligand Reagent 4
(S)-2-[[1-[2-[3-[2-[2-[2-[2-[2-[2-(2-acetylsulfanyl-ethoxy)ethoxy]ethoxy]ethoxy]ethoxy]ethoxy]ethoxy] ethoxy]propionylamino]-ethyl]-cyclopentanecarbony]-amino]-3-[4-(2,6-dichlorobenzoylamino)phenyl] propionic acid;

VLA-4 Ligand Reagent 5
(S)-3-[4-(2,6-dichlorobenzoylamino)phenyl]-2-[2,6-dichloro-4-[3-[3-[2-[2-[2-[2-[3-(2,5-dioxo-2,5-dihydropyrrol-1-yl)propionylamino]ethoxy]ethoxy]ethoxy]
ethoxy]propionylamino]propoxy]benzoylamino]
propionic acid;

VLA-4 Ligand Reagent 6

(S)-3-[4-(2,6-dichlorobenzoylamino)phenyl]-2-[2,6-dichloro-4-[3-[3-[2-[2-[2-[2-[2-[2-[2-[3-(2,5-dioxo-2,5-dihydropyrrol-1-yl)propionylamino]ethoxy]ethoxy]ethoxy]ethoxy]ethoxy]ethoxy]ethoxy]propionylamino]propoxy]benzoylamino]propionic acid;

VLA-4 Ligand Reagent 7

(S)-3-[4-(2,6-dichlorobenzoylamino)phenyl]-2-[2,6-dichloro-4-[3-[3-[2-[2-[2-[2-[2-[2-[2-[2-[2-[2-[3-(2,5-dioxo-2,5-dihydropyrrol-1-yl)propionylamino]ethoxy]ethoxy]ethoxy]ethoxy]ethoxy]ethoxy]ethoxy]ethoxy]ethoxy]ethoxy]ethoxy]propionylamino]propoxy]benzoylamino]propionic acid;

VLA-4 Ligand Reagent 8

(S)-2-[[1-[4-[3-[2-[2-[2-[2-[3-(2,5-dioxo-2,5-dihydropyrrol-1-yl)propionylamino]ethoxy]ethoxy]ethoxy]ethoxy]propionylamino]butyl]cyclopentanecarbonyl]amino]-3-[4-(1,3,6-trimethyl-2,4-dioxo-1,2,3,4-tetrahydropyrimidin-5-yl)phenyl]propionic acid;

VLA-4 Ligand Reagent 9

(S)-2-[2,6-Dichloro-4-[3-[3-[2-[2-[2-[2-[3-(2,5-dioxo-2,5-dihydropyrrol-1-yl)propionylamino]ethoxy]ethoxy]ethoxy]ethoxy]propionylamino]propoxy]benzoylamino]-3-[4-(1,3,6-trimethyl-2,4-dioxo-1,2,3,4-tetrahydropyrimidin-5-yl)phenyl]propionic acid;

VLA-4 Ligand Reagent 10

(S)-2-[2,6-dichloro-4-[3-[3-[2-[2-[2-[2-[2-[2-[2-[2-[3-(2,5-dioxo-2,5-dihydropyrrol-1-yl)propionylamino]ethoxy]ethoxy]ethoxy]ethoxy]ethoxy]ethoxy]ethoxy]ethoxy]propionylamino]propoxy]benzoylamino]-3-[4-(1,3,6-trimethyl-2,4-dioxo-1,2,3,4-tetrahydropyrimidin-5-yl)phenyl]propionic acid;

VLA-4 Ligand Reagent 11

(S)-2-[4-[(3-[2-[2-[2-[2-[3-(2,5-Dioxo-2,5-dihydropyrrol-1-yl)propionylamino]ethoxy]ethoxy]ethoxy]ethoxy]propionylamino)methyl]-2,6-difluorobenzoylamino]-3-[4-(1,3,6-trimethyl-2,4-dioxo-1,2,3,4-tetrahydropyrimidin-5-yl)phenyl]propionic acid trifluoracetate salt;

VLA-4 Ligand Reagent 12

(S)-2-[4-[(3-[2-[2-[2-[2-[2-[2-[2-[3-(2,5-Dioxo-2,5-dihydropyrrol-1-yl)propionylamino]ethoxy]ethoxy]ethoxy]ethoxy]ethoxy]ethoxy]ethoxy]propionylamino) methyl]-2,6-difluorobenzoylamino]-3-[4-(1,3,6-trimethyl-2,4-dioxo-1,2,3,4-tetrahydropyrimidin-5-yl)phenyl]propionic acid trifluoracetate salt;

VLA-4 Ligand Reagent 13

(S)-2-[4-[[3-[2-[2-[2-[2-[2-[2-[2-acetylsulfanylethoxy]ethoxy]ethoxy]ethoxy]ethoxy]ethoxy]ethoxy]propionylamino]methyl]-2,6-difluorobenzoylamino]-3-[4-(1,3,6-trimethyl-2,4-dioxo-1,2,3,4-tetrahydropyrimidin-5-yl)phenyl]propionic acid; and VLA-4 Ligand Reagent 14

(S)-2-[4-[[3-[3-[2-[2-[2-[2-[2-∂2-(2-acetylsulfanylethaoxy)ethoxy]ethoxy]ethoxy]ethoxy]ethoxy]ethoxy]propionylamino]propionyl]-[4-[(S)-1-carboxy-2-[4-[1,3,6-trimethyl-2,4-dioxo-1,2,3,4-tetrahydropyrimidin-5-yl]phenyl]ethylcarbamoyl]-3,5-difluorobenzylamino]methyl]-2,6-difluorobenzylamino]-3-[4-[1,3,6-trimethyl-2,4-dioxo-1,2,3,4-tetrahydropyrimidin-5-yl]phenyl]propionic acid.

In addition, the present invention relates to novel compositions and formulations containing compounds of formula I for the creation of nanoparticles upon combination with siRNA, resulting in the improved delivery of nucleic acids such as siRNA to the cytoplasm of target cells expressing a4B1 complexes. In particular embodiments, the present invention is directed to a siRNA formulation comprising: (1) a compound of formula I wherein R2 includes a 5'-siRNA oligonucleotide; and (2) a polycationic transfection agent.

The present invention also relates to methods of manufacturing and using such compounds and compositions. The compounds of formula I are useful as components of compositions or formulations which improve the delivery of drugs, nucleic acids, or other therapeutic compounds to tissues or cells expressing α4β1 complexes. In particular embodiments, the present invention relates to formulations containing the compounds of formula I which are useful in delivering siRNA to the cytoplasm of target cells expressing α4β1 complexes to inhibit the expression of certain proteins through RNA interference. In more particular embodiments, the present invention relates to the compounds of formula I and compositions containing such compounds that can effectively deliver siRNA to tumor cells and other cell types expressing α4β1 dimers for the treatment of cancer or inflammatory diseases. Such compounds and compositions are more efficacious and demonstrate improved knockdown capability compared to similar formulations lacking the compounds of formula I.

In one embodiment there is provided a compound of formula I:

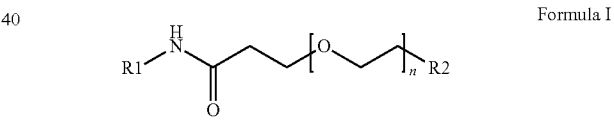

Formula I or a pharmaceutically acceptable salt or ester thereof; wherein n is 1-24 and wherein:

R1 is selected from the group consisting of:

(1) a compound of the formula:

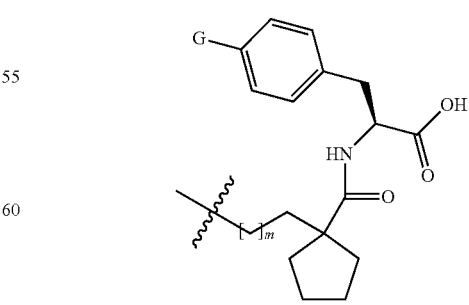

wherein m is 0-3 and G is selected from the group consisting of:

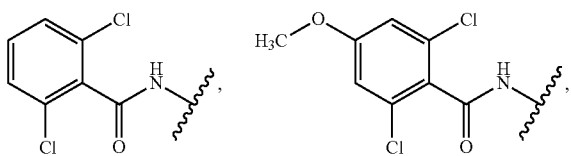 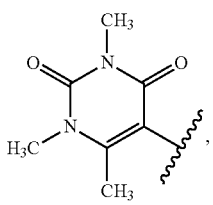 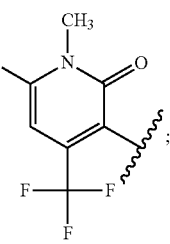
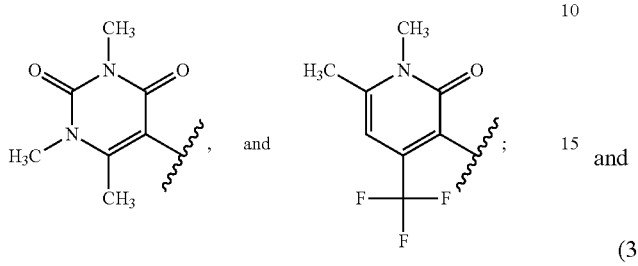
and
(2) a compound of the formula:
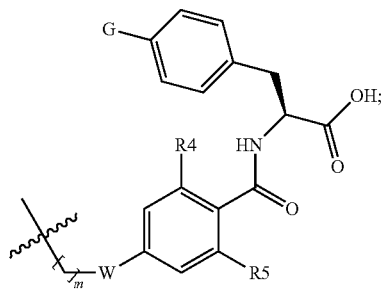
wherein m is 0-3, R4 and R5 are independently hydrogen or halogen, W is O or CH₂, and G is selected from the group consisting of:
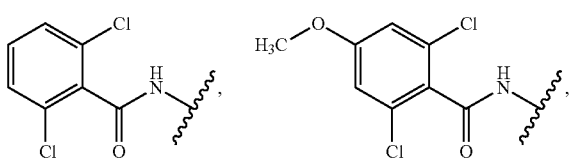
-continued
and
(3) a compound of the formula:
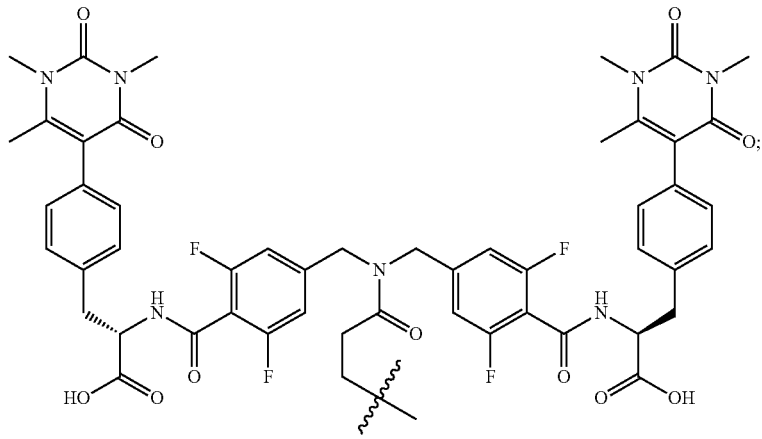 [SMILES: *CCC(=O)N(Cc1cc(F)c(C(=O)N[C@@H](Cc2ccc(-c3c(C)n(C)c(=O)n(C)c3=O)cc2)C(=O)O)c(F)c1)Cc1cc(F)c(C(=O)N[C@@H](Cc2ccc(-c3c(C)n(C)c(=O)n(C)c3=O)cc2)C(=O)O)c(F)c1]
R2 is selected from the group consisting of:
(1) a compound of the formula:
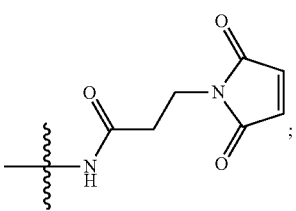 [SMILES: *NC(=O)CCN1C(=O)C=CC1=O]
(2) a compound of the formula:
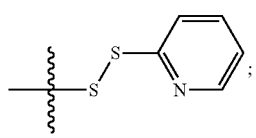 [SMILES: *SSc1ccccn1]

(3) a compound of the formula:

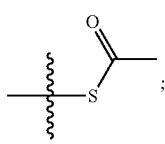 [SMILES: *SC(C)=O]

and (4) a compound of the formula:

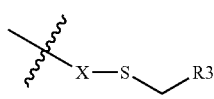

wherein R3 is a conjugated moiety and X represents either sulfur or a compound of the formula:

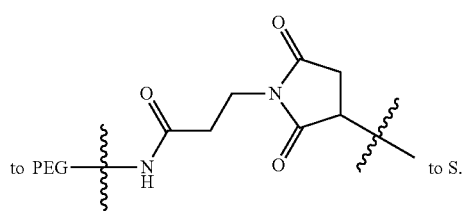

In one embodiment there is provided a compound of formula I:

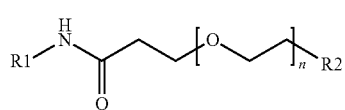

Formula I or a pharmaceutically acceptable salt or ester thereof; wherein n is 1-24 and wherein: R1 is

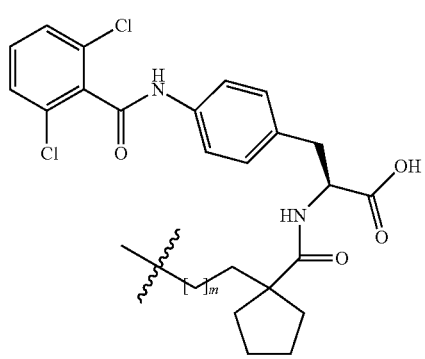

wherein m is 0-3.

R2 is selected from the group consisting of:

(1) a compound of the formula:

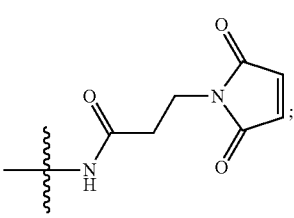 [SMILES: *NC(=O)CCN1C(=O)C=CC1=O]

(2) a compound of the formula:

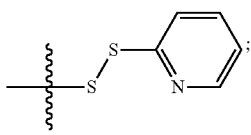 [SMILES: *SSc1ccccn1]

(3) a compound of the formula:

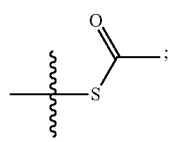 [SMILES: *SC(C)=O]

and (4) a compound of the formula:

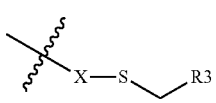

wherein R3 is a conjugated moiety and X represents either sulfur or a compound of the formula:

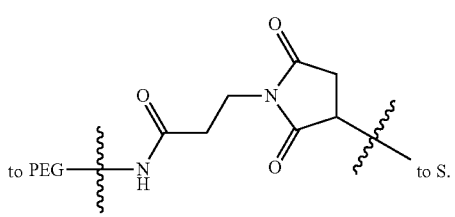

In one embodiment there is provided a compound of formula I:

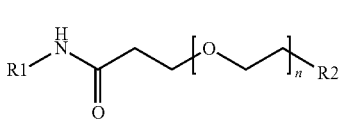

Formula I or a pharmaceutically acceptable salt or ester thereof; wherein n is 1-24 and wherein:

R1 is a compound of the formula:

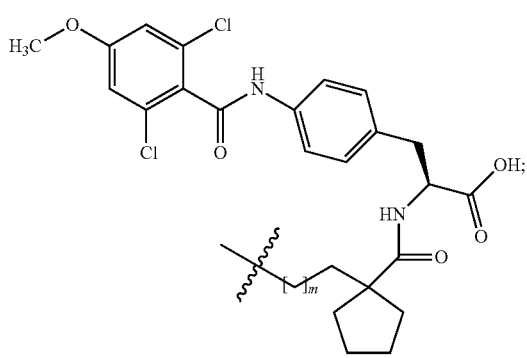

wherein m is 0-3.
R2 is selected from the group consisting of:
(1) a compound of the formula:

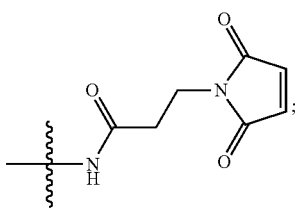 [SMILES: *NC(=O)CCN1C(=O)C=CC1=O]

(2) a compound of the formula:

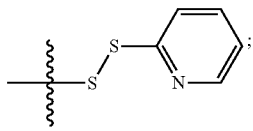 [SMILES: *SSc1ccccn1]

(3) a compound of the formula:

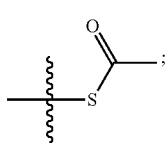 [SMILES: *SC(C)=O]

and (4) a compound of the formula:

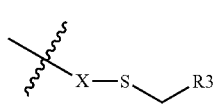

wherein R3 is a conjugated moiety and X represents either sulfur or a compound of the formula:

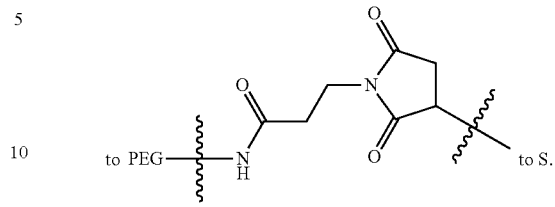

In one embodiment there is provided a compound of formula I:

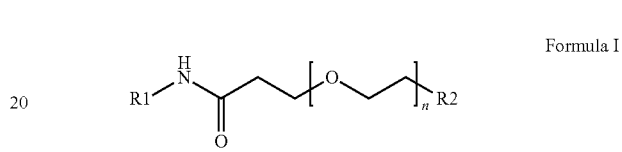

Formula I or a pharmaceutically acceptable salt or ester thereof; wherein n is 1-24 and wherein:
R1 is a compound of the formula:

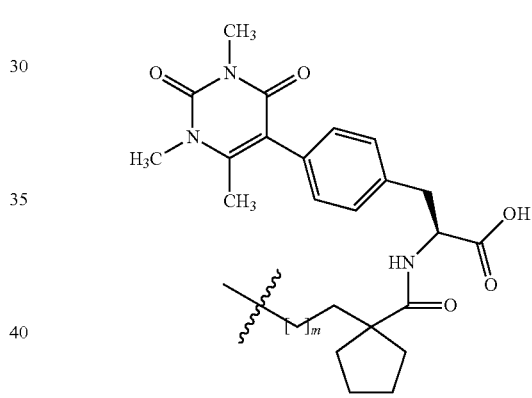

wherein m is 0-3.
R2 is selected from the group consisting of:
(1) a compound of the formula:

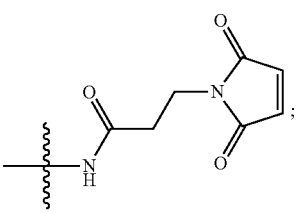 [SMILES: *NC(=O)CCN1C(=O)C=CC1=O]

(2) a compound of the formula:

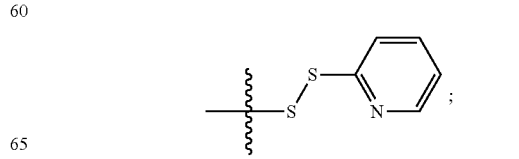

(3) a compound of the formula:

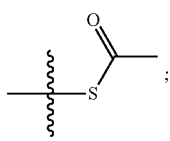 [SMILES: *SC(C)=O]

and (4) a compound of the formula:

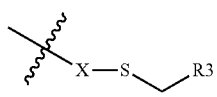

wherein R3 is a conjugated moiety and X represents either sulfur or a compound of the formula:

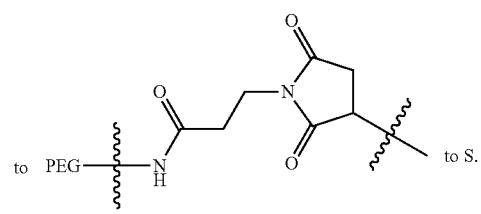

In one embodiment there is provided a compound of formula I:

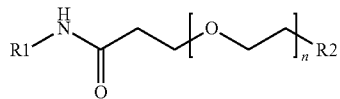

Formula I or a pharmaceutically acceptable salt or ester thereof; wherein n is 1-24 and wherein:

R1 is a compound of the formula:

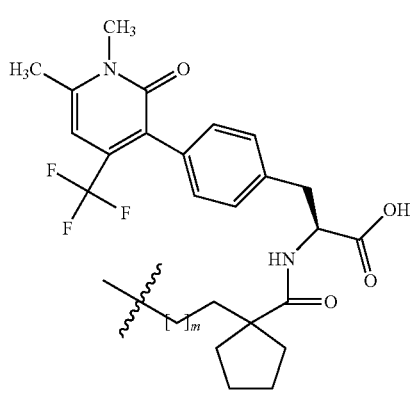

wherein m is 0-3.

R2 is selected from the group consisting of:
(1) a compound of the formula:

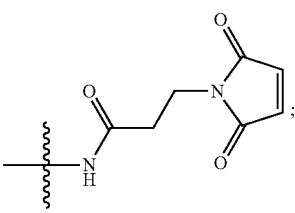 [SMILES: *NC(=O)CCN1C(=O)C=CC1=O]

(2) a compound of the formula:

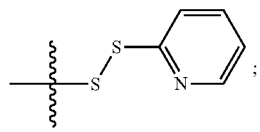 [SMILES: *SSc1ccccn1]

(3) a compound of the formula:

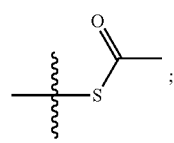

and (4) a compound of the formula:

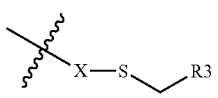

wherein R3 is a conjugated moiety and X represents either sulfur or a compound of the formula:

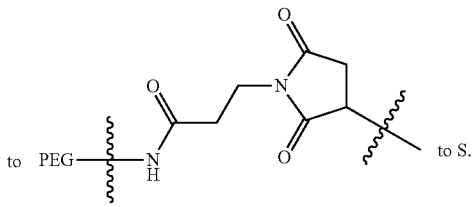

In one embodiment there is provided a compound of formula I:

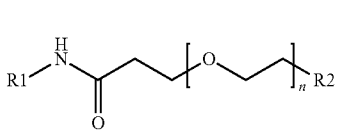

Formula I or a pharmaceutically acceptable salt or ester thereof; wherein n is 1-24 and wherein:

R1 is a compound of the formula:

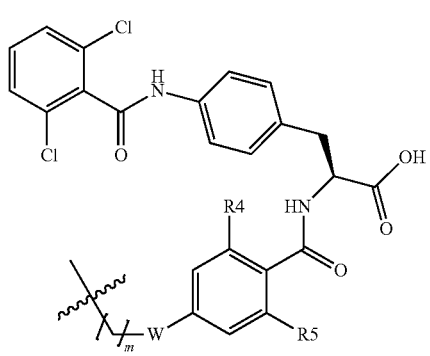

wherein m is 0-3, R4 and R5 are hydrogen or halogen, and W is O or CH$_2$.

R2 is selected from the group consisting of:

(1) a compound of the formula:

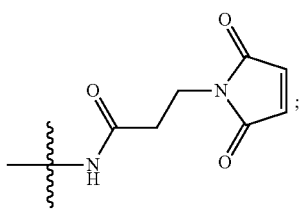 [SMILES: *NC(=O)CCN1C(=O)C=CC1=O]

(2) a compound of the formula:

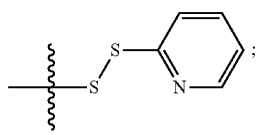 [SMILES: *SSc1ccccn1]

(3) a compound of the formula:

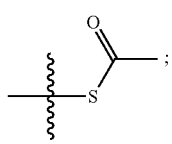 [SMILES: *SC(C)=O]

and (4) a compound of the formula:

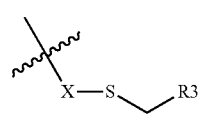

wherein R3 is a conjugated moiety and X represents either sulfur or a compound of the formula:

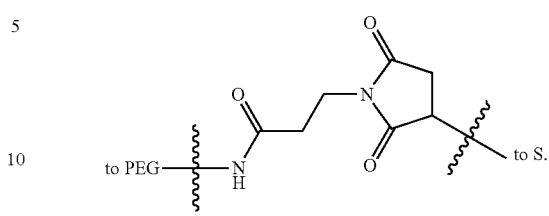

In one embodiment there is provided a compound of formula I:

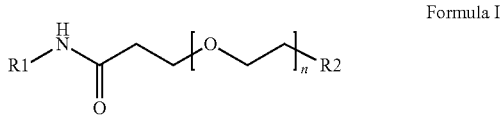

Formula I or a pharmaceutically acceptable salt or ester thereof; wherein n is 1-24 and wherein:

R1 is a compound of the formula:

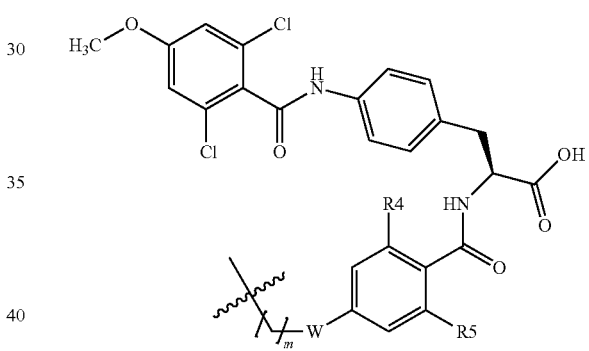

wherein m is 0-3, R4 and R5 are hydrogen or halogen, and W is O or CH$_2$.

R2 is selected from the group consisting of:

(1) a compound of the formula:

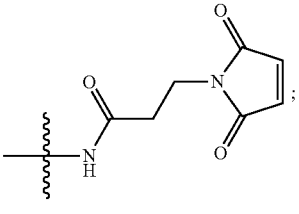 [SMILES: *NC(=O)CCN1C(=O)C=CC1=O]

(2) a compound of the formula:

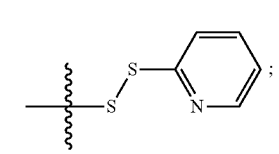

(3) a compound of the formula:

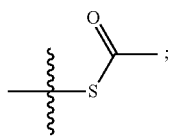 [SMILES: *SC(C)=O]

and (4) a compound of the formula:

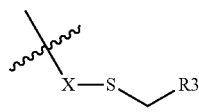

wherein R3 is a conjugated moiety and X represents either sulfur or a compound of the formula:

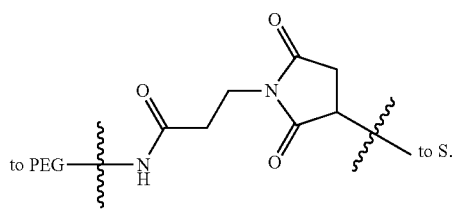

In one embodiment there is provided a compound of formula I:

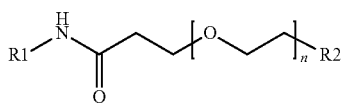

Formula I or a pharmaceutically acceptable salt or ester thereof; wherein n is 1-24 and wherein:

R1 is a compound of the formula:

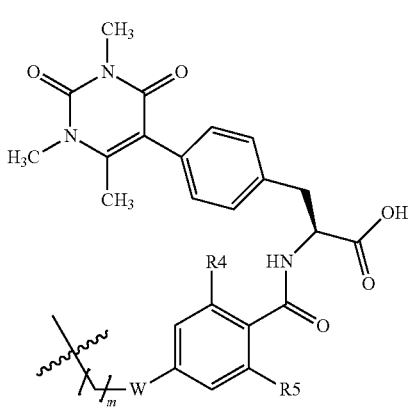

wherein m is 0-3, R4 and R5 are hydrogen or halogen, and W is O or $CH_2$.

R2 is selected from the group consisting of:

(1) a compound of the formula:

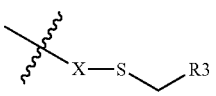

(2) a compound of the formula:

(3) a compound of the formula:

and (4) a compound of the formula:

wherein R3 is a conjugated moiety and X represents either sulfur or a compound of the formula:

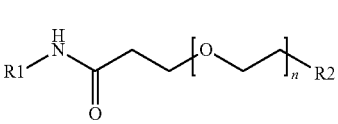

In one embodiment there is provided a compound of formula I:

Formula I or a pharmaceutically acceptable salt or ester thereof; wherein n is 1-24 and wherein:

R1 is a compound of the formula:

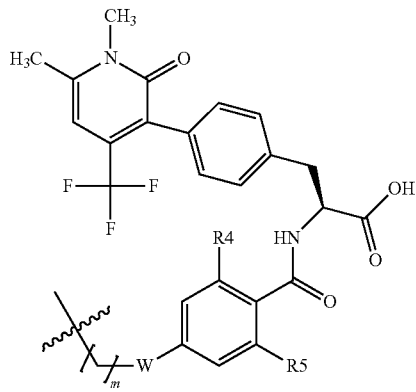

wherein m is 0-3, R4 and R5 are hydrogen or halogen, and W is O or CH₂.

R2 is selected from the group consisting of:

(1) a compound of the formula:

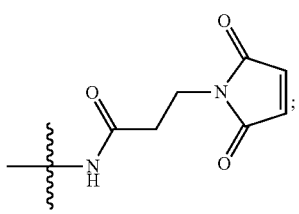 [SMILES: *NC(=O)CCN1C(=O)C=CC1=O]

(2) a compound of the formula:

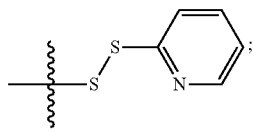 [SMILES: *SSc1ccccn1]

(3) a compound of the formula:

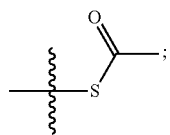 [SMILES: *SC(C)=O]

and (4) a compound of the formula:

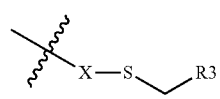

wherein R3 is a conjugated moiety and X represents either sulfur or a compound of the formula:

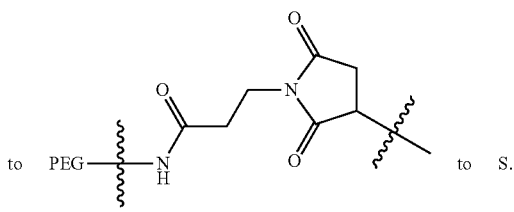

In one embodiment there is provided a compound of formula I:

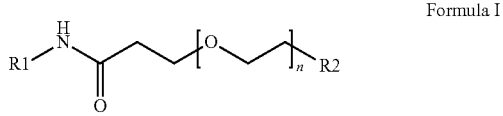

Formula I or a pharmaceutically acceptable salt or ester thereof; wherein n is 1-24 and wherein:

R1 is a compound of the formula:

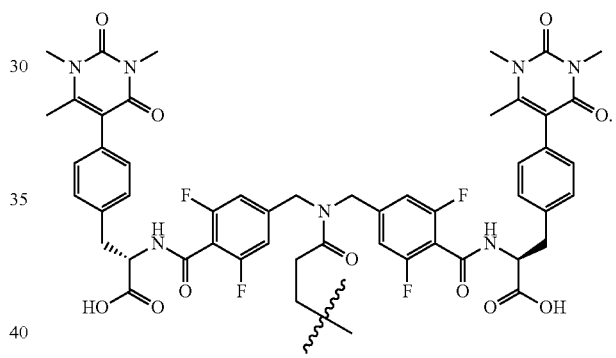

R2 is selected from the group consisting of:

(1) a compound of the formula:

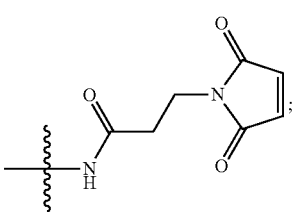 [SMILES: *NC(=O)CCN1C(=O)C=CC1=O]

(2) a compound of the formula:

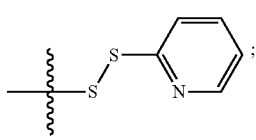 [SMILES: *SSc1ccccn1]

(3) a compound of the formula:

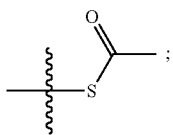 [SMILES: *SC(C)=O]

and (4) a compound of the formula:

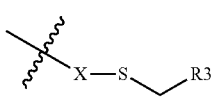

wherein R3 is a conjugated moiety and X represents either sulfur or a compound of the formula:

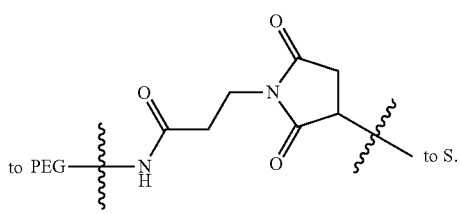

In one embodiment there is provided a compound of formula I:

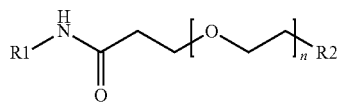

Formula I or a pharmaceutically acceptable salt or ester thereof; wherein n is 1-24 and wherein:

R1 is selected from the group consisting of:

(1) a compound of the formula:

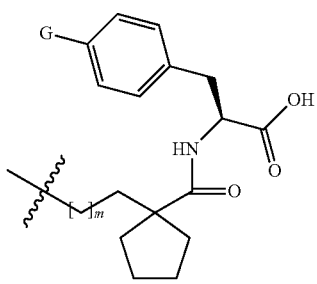

wherein m is 0-3 and G is selected from the group consisting of:

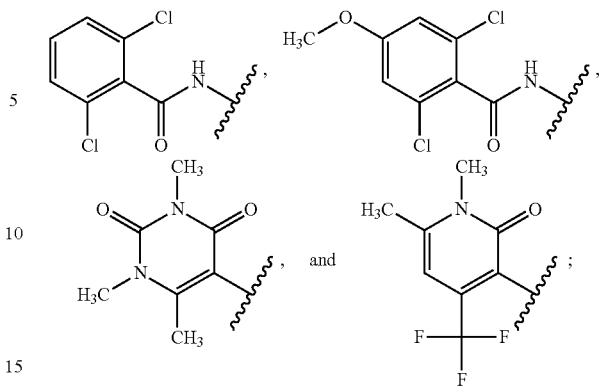

(2) a compound of the formula:

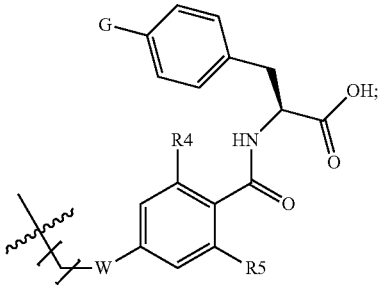

wherein m is 0-3, R4 and R5 are independently hydrogen or halogen, W is O or $CH_2$, and G is selected from the group consisting of:

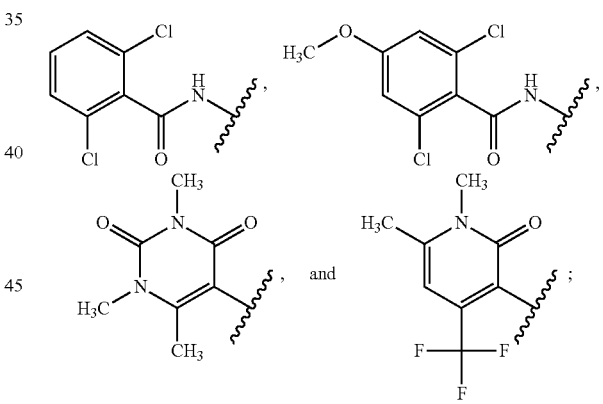

and (3) a compound of the formula:

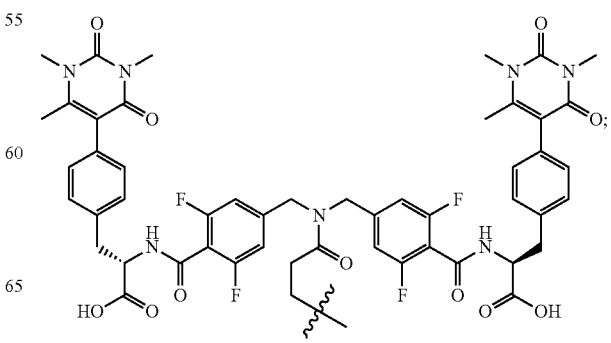

R2 is a compound of the formula:

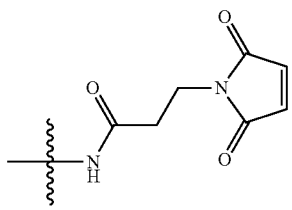

wherein R3 is a conjugated moiety and X represents either sulfur or a compound of the formula:

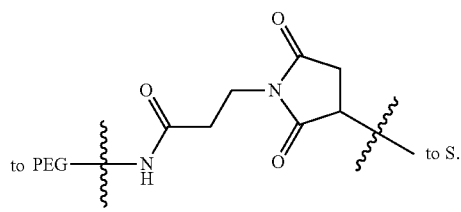

In one embodiment there is provided a compound of formula I:

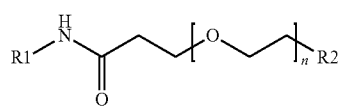

Formula I or a pharmaceutically acceptable salt or ester thereof; wherein n is 1-24 and wherein:

R1 is selected from the group consisting of:

(1) a compound of the formula:

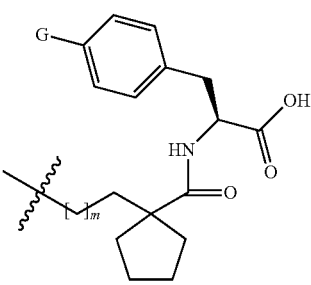

wherein m is 0-3 and G is selected from the group consisting of:

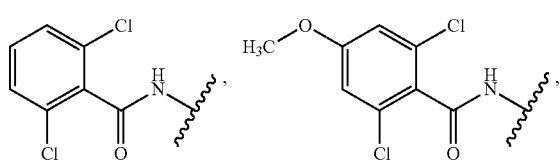

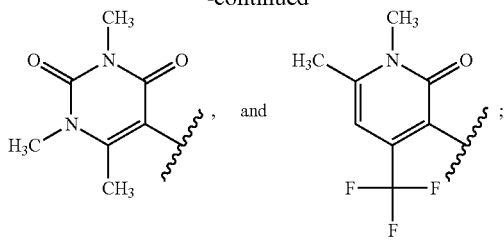

(2) a compound of the formula:

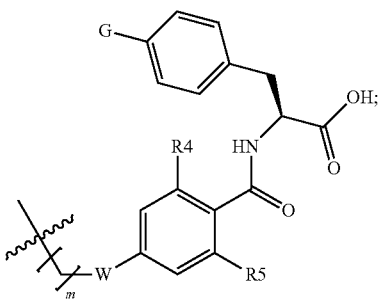

wherein m is 0-3, R4 and R5 are independently hydrogen or halogen, W is O or $CH_2$, and G is selected from the group consisting of:

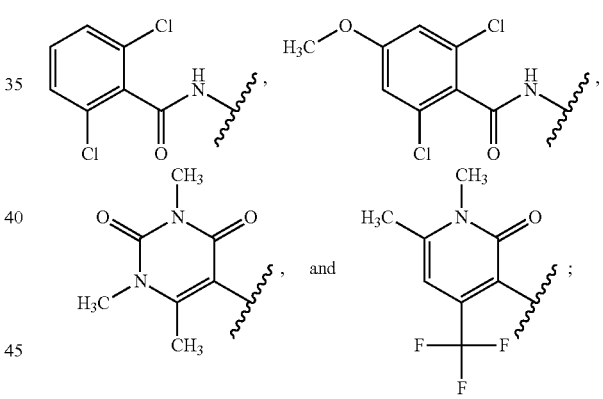

and (3) a compound of the formula:

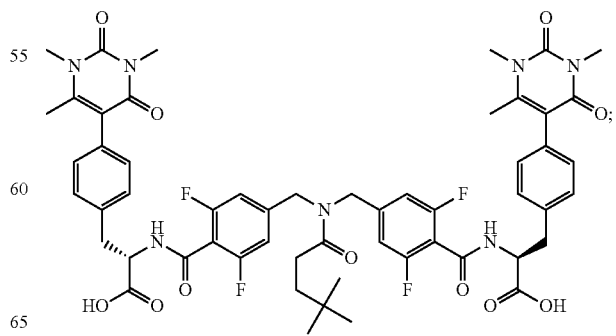

R2 is a compound of the formula:

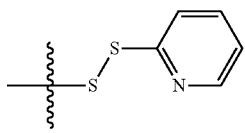

wherein R3 is a conjugated moiety and X represents either sulfur or a compound of the formula:

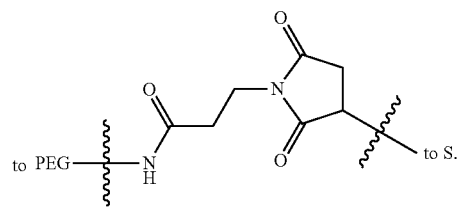

In one embodiment there is provided a compound of formula I:

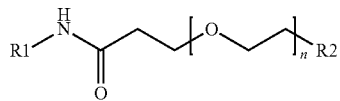

Formula I or a pharmaceutically acceptable salt or ester thereof; wherein n is 1-24 and wherein:

R1 is selected from the group consisting of:

(1) a compound of the formula:

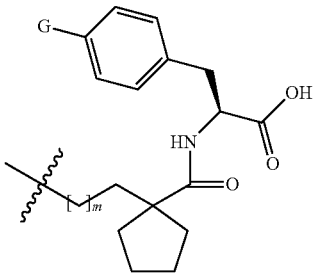

wherein m is 0-3 and G is selected from the group consisting of:

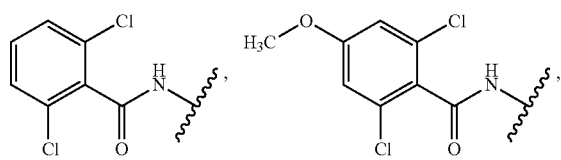

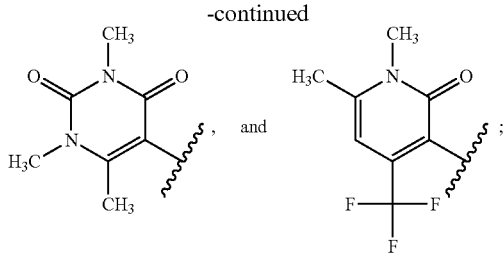

(2) a compound of the formula:

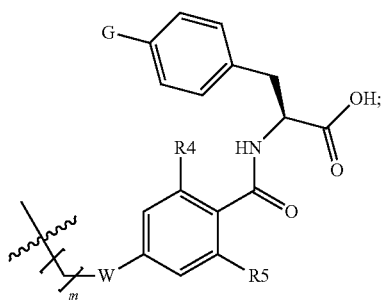

wherein m is 0-3, R4 and R5 are independently hydrogen or halogen, W is O or $CH_2$, and G is selected from the group consisting of:

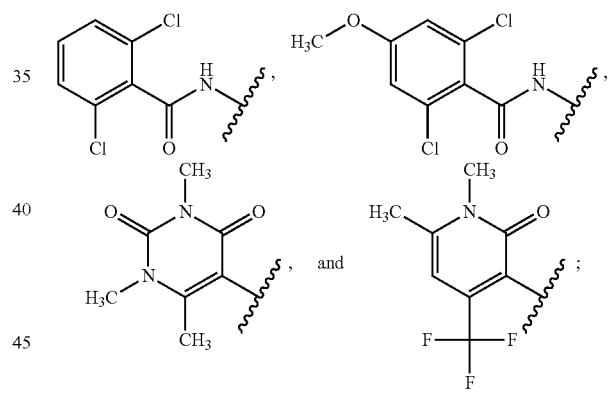

and (3) a compound of the formula:

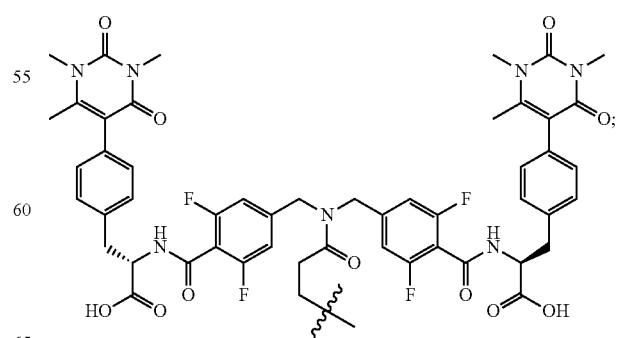

R2 is a compound of the formula:

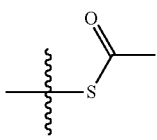

wherein R3 is a conjugated moiety and X represents either sulfur or a compound of the formula:

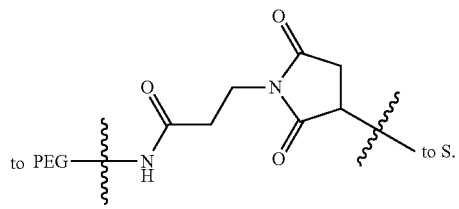

In one embodiment there is provided a compound of formula I:

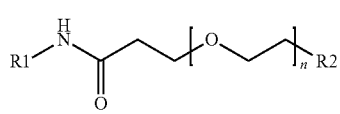

Formula I or a pharmaceutically acceptable salt or ester thereof; wherein n is 1-24 and wherein:

R1 is selected from the group consisting of:

(1) a compound of the formula:

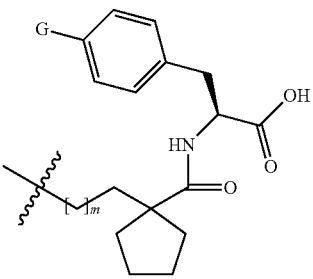

wherein m is 0-3 and G is selected from the group consisting of:

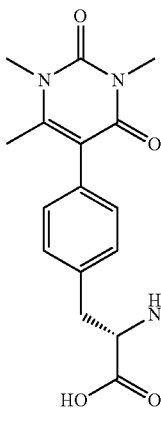

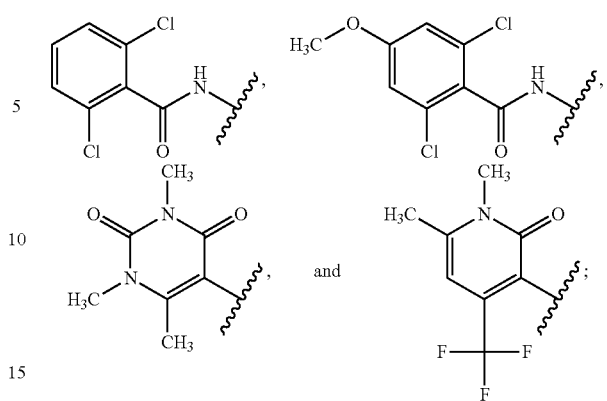

(2) a compound of the formula:

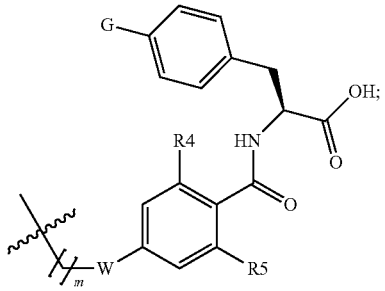

wherein m is 0-3, R4 and R5 are independently hydrogen or halogen, W is O or $CH_2$, and G is selected from the group consisting of:

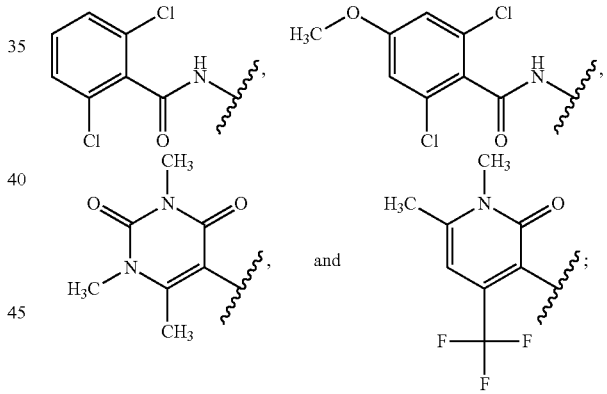

and (3) a compound of the formula:

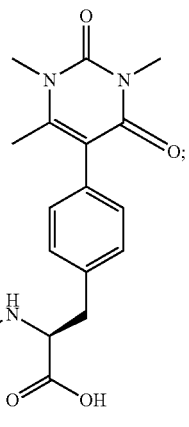

R2 is a compound of the formula:

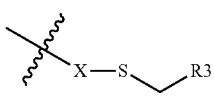

wherein R3 is a single or double stranded oligonucleotide and X represents either sulfur or a compound of the formula:

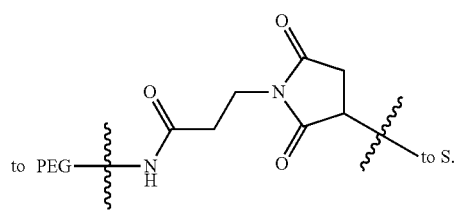

In one embodiment there is provided a compound of formula I:

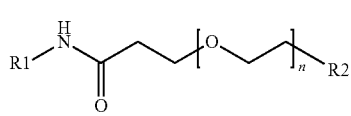

Formula I or a pharmaceutically acceptable salt or ester thereof; wherein n is 1-24 and wherein:
R1 is selected from the group consisting of:
(1) a compound of the formula:

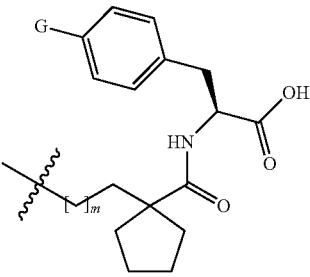

wherein m is 0-3 and G is selected from the group consisting of:

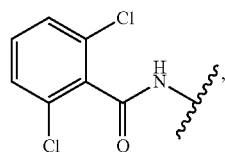
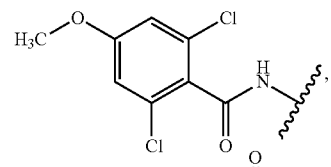

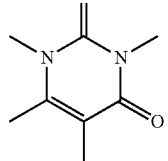

-continued

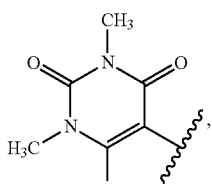
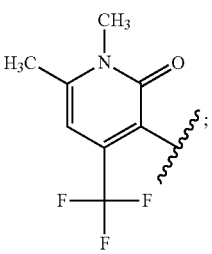

and (2) a compound of the formula:

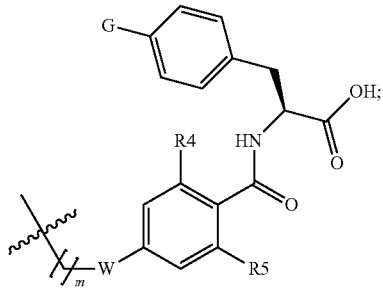

wherein m is 0-3, R4 and R5 are independently hydrogen or halogen, W is O or $CH_2$, and G is selected from the group consisting of:

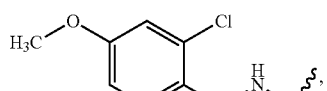

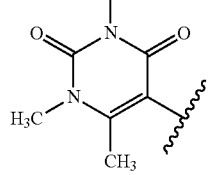
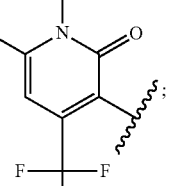

and

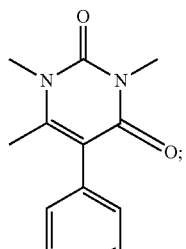

and (3) a compound of the formula:

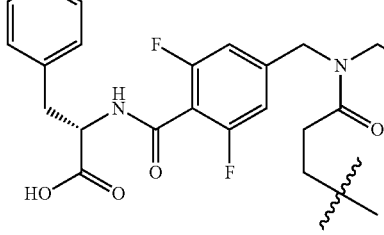
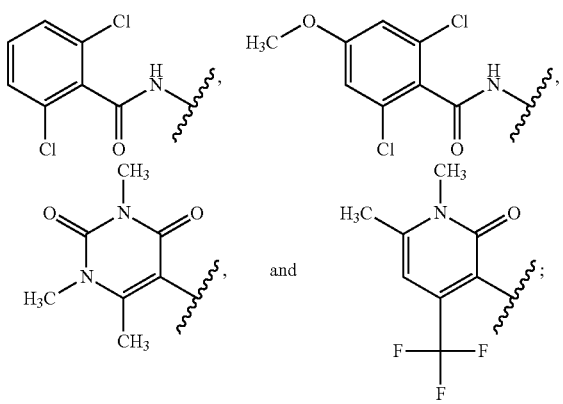
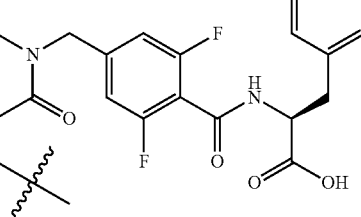

R2 is selected from the group consisting of:

(1) a compound of the formula:

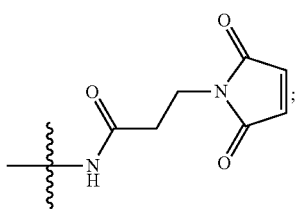 [SMILES: *NC(=O)CCN1C(=O)C=CC1=O]

(2) a compound of the formula:

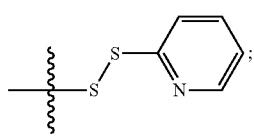 [SMILES: *SSc1ccccn1]

(3) a compound of the formula:

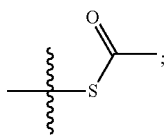 [SMILES: *SC(C)=O]

and (4) a compound of the formula:

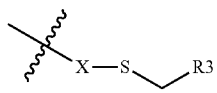

wherein R3 is a siRNA molecule

GENERAL SYNTHESIS OF THE COMPOUNDS OF THE INVENTION

Suitable processes for synthesizing compounds of formula I are provided in the examples. Generally, compounds of formula I can be prepared according to the schemes illustrated below. Unless otherwise indicated, the variables n and R1 and R2 in the schemes below are defined in the same manner as defined previously for the genus of formula I.

General Synthesis of Maleimide-(PEG)n-integrin Antagonists Conjugating Agents Compounds such as 26 in scheme 1 of various lengths of PEG are commercially available (e.g., from Pierce BioScience). Such compounds can also be made as by acylating the amino termini of PEG amino acids with 3-(2,5-dioxo-2,5-dihydro-pyrrol-1-yl)-propionic acid under amide bond forming conditions, followed by formation of reactive N-hydroxysuccinic esters by reaction of N-hydroxy succinic acid under ester forming conditions. As shown in scheme 1, reacting the compounds of 26 with compounds containing primary or secondary amines such as 27 are conducted in aprotic or protic solvents in the presence of basic amines such as DIEA (diisopropylethylamine) at room temperature generating the PEGylated intermediates of 28.

Scheme 1

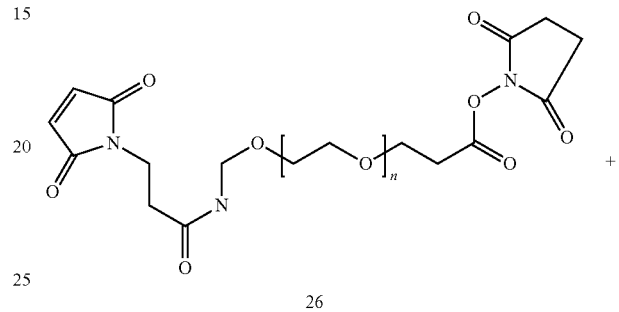

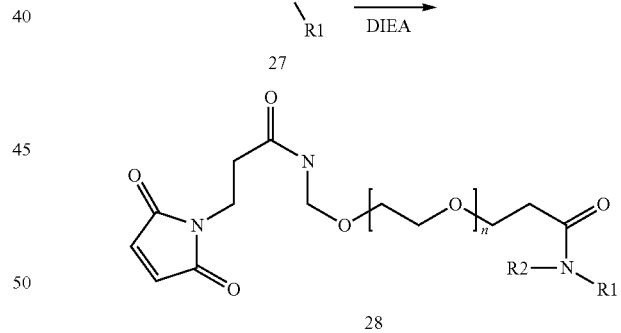

Compounds such as 29 in scheme 2 for which R4 is thioacetyl or 2-dithiopyridyl and having PEG moieties of various lengths are also commercially available (e.g., from Pierce BioScience). Reaction of compounds having the structure of 29 with compounds containing primary or secondary amines such as 27 are conducted in aprotic or protic solvents in the presence of basic amines such as DIEA (diisopropylethylamine) at room temperature generating the PEGylated intermediates of 30.

Scheme 2
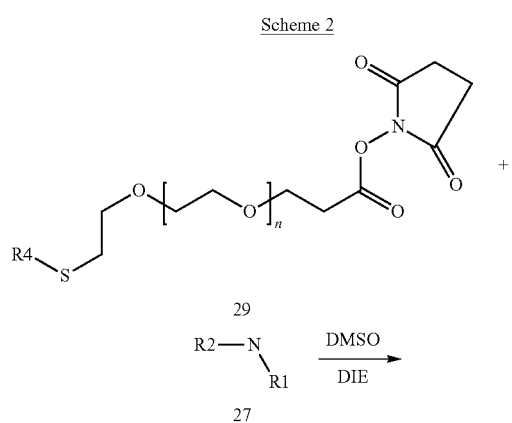
29
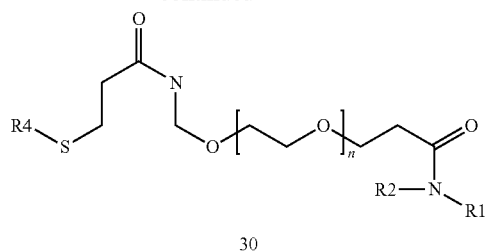
30
As a specific not limiting example for this invention, intermediate 26 is reacted with 31 to produce the maleimide intermediate of 32 as shown in Scheme 3:
Scheme 3
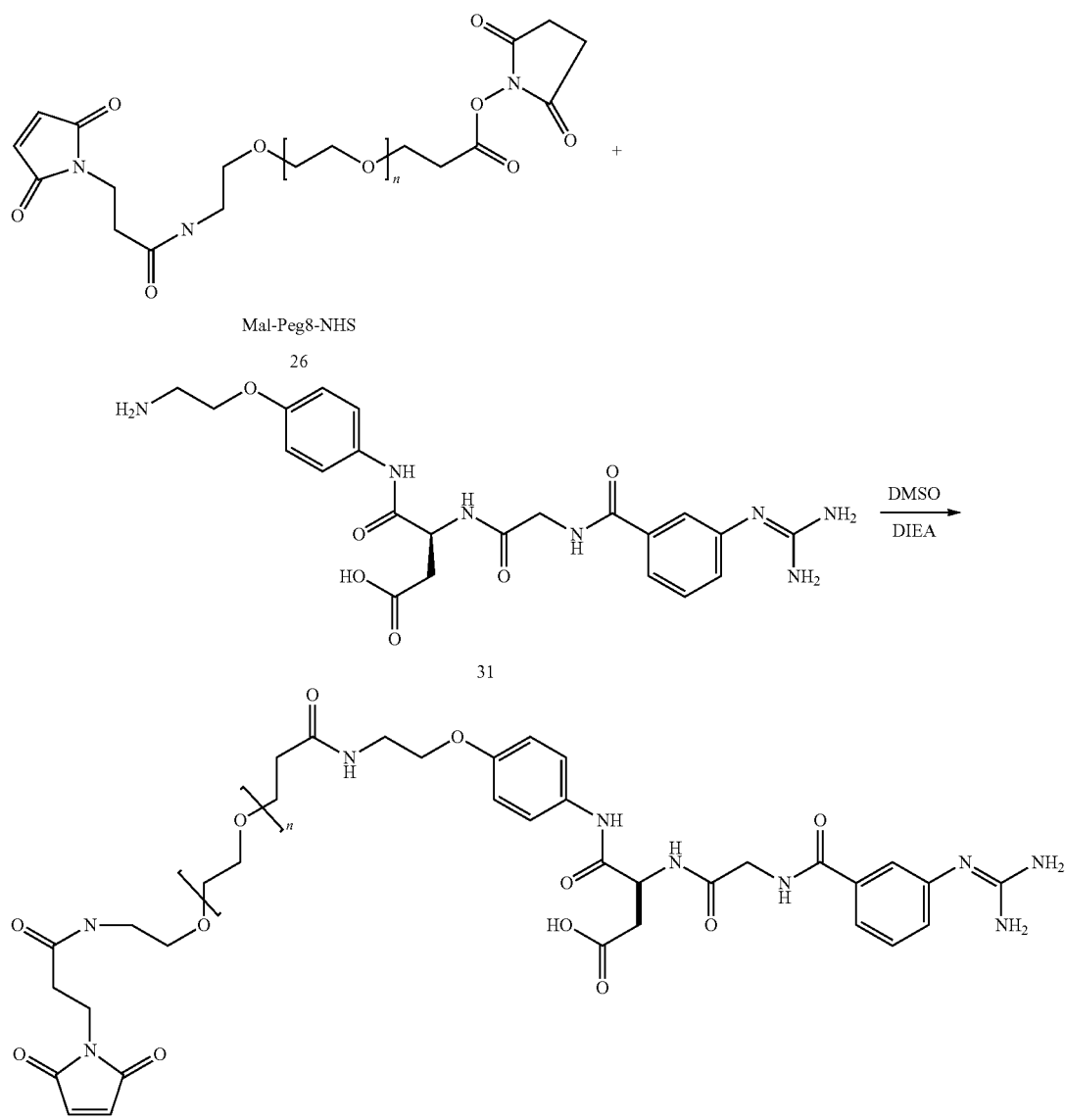

In a similar manner, intermediate 26 can be reacted with 33 to produce the maleimide intermediate of 34 as shown in Scheme 4:
Scheme 4
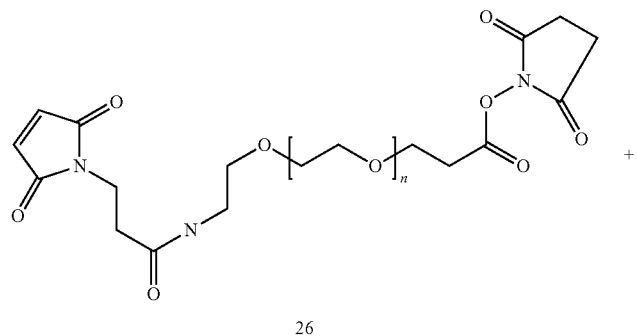
26
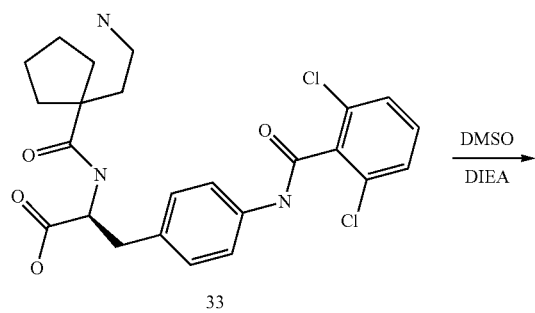
33
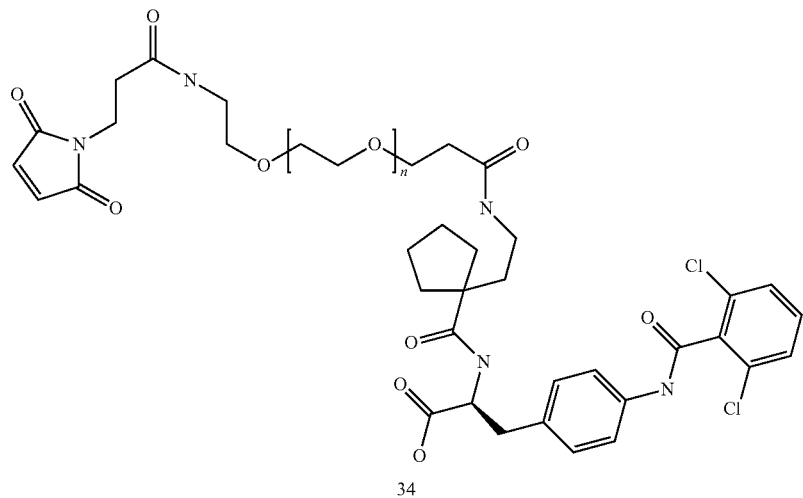
34

In a similar manner, intermediate 29 can be reacted with 35 to produce the intermediate of 36 as shown in Scheme 5 in which R4 represents either thioacetyl or 2-dithiopyridyl:
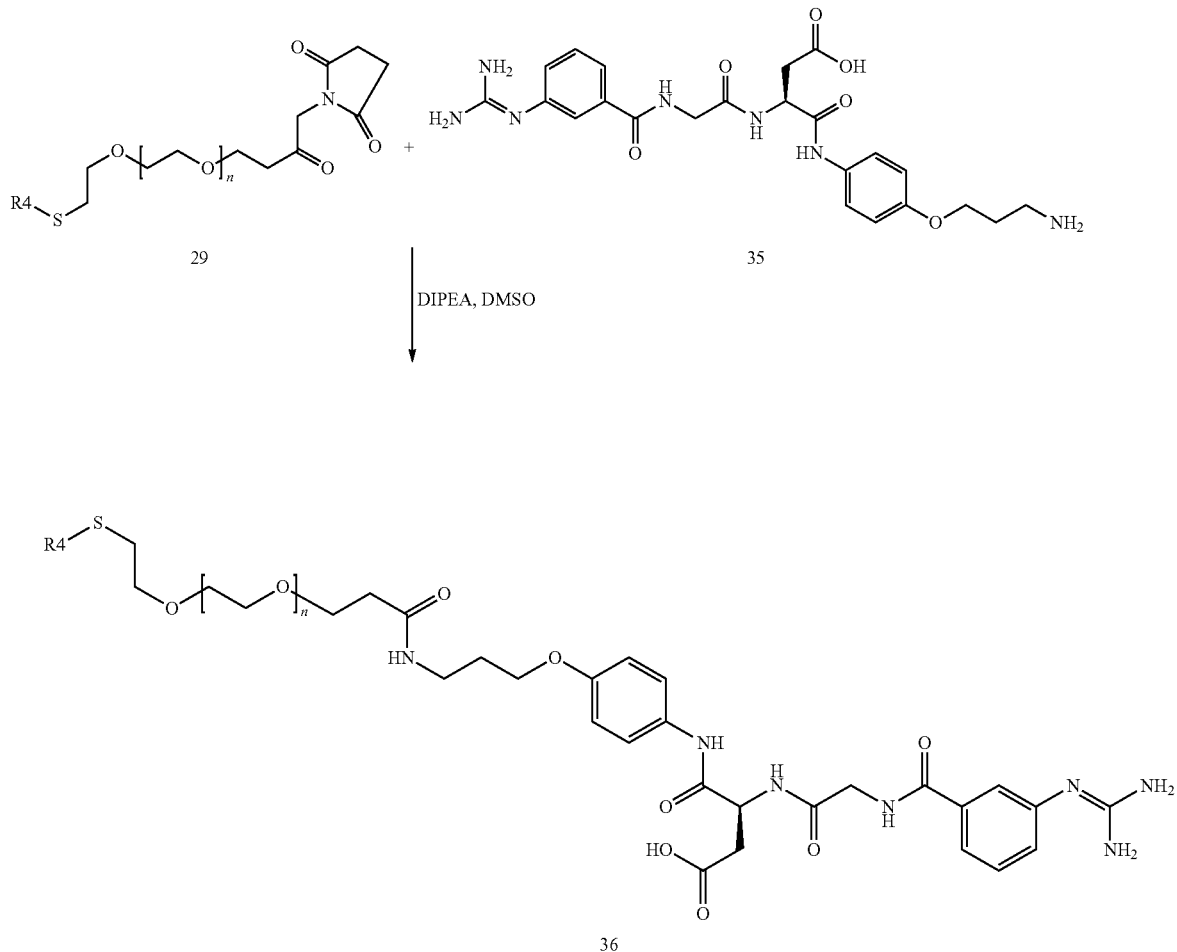
In a similar manner, intermediate 29 can be reacted with 37 to produce intermediate of 38 as shown in Scheme 6 in which R4 represents either thioacetyl or 2-dithiopyridyl:
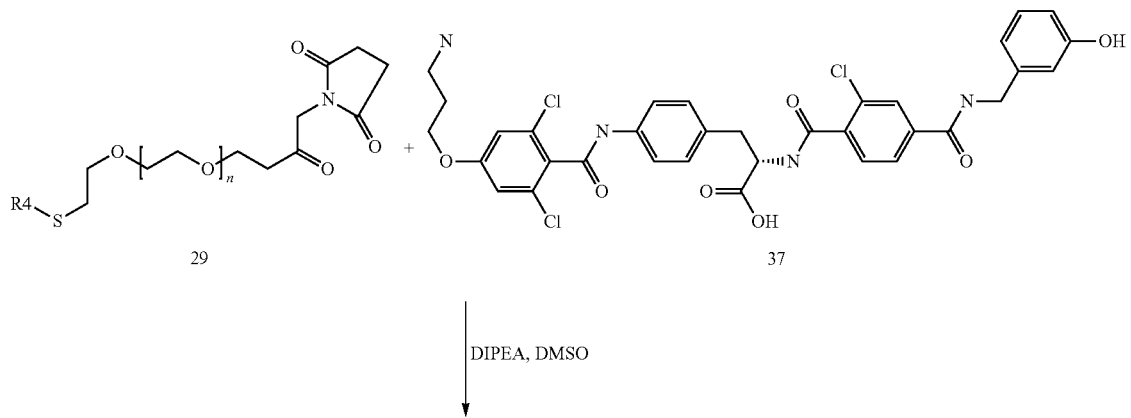

-continued

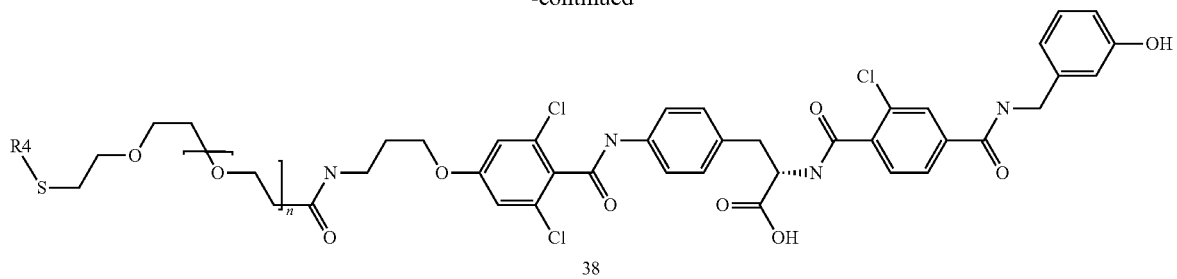

38

For compounds of general structure 26 or 29, different PEG lengths are available or easily made by those skilled in the art; preferably n=8-24. This topic has been thoroughly reported and reviewed (e.g., Chemistry for peptide and protein PEGylation, *Advanced Drug Delivery Reviews* Volume 54, Issue 4, 17 Jun. 2002, Pages 459-476).

Intermediate 31 can be synthesized in a manner similar to that which has been reported (e.g., Sidduri, A. et al. *Bioorganic & Medicinal Chemistry Letters*, 2002, 12, 2475-2478) as shown in Scheme 7:

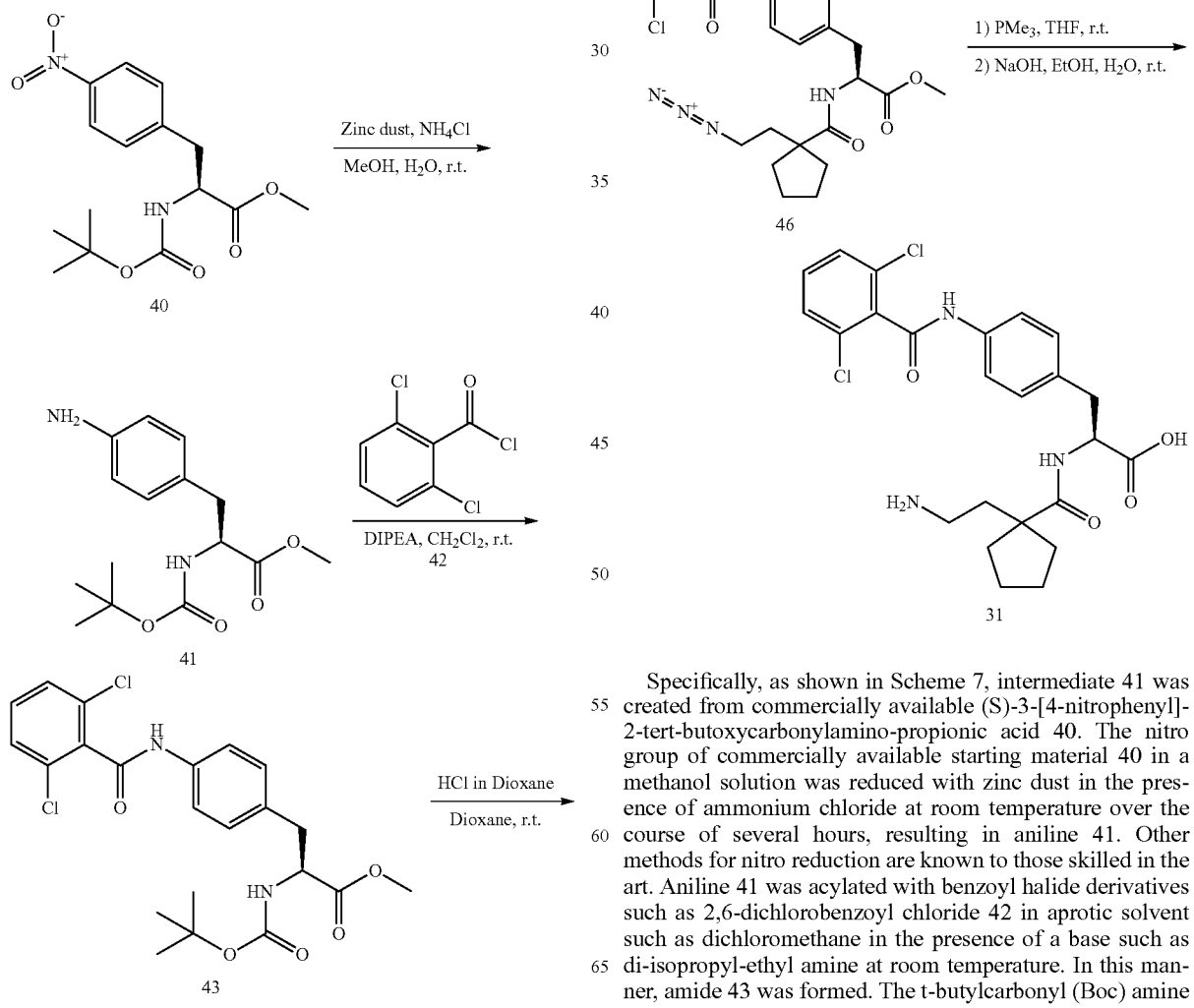

Specifically, as shown in Scheme 7, intermediate 41 was created from commercially available (S)-3-[4-nitrophenyl]-2-tert-butoxycarbonylamino-propionic acid 40. The nitro group of commercially available starting material 40 in a methanol solution was reduced with zinc dust in the presence of ammonium chloride at room temperature over the course of several hours, resulting in aniline 41. Other methods for nitro reduction are known to those skilled in the art. Aniline 41 was acylated with benzoyl halide derivatives such as 2,6-dichlorobenzoyl chloride 42 in aprotic solvent such as dichloromethane in the presence of a base such as di-isopropyl-ethyl amine at room temperature. In this manner, amide 43 was formed. The t-butylcarbonyl (Boc) amine protecting group was removed according to standard methods known to those skilled in the art, such as by treatment with an HCl solution in dioxane at room temperature; this resulted in hydrochloride 44. Hydrochloride 44 was treated with amide bond forming conditions (also well known to those skilled in the art) in the presence of known 1-(2-azido-ethyl)-cyclopentanecarboxylic acid 45 resulting in the production of di-amide 46. The azide group of intermediate 46 was reduced by treatment with tri-alkyl phosphine in an aprotic solvent such as tetrahydrofuran at room temperature. Further, the methyl ester was saponified by treatment with sodium hydroxide in a solvent mixture such as ethanol and tetrahydrofuran at an elevated temperature such as 50° C. and for 15 hours. This process resulted in the formation of intermediate 31 which may also be presented as a zwitterion.

Attachment of the PEG moiety is also possible with intermediate 39, which is synthesized as shown in Scheme 8. Specifically, 3,5-dichlorophenol 47 is protected with tri-isopropylsilylchloride in the presence of a base such as imidazole in a polar aprotic solvent such as DMF before reaction with a strong base such as butyl lithium in anhydrous tetrahydrofuran at low temperatures such as −78 degrees C. The resulting lithium complex is quenched with carbon dioxide added in the form of dry ice resulting in intermediate 48, a benzoic acid derivative. Intermediate 48 is then chlorinated to form the acyl chloride by treatment in an aprotic solvent such as toluene with sulfonyl chloride ($SOCl_2$). At this time, the acyl chloride is then reacted with amine hydrochloride 49 in the presence of base such as di-isopropylethyl amine (DIPEA) in aprotic solvent such as dichloromethane (DCM), thereby forming intermediate 50. The silyl protecting group of intermediate 50 is removed by treatment with tetrabutyl ammonium fluoride (TBAF) in a protic solvent such as tetrahydrofuran at room temperature. This phenol intermediate is reacted in the presence of a base such as potassium carbonate ($K_2CO_3$) in an aprotic solvent such as dimethylformamide (DMF) with 3-N-t-butyl-carbomate-1-bromopropane. In this manner intermediate 52 is formed which upon deprotection with trifluoroacetic acid (TFA) and subsequent hydrolysis with a base such as sodium hydroxide in protic solvent such as ethanol forms intermediate 39:

Scheme 8

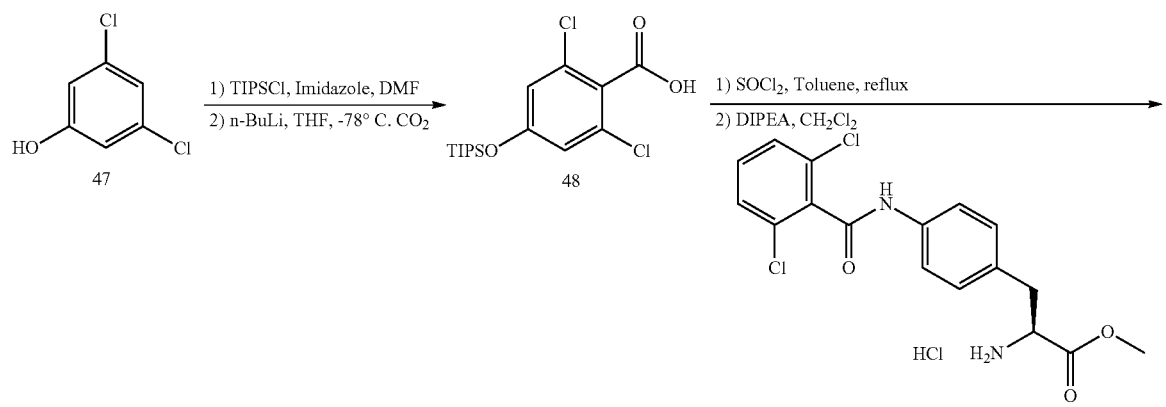

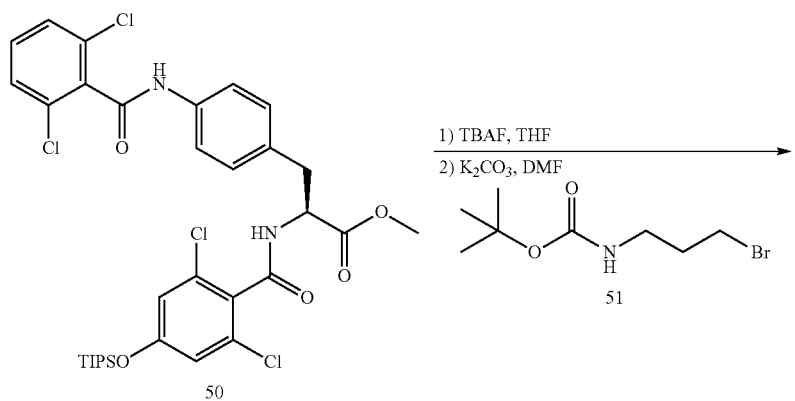

-continued
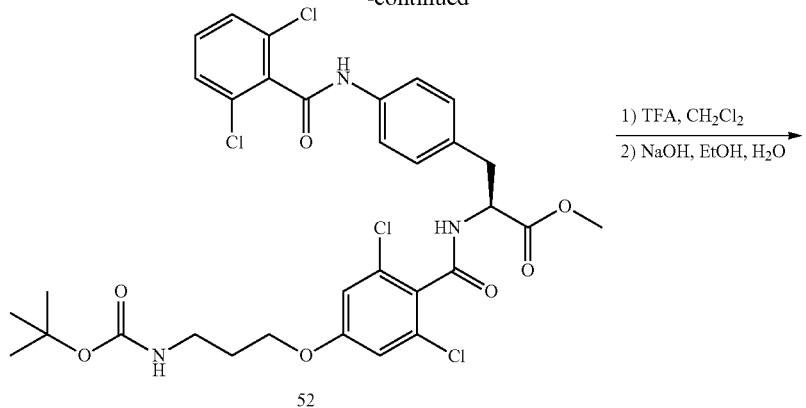
1) TFA, CH₂Cl₂
2) NaOH, EtOH, H₂O
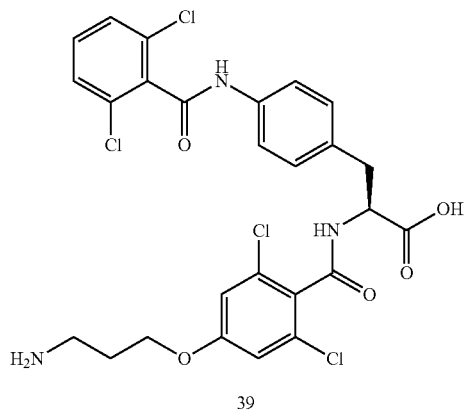
Synthesis of VLA-4 Antagonist Derivatizing Agents
The synthesis of a compound of the formula:
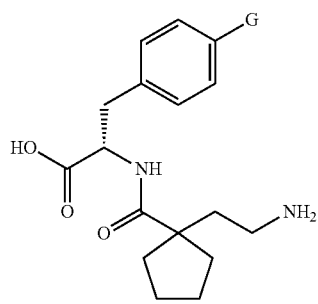
wherein:
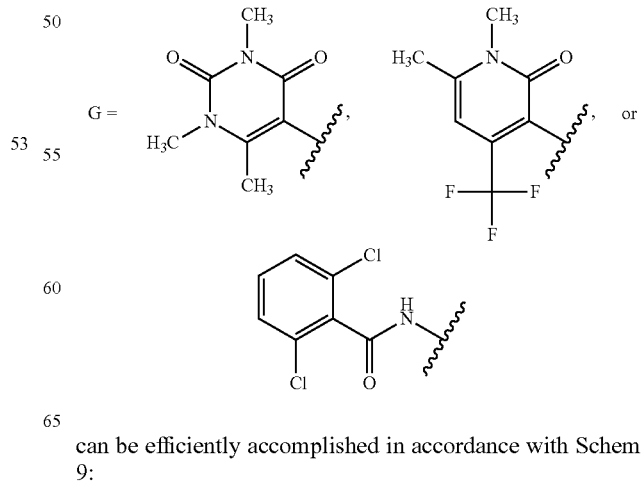
can be efficiently accomplished in accordance with Scheme 9:

Scheme 9

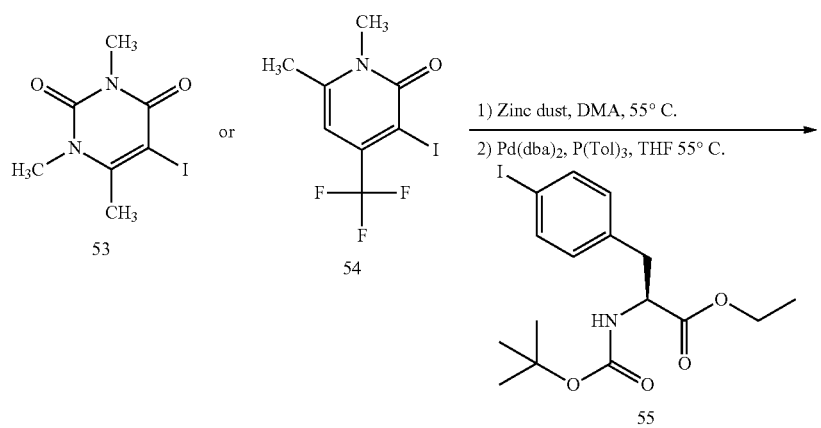

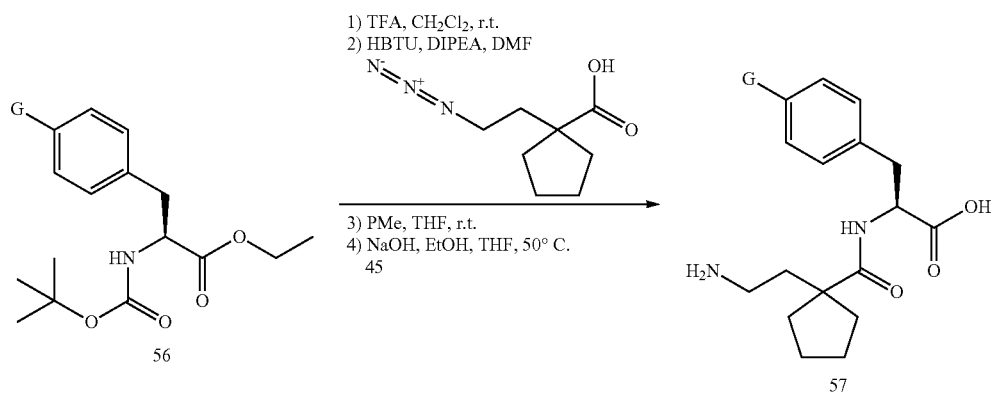

Rings represented by G other than 2,6-dichlorobenzoyl may be installed into intermediate 55 as shown in Scheme 9. Then intermediate 55 is made available for subsequent coupling in a similar manner as that shown in Scheme 7 and to produce a target molecule ready for coupling according to Scheme 4 enroute to making the compounds of formula I. Detailed synthesis methods of the preparation of intermediate 53 in Scheme 9 above are published in U.S. Pat. Nos. 6,388,084 B1 and 6,380,387 B1. Briefly, aryl or heteroaryl zinc reagents are formed from known intermediates 53 or 54 in an anhydrous solvent such as dimethyl acetamide (DMA). At this point the zinc reagents are reacted with commercially available (S)-2-tert-butoxycarbonylamino-3-(4-iodo)phenyl]propionic acid ethyl ester 55 in the presence of a palladium catalysts such as Pd(dba)$_2$ and in presence of palladium ligands tri-toluylphosphine in an aprotic solvent such as tetrahydrofuran (THF) at 50° C. In this manner, an intermediate of general structure 56 is formed. Intermediate 56 is then transformed to intermediate 57 in four steps as discussed for Scheme 7.

It is also possible to form dimeric VLA-4 antagonist targeted motifs according to a synthetic method shown in Scheme 10. In this manner, intermediate 58, which can be produced from a similar method as described above in Scheme 9, is reacted with amide forming reagents such as HBTU and base DIPEA in aprotic solvent DMF in the presence of 4-bromo-2,6-diflurobenzoic acid 52 according to scheme 10. The resulting intermediate 59 is treated with dicyano zinc in the presence of tetrakis(triphenylphosphine) palladium(0) phosphine in a solvent such as tetrahydrofuran to form the cyano substitution product, intermediate 60. Upon hydrogenation in n-propanol with hydrogen gas and catalytic palladium on carbon at room temperature, the secondary amine intermediate 63 is formed. At this point, the di-propyl ester is transformed to the di-methyl ester, followed by reaction with the acid chloride of N-Cbz-beta-alanine in the presence of base such as di-isopropylethyl amide, thereby forming intermediate 64. This intermediate is saponified with aqueous base and the N-Cbz group is removed by catalytic hydrogenolysis to yield the dimeric VLA-4 antagonist amino acid of 65 as shown in scheme 10.

Scheme 10
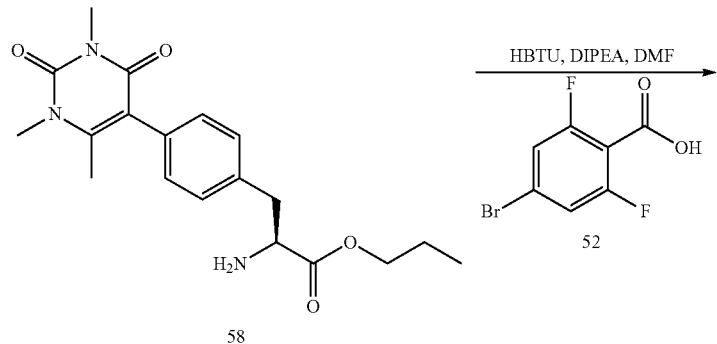
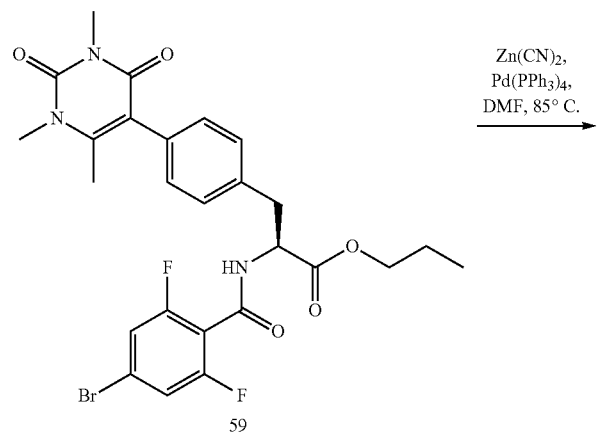
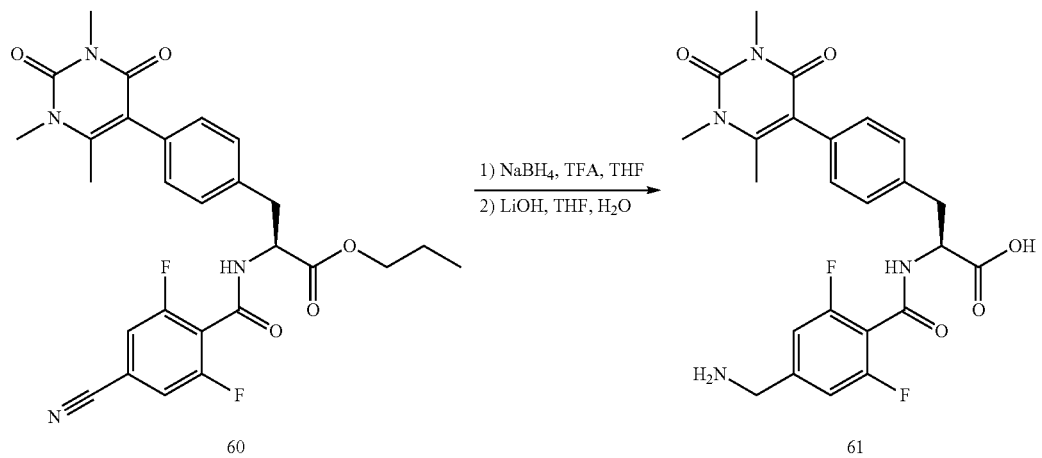

-continued
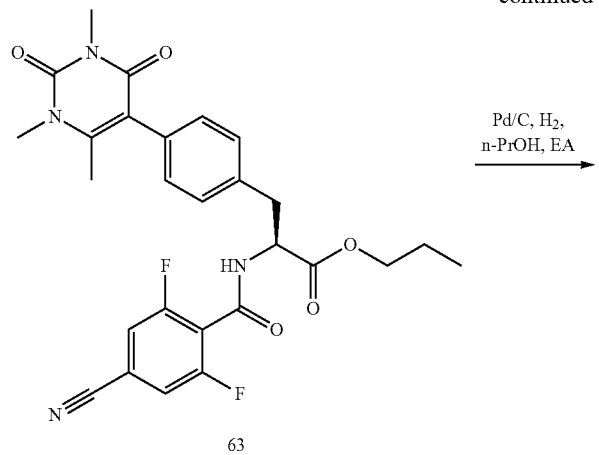
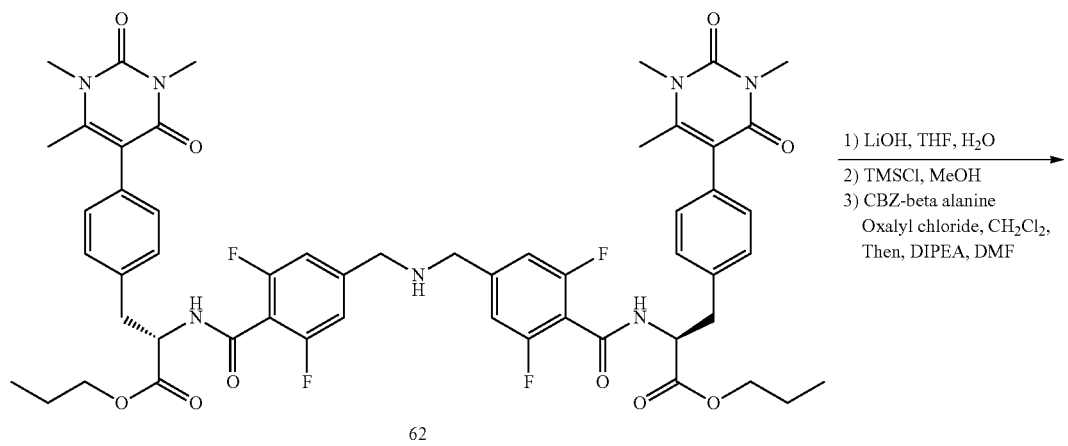
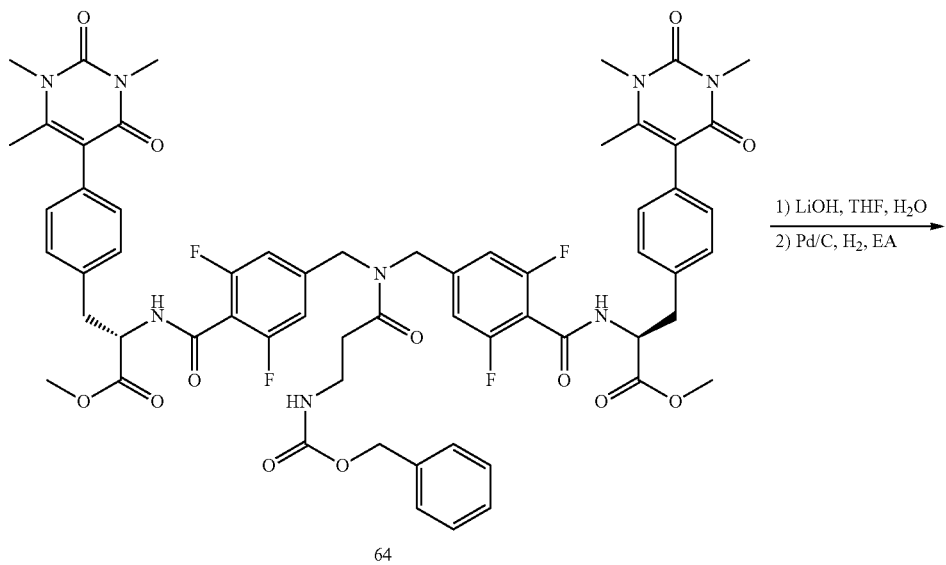

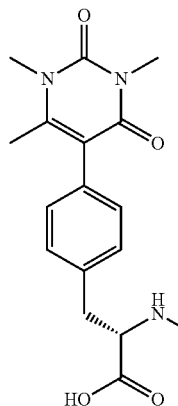
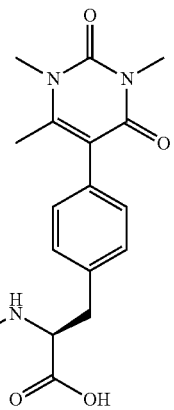

65

UTILITY

The compounds of formula I are useful in delivering conjugated moieties such as therapeutics, small molecules, peptides, nucleic acids, fluorescent moieties, and polymers to target cells expressing VLA-4 integrin receptor complexes for various therapeutic and other applications. Accordingly, the compounds of formula I may be used for treating various diseases and conditions that are associated with the expression or overexpression of VLA-4. Such diseases and conditions may include inflammation, cancer, and metabolic related diseases.

In particular embodiments, the present invention comprises a method of treating or preventing cancer in a mammal (preferably a human) in need of such treatment, wherein the method comprises administering a therapeutically effective amount of a compound of formula I. Such compositions can be administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "effective amount" of the compound to be administered will be governed by such considerations as the minimum amount necessary to treat or prevent the disease or condition (e.g. inhibit the expression of a target protein) and avoid unacceptable toxicity. For example, such amount may be below the amount that is toxic to normal cells, or the mammal as a whole. The compositions containing a compound of formula I of the invention may be administered by parenteral, intraperitoneal, and intrapulmonary administration. Parenteral infusions include intramuscular, intravenous, intraarterial, intraperitoneal, or subcutaneous administration.

EXAMPLES

The invention will be more fully understood by reference to the following examples. They should not, however, be construed as limiting the scope of the invention.

Reagents were purchased from Aldrich, Sigma, and Pierce BioScience or other suppliers as indicated below and used without further purification. The purification of multi-milligram to multi-gram scale was conducted by methods known to those skilled in the art such as elution of silica gel flash column. Preparative flash column purifications were also affected in some cases by use of disposable pre-packed multigram silica gel columns (RediSep) eluted with a CombiFlash system. Biotage™ and ISCO™ are also flash column instruments that may be used in this invention for purification of intermediates.

For the purpose of judging compound identity and purity, LC/MS (liquid chromatography/mass spectroscopy) spectra were recorded using the following system. For measurement of mass spectra, the system consists of a Micromass Platform II spectrometer: ES Ionization in positive mode (mass range: 150-1200 amu). The simultaneous chromatographic separation was achieved with the following HPLC system: ES Industries Chromegabond WR C-18 3u 120Å (3.2×30 mm) column cartridge; Mobile Phase A: Water (0.02% TFA) and Phase B: Acetonitrile (0.02% TFA); gradient 10% B to 90% B in 3 minutes; equilibration time of 1 minute; flow rate of 2 mL/minute. In some cases, ammonium acetate at 20 millimolar concentration was used as a modifier for effective ionization during preparative HPLC. In such cases, the ammonium salt was isolated.

For some separations, the use of super critical fluid chromatography may also be useful. Super critical fluid chromatography separations were performed using a Mettler-Toledo Minigram system with the following typical conditions: 100 bar, 30° C., 2.0 mL/min eluting a 12 mm AD column with 40% MeOH in super critical fluid $CO_2$. In the case of analytes with basic amino groups, 0.2% isopropyl amine was added to the methanol modifier.

Compounds were characterized either by $^1$H-NMR using a Varian Inova 400 MHz NMR Spectrometer or a Varian Mercury 300 MHz NMR Spectrometer as well as by high resolution mass spectrometry using a Bruker Apex-II high-resolution 4.7T FT-Mass Spectrometer. Final compounds were also characterized by high resolution mass spectrometry using a LTQ CL Orbitrap sold by Thermo Electron.

Abbreviations used herein are as follows:
AIBN 2,2'-azobisisobutyronitrile
Bu butyl
DCE 1,2-dichloroethane
DCM dichloromethane
DBU 1,8-diazabicyclo[5.4.0]undec-7-ene
DIAD diisopropyl azodicarboxylate
DIEA diethylamine
DIPEA diisopropylethylamine
DMF N,N-dimethylformamide DMSO dimethylsulfoxide
EDC-HCl 1-ethyl-3-(3-dimethyllaminopropyl)carbodiimide hydrochloride
EtOAc ethyl acetate
EtOH ethyl alcohol
FCC flash column chromatography
h hour
HBTU O-(benzotriazol-1-yl)-N,N,N',N'-tetramethyluroniumhexafluorophosphate
HOBt hydroxybenzotriazole
HPLC high pressure liquid chromatography
HRMS high resolution mass spectra
LRMS low resolution mass spectra
LC liquid chromatography
L-Pro L-proline
MCPBA meta-chloroperoxybenzoic acid
MeOH methyl alcohol
MW microwave
NIS N-iodosuccinimide
NBS N-bromosuccinimide
NMP 1-methyl-2-pyrrolidinone
PdCl$_2$(dppf) [1,1'-Bis(diphenylphosphino)ferrocene]dichloropalladium(II)
PEGn Polyethylene glycol repeating n times (e.g., PEG2=—OCH2CH2OCH2CH2—)
PG protecting group
PyBroP bromo-tris-pyrrolidino-phosphonium hexafluorophosphate
rt room temperature
TBAF tetrabutylammonium fluoride
TBDMS tert-butyl-dimethylsilyl
TBTU 2-(1H-benzotriazole-1-yl)-1,1,3,3-tetramethyluronium tetrafluoroborate
TMS trimethylsilyl
TEA triethylamine
TFA trifluoroacetic acid
THF tetrahydrofuran
TLC thin layer chromatography
TPP triphenylphosphine Synthesis Of Compounds Targeting VLA-4

Example 1

(S)-3-[4-(2,6-dichlorobenzoylamino)phenyl]-2-[[1-[2-[3-[2-[2-[2-[3-(2,5-dioxo-2,5-dihydropyrrol-1-yl)propionylamino]ethoxy]ethoxy]ethoxy] ethoxy] propionylamino]ethyl]cyclopentanecarbonyl]amino] propionic acid; VLA-4 Ligand Reagent 1

Step 1: Preparation of 1-(2-bromoethyl) cyclopentanecarboxylic acid methyl ester:

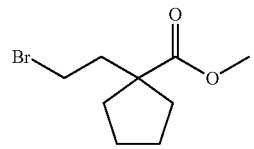

To a solution of diisopropylamine (56 mL, 396 mmol) in THF (85 mL) was added dropwise a solution of n-butyl lithium (240 mL, 393 mmol, 1.6M) in hexanes at −10° C. while maintaining the temperature below 0° C. After addition, the solution was stirred for 30 min at 0° C. To this, a solution of cyclopentanecarboxylic acid methyl ester (37.4 g, 263 mmol) in THF (50 mL) was added dropwise at −70° C. maintaining the internal temperature between −60 to −70° C. After addition, the reaction mixture was stirred for 1 h at −50 to −60° C. Then, a solution of 1,2-dibromoethane (47 mL, 545 mmol) in THF (50 mL) was added dropwise and the light brown suspension was stirred for 1 h at −70 to −60° C. Then, it was allowed to warm to room temperature and stirred overnight. The reaction mixture was poured into a saturated aqueous solution of ammonium chloride (200 mL) and the organic compound was extracted into ether (2×100 mL). The combined extracts were washed with a saturated solution of sodium chloride (150 mL) and dried over anhydrous magnesium sulfate. After filtration of the drying agent, the solution was concentrated under vacuum and the resulting residue was distilled at 95-105° C./2.5 mm Hg to obtain 49.6 g (80% yield) of 1-[2-bromoethyl]cyclopentanecarboxylic acid methyl ester as a colorless oil.

Step 2: Preparation of 1[2-azidoethyl]cyclopentanecarboxylic acid methyl ester:

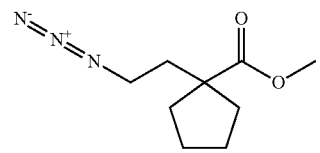

A solution of 1-[2-bromoethyl]cyclopentanecarboxylic acid methyl ester (49.6 g, 211 mmol) and sodium azide (54 g, 831 mmol) in DMF (200 mL) was stirred at 50° C. for 5 h under nitrogen atmosphere. Then, the solids were filtered and the filtrate was concentrated to near dryness. The residue

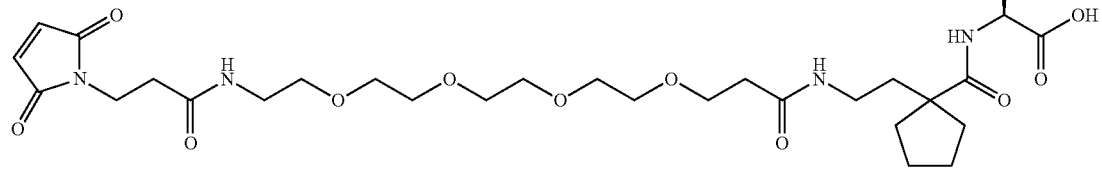

was diluted with ethyl acetate (500 mL) and the undissolved solids were collected by filtration and the filtrate was concentrated to give the crude ethyl 1-(2-azidoethyl) cyclopentanecarboxylate which was purified by chromatography over 250 g of silica gel, eluting with 5% ethyl acetate in hexane to give 36.2 g (87% yield) of 1-[2-azidoethyl]cyclopentanecarboxylic acid methyl ester as a light brown oil. EI(+)-HRMS m/e calcd. for $C_9H_{15}N_3O_2$ (M–H)⁺ 196.1086, obsd. 196.1342.

Step 3: Preparation of 1-[2-azidoethyl cyclopentanecarboxylic acid:

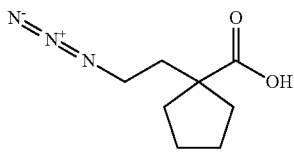 [SMILES: [N-]=[N+]=NCCC1(C(=O)O)CCCC1]

The 1-[2-azidoethyl]cyclopentanecarboxylic acid methyl ester (36.2 g, 184 mmol) was dissolved in THF (500 mL) and methanol (250 mL) and a solution of LiOH monohydrate (15.44 g, 368 mmol) in water (300 mL) was added. The resulting solution was stirred at 40° C. overnight and concentrated. The residue was dissolved in 1 L of water containing 40 mL of 1N NaOH and was washed with hexane (500 mL). The aqueous layer was acidified with 1N hydrochloric acid and the organic compound was extracted with ether (2×500 mL). The combined extracts were washed with saturated sodium chloride solution and the organic layer was dried over anhydrous $Na_2SO_4$. Filtration of the drying agent and concentration gave 32.5 g (96% yield) of 1-[2-azidoethyl cyclopentanecarboxylic acid as an amber liquid. ES(+)-HRMS m/e calcd. for $C_8H_{13}N_3O_2$ (M+Na)⁺ 206.0900, obsd. 206.0900.

Step 4: Preparation of (S)-3-[4-nitrophenyl]-2-tert-butoxycarbonylamino-propionic acid methyl ester:

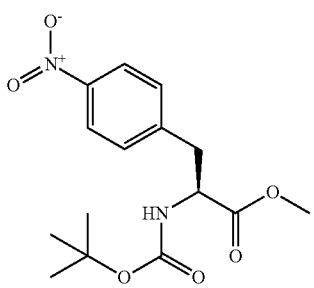 [SMILES: COC(=O)[C@H](Cc1ccc([N+](=O)[O-])cc1)NC(=O)OC(C)(C)C]

To a suspension of (S)-3-[4-nitrophenyl]-2-tert-butoxycarbonylamino-propionic acid (70.2 g, 226.2 mmol) and sodium carbonate (95 g, 1.13 mole) in DMF (500 mL) was added methyl iodide (70.4 mL, 1.13 mole) at room temperature. The suspension was stirred for 15 h at room temperature at which time TLC analysis of the mixture indicated the absence of starting material and the excess methyl iodide and some DMF were removed under high vacuum. Then, it was poured into water (2 L) and stirred at room temperature as a precipitate formed slowly over 72 h. The precipitated solids were collected by filtration and washed with water (2 L). After air and vacuum drying, 72 g (98% yield) of (S)-3-[4-nitrophenyl]-2-tert-butoxycarbonylamino-propionic acid methyl ester was isolated as a light yellow solid (mp 95-96° C.). ES(+)-HRMS m/e calcd. for $C_{15}H_{20}N_2O_6$ (M+H)⁺ 325.1400, obsd. 325.1404.

Step 5: Preparation of (S)-3-[4-aminophenyl]-2-tert-butoxycarbonylamino-propionic acid methyl ester:

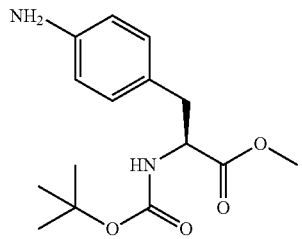 [SMILES: COC(=O)[C@H](Cc1ccc(N)cc1)NC(=O)OC(C)(C)C]

To a mixture of methyl (S)-3-[4-nitrophenyl]-2-tert-butoxycarbonylamino-propionic acid methyl ester (72 g, 222 mmol), zinc dust (~325 mesh, 145.2 g, 2.2 mole, 10 equiv.) and ammonium chloride (178.1 g, 3.3 mole, 15 equiv.) was added methanol (1 L) and water (500 mL) at room temperature. After addition of water, an exothermic reaction ensued and the internal temperature rose to 45 to 50° C. The suspension was stirred for 30 min to 1 h at room temperature, at which time TLC analysis of the mixture indicated the absence of starting material, and the reaction mixture was filtered through a pad of celite and the filtered cake was washed with methanol (1 L) and water (500 mL). Concentration to remove most of the methanol and some water afforded white solids which were collected by filtration and washed with water. After air drying, 65.5 g (100% yield) of (S)-3-[4-aminophenyl]-2-tert-butoxycarbonylamino-propionic acid methyl ester was isolated as a white solid (mp 86-89° C.). ES(+)-HRMS m/e calcd. for $C_{15}H_{22}N_2O_4$ (M+H)⁺ 294.1621, obsd. 294.1614.

Step 6: Preparation of (S)-2-tert-butoxycarbonylamino-3-[4-(2,6-dichlorobenzoylamino)phenyl]propionic acid methyl ester:

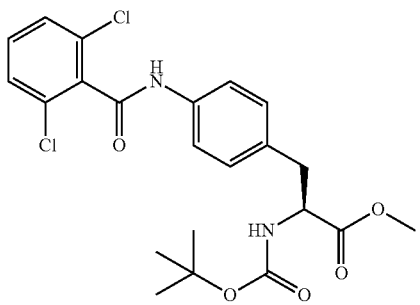 [SMILES: COC(=O)[C@H](Cc1ccc(NC(=O)c2c(Cl)cccc2Cl)cc1)NC(=O)OC(C)(C)C]

To a solution of (S)-3-[4-aminophenyl]-2-tert-butoxycarbonylamino-propionic acid methyl ester (37.57 g, 127.6 mmol) and 2,6-dichlorobenzoyl chloride (29.45 g, 140.6 mmol) in dichloromethane (350 mL) was added DIPEA (24.8 g, 192 mmol) at room temperature. The brown solution was stirred for 15 h at room temperature to afford a white suspension at this time TLC analysis of the mixture indicated the absence of starting material. Then, the solids were collected by filtration and the solids were washed with dichloromethane (150 mL) and air dried to obtain 52.75 g (88.4% yield) of (S)-2-tert-butoxycarbonylamino-3-[4-(2,6-dichlorobenzoylamino)phenyl]propionic acid methyl ester as a white solid: mp 192-194° C. ES(+)-HRMS m/e calcd. for $C_{22}H_{24}Cl_2N_2O_5$ (M+H)⁺ 466.1062, obsd. 466.1069.

Step 7: Preparation of (S)-2-amino-3-[4-(2,6-dichlorobenzoylamino)phenyl]propionic acid methyl ester hydrochloride salt:

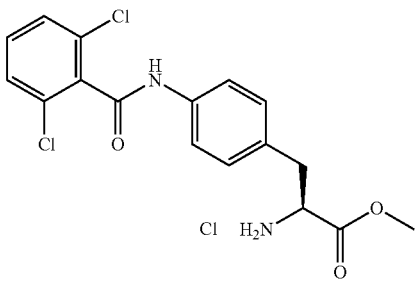 [SMILES: COC(=O)[C@@H](N)Cc1ccc(NC(=O)c2c(Cl)cccc2Cl)cc1 ; Cl]

The solid (S)-2-tert-butoxycarbonylamino-3-[4-(2,6-dichlorobenzoylamino)phenyl]propionic acid methyl ester (43.45 g, 92.97 mmol) in dioxane (90 mL) was treated with 166 mL of 4.0N hydrochloric acid in dioxane at room temperature. After 5 minutes, the solids went into solution and the mixture was stirred for 2 h. Then, some of the dioxane was removed under vacuum to afford a yellow syrup and 250 mL of ethyl ether was added. A gum was formed which was dissolved in THF (100 mL) and methanol (100 mL). The solvent was removed under vacuum to obtain 43.7 g (100% yield) of (S)-2-amino-3-[4-(2,6-dichlorobenzoylamino)phenyl]propionic acid methyl ester hydrochloride salt as a white solid: mp 180-195° C. This was stored in the refrigerator under argon atmosphere. ES(+)-HRMS m/e calcd. for $C_{17}H_{16}Cl_2N_2O_3$ $(M+H)^+$ 367.0616, obsd. 367.0611.

Step 8: Preparation of (S)-2-[[1-(2-azidoethyl)cyclopentanecarbonyl]amino]-3-[4-(2,6-dichlorobenzoylamino)phenyl]propionic acid methyl ester:

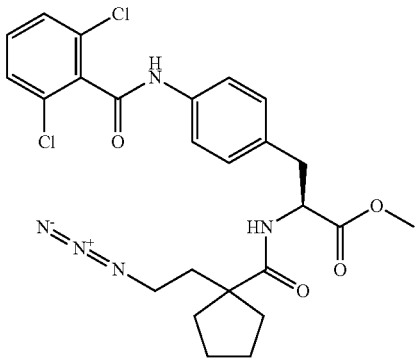 [SMILES: COC(=O)[C@H](Cc1ccc(NC(=O)c2c(Cl)cccc2Cl)cc1)NC(=O)C1(CCN=[N+]=[N-])CCCC1]

To a solution of (S)-2-amino-3-[4-(2,6-dichlorobenzoylamino)phenyl]propionic acid methyl ester hydrochloride salt (10 g, 24.79 mmol) and 1-[2-azidoethyl]cyclopentanecarboxylic acid methyl ester (5.0 g, 27.29 mmol) in DMF (100 mL) were added HBTU (10.37 g, 27.33 mmol) and DIPEA (8.82 g, 68.3 mmol) at room temperature. The clear solution was stirred for 48 h at room temperature and water was added (~200 mL) to the reaction mixture to precipitate the product. The solid was collected by filtration and washed with water (100 mL) and hexane (~100 mL). After drying at air, 11.2 g of the product was obtained as a light brick solid which was treated with acetonitrile (100 mL) under hot conditions. All impurities went into acetonitrile and the solid was collected by filtration to afford 8.24 g of coupling product. The acetonitrile solution was removed under vacuum and the residue was dissolved in ethyl acetate and the product was precipitated by the addition of hexane. Again, the solid was collected by filtration and the solids were dried at air to obtain another 2.03 g (78% total yield) of (S)-2-[[1-(2-azidoethyl)cyclopentanecarbonyl]amino]-3-[4-(2,6-dichlorobenzoylamino)phenyl]propionic acid methyl ester as a white solid. ES(+)-HRMS m/e calcd. for $C_{25}H_{27}Cl_2N_5O_4$ $(M+Na)^+$ 554.1332, obsd. 554.1334.

Step 9: Preparation of (S)-2-[[1-(2-azidoethyl)cyclopentanecarbonyl]amino]-3-[4-(2,6-dichlorobenzoylamino)phenyl]propionic acid:

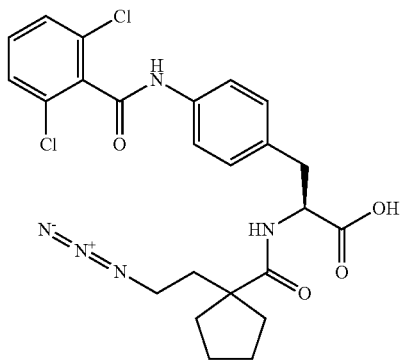 [SMILES: [N-]=[N+]=NCCC1(C(=O)N[C@@H](Cc2ccc(NC(=O)c3c(Cl)cccc3Cl)cc2)C(=O)O)CCCC1]

To a suspension of (S)-2-[[1-(2-azidoethyl)cyclopentanecarbonyl]amino]-3-[4-(2,6-dichlorobenzoylamino)phenyl] propionic acid methyl ester (14.77 g, 27.7 mmol) in THF (200 mL) and ethanol (200 mL) was added aqueous 1.0N sodium hydroxide (150 mL) at room temperature. The mixture was stirred for 15 h at room temperature at which time TLC analysis of the mixture indicated the absence of starting material. Then, it was diluted with water (20 mL) and the THF and ethanol were removed by rotary evaporation and diluted with 100 mL of water and extracted with ether (200 mL) to remove any neutral impurities. The aqueous layer was neutralized with 1N HCl and the resulting white solids were collected by filtration and washed with water and hexanes. After air-drying, 13.37 g (93% yield) of (S)-2-[[1-(2-azidoethyl)cyclopentanecarbonyl]amino]-3-[4-(2,6-dichlorobenzoylamino)phenyl]propionic acid was obtained as a white solid. ES(+)-HRMS m/e calcd. for $C_{24}H_{25}Cl_2N_5O_4$ $(M+Na)^+$ 540.1176, obsd. 540.1177.

Step 10: Preparation of (S)-2-[[1-(2-aminoethyl)cyclopentanecarbonyl]amino]-3-[4-(2,6-dichlorobenzoylamino) phenyl]propionic acid;

VLA-4 Ligand—1

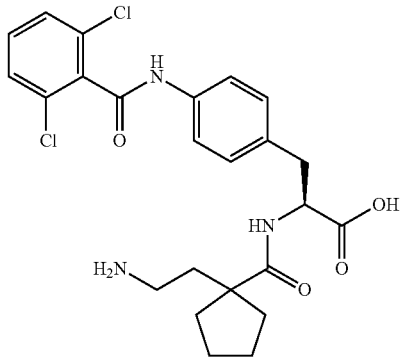 [SMILES: NCCC1(C(=O)N[C@@H](Cc2ccc(NC(=O)c3c(Cl)cccc3Cl)cc2)C(=O)O)CCCC1]

To a solution of (S)-2-[[1-(2-azidoethyl)cyclopentanecarbonyl]amino]-3-[4-(2,6-dichlorobenzoylamino)phenyl]propionic acid (6.28 g, 12.11 mmol) in THF (91 mL) was added a solution of trimethylphosphine in THF (48.5 mL, 48.46 mmol, 1.0M) at 0° C. It was a clear solution in the beginning and after 30 min some precipitate was formed and this mixture was stirred for overnight at which time TLC analysis of the mixture indicated the absence of starting material. Then, 10 equiv. of water (120 mmol, 2.16 mL) was added and the mixture was stirred for 2 h at room temperature. The solvent was removed under vacuum and the residue was azeotrophed two times with toluene to give a pasty material which was purified using HPLC to obtain 4.57 g (77% yield) of (S)-2-[[1-(2-aminoethyl)cyclopentanecarbonyl]amino]-3-[4-(2,6-dichlorobenzoylamino)phenyl]propionic acid as an amorphous white solid. ES(+)-HRMS m/e calcd. for $C_{24}H_{27}Cl_2N_3O_4$ (M+H)$^+$ 492.1452, obsd. 492.1451.

Step 11: Preparation of (S)-3-[4-(2,6-dichlorobenzoylamino)phenyl]-2-[[1-[2-[3-[2-[2-[2-[2-[3-(2,5-dioxo-2,5-dihydropyrrol-1-yl)propionylamino]ethoxy]ethoxy]ethoxy]ethoxy]propionylamino]ethyl]cyclopentanecarbonyl]amino]propionic acid; VLA-4 Ligand Reagent 1):

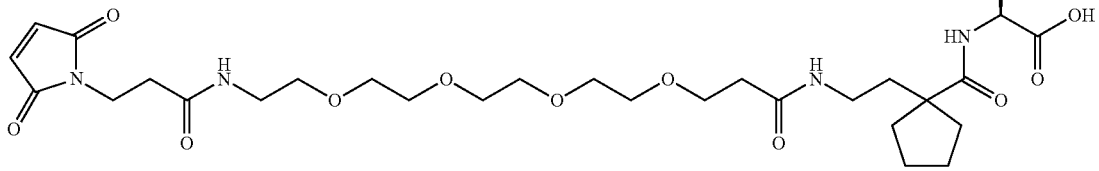

To a solution of (S)-2-[[1-(2-aminoethyl)cyclopentanecarbonyl]amino]3-[4-(2,6-dichlorobenzoylamino)phenyl] propionic acid (191.5 mg, 0.39 mmol) and 3-[2-[2-[2-[[3-(2,5-dioxo-2,5-dihydro-pyrrol-1-yl)-propionylamino]-ethoxy]ethoxy]ethoxy]ethoxy]propionic acid-2,5-dioxo-pyrrolidin-1-yl ester (200 mg, 0.39 mmol) in DMSO (2 mL) was added an excess of DIPEA (151 mg, 203 uL, 1.17 mmol) at room temperature under nitrogen atmosphere. The resulting light yellow solution was stirred for 1 h at which time LCMS analysis indicated the absence of starting material. Then, the excess DIPEA was removed under vacuum and the desired product was isolated by purification using an HPLC method to obtain 90 mg (26% yield) of (S)-3-[4-(2,6-dichlorobenzoylamino)phenyl]-2-[[1-[2-[3-[2-[2-[2-[2-[3-(2,5-dioxo-2,5-dihydropyrrol-1-yl)propionylamino]ethoxy]ethoxy]ethoxy]ethoxy]propionylamino]ethyl]cyclopentanecarbonyl]amino]propionic acid as a white solid. ES(+)-HRMS m/e calcd. for $C_{42}H_{53}Cl_2N_5O_{12}$ (M+H)$^+$ 890.3141, obsd. 890.3140.

Example 2

Preparation of (S)-3-[4-(2,6-dichlorobenzoylamino)phenyl]-2-[[[1-[2-[3-[2-[2-[2-[2-[2-[2-[2-[3-(2,5-dioxo-2,5-dihydropyrrol-1-yl)propionylamino]-ethoxy]ethoxy]ethoxy]ethoxy]ethoxy]ethoxy]ethoxy]ethoxy]propionylamino]ethyl]cyclopentyl]carbonyl]amino]propionic acid; VLA-4 Ligand Reagent 2

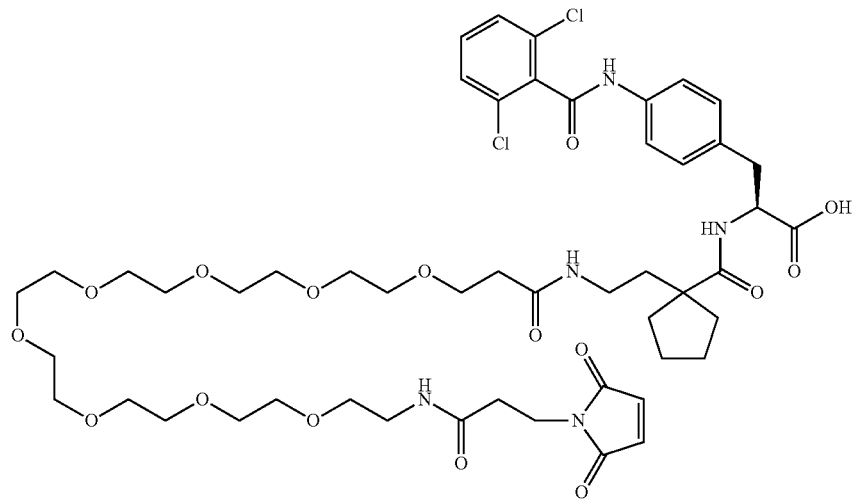 [SMILES: O=C(CCOCCOCCOCCOCCOCCOCCOCCOCCNC(=O)CCN1C(=O)C=CC1=O)NCCC1(C(=O)N[C@@H](Cc2ccc(NC(=O)c3c(Cl)cccc3Cl)cc2)C(=O)O)CCCC1]

The title compound was prepared using a similar procedure as described in Example 1, Step 11, starting from (S)-2-[[1-(2-aminoethyl)cyclopentanecarbonyl]amino]-3-[4-(2,6-dichlorobenzoylamino)phenyl]propionic acid (607 mg, 1.0 mmol), 3-[2-[2-[2-[2-[2-[2-[2-[2-[3-(2,5-dioxo-2,5-dihydro-pyrrol-1-yl)propionylamino]-ethoxy]ethoxy]ethoxy]ethoxy]ethoxy]ethoxy]ethoxy]ethoxy]propionic acid-2,5-dioxo-pyrrolidin-1-yl ester (689 mg, 1.0 mmol), and DIPEA (388 mg, 522 uL, 3.0 mmol), and after HPLC purification, resulted in a light yellow solid (788 mg, 74%). ES(+)-HRMS m/e calcd. for $C_{50}H_{69}Cl_2N_5O_{16}$ (M+H)$^+$ 1066.4189, obsd. 1066.4182.

Example 3

Preparation of (S)-3-[4-(2,6-dichlorobenzoylamino)phenyl]-2-[[1-[2-[3-[2-[2-[2-[2-[2-[2-[2-[2-[2-[2-[3-(2,5-dioxo-2,5-dihydropyrrol-1-yl)propionylamino]-ethoxy]ethoxy]ethoxy]ethoxy]ethoxy]ethoxy]ethoxy]ethoxy]ethoxy]ethoxy]propionylamino]ethyl]cyclopentanecarbonyl]amino]propionic acid; VLA-4 Ligand Reagent 3

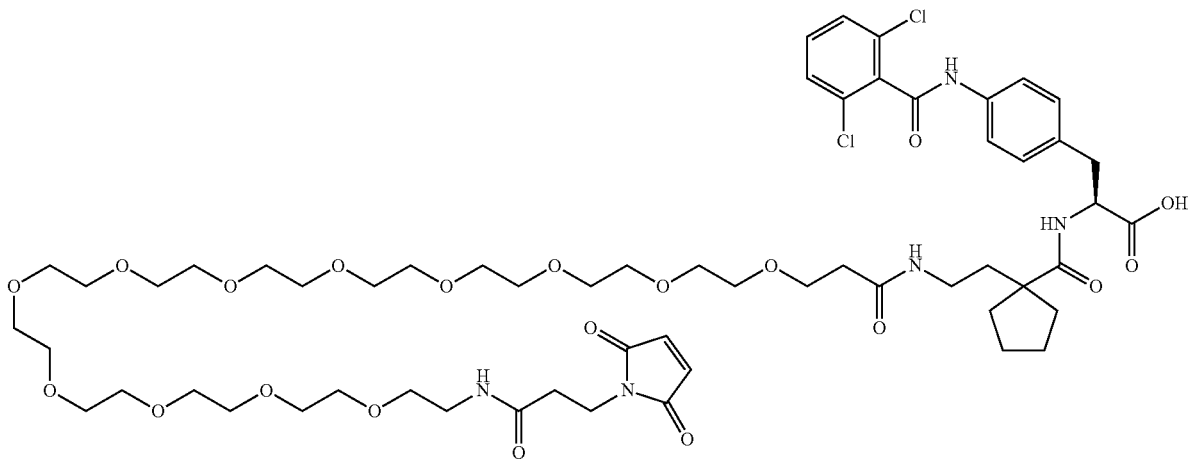 [SMILES: O=C(CCOCCOCCOCCOCCOCCOCCOCCOCCOCCOCCOCCOCCNC(=O)CCN1C(=O)C=CC1=O)NCCC1(C(=O)N[C@@H](Cc2ccc(NC(=O)c3c(Cl)cccc3Cl)cc2)C(=O)O)CCCC1]

The title compound was prepared using a similar procedure as described in Example 1, Step 11, starting from (S)-2-[[1-(2-aminoethyl)cyclopentanecarbonyl]amino]-3-[4-(2,6-dichlorobenzoylamino)phenyl]propionic acid (100 mg, 0.2 mmol), 3-[2-[2-[2-[2-[2-[2-[2-[2-[2-[2-[2-[2-[3-(2,5-dioxo-2,5-dihydro-pyrrol-1-yl)propionylamino]-ethoxy]ethoxy]ethoxy]ethoxy]ethoxy]ethoxy]ethoxy]ethoxy]ethoxy]ethoxy]ethoxy]propionic acid-2,5-dioxo-pyrrolidin-1-yl ester (176 mg, 0.2 mmol), and DIPEA (258 mg, 191 uL, 2.0 mmol), and after HPLC purification, resulted in a white solid (28 mg, 11%). ES(+)-HRMS m/e calcd. for $C_{58}H_{85}Cl_2N_5O_{20}$ (M+H)$^+$ 1242.5238, obsd. 1242.5248.

Example 4

Preparation of (S)-2-[[1-[2-[3-[2-]2-[2-[2-[2-[2-[2-(2-acetylsulfanyl-ethoxy)ethoxy]ethoxy]ethoxy]ethoxy]ethoxy]ethoxy]propionylamino]-ethyl]-cyclopentanecarbony]-amino]-3-[4-(2,6-dichlorobenzoylamino)phenyl]propionic acid;

VLA-4 Ligand Reagent 4

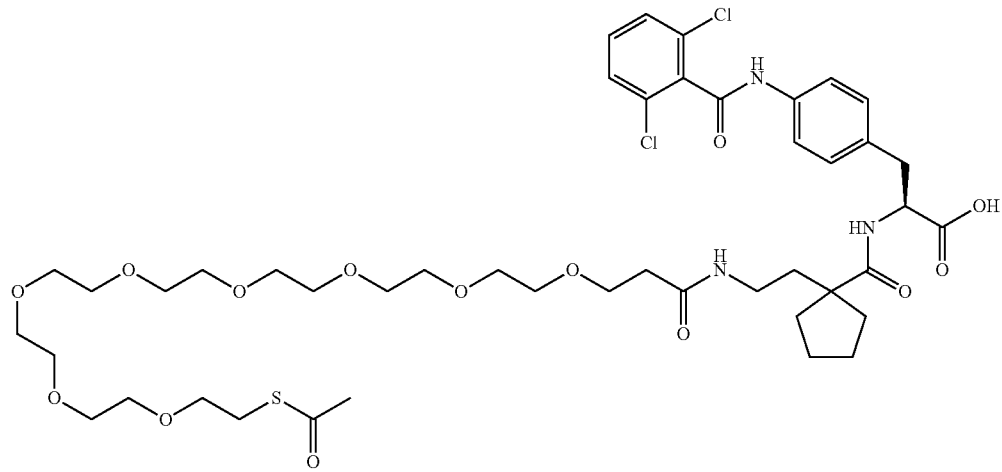 [SMILES: CC(=O)SCCOCCOCCOCCOCCOCCOCCOCCOCCC(=O)NCCC1(C(=O)N[C@@H](Cc2ccc(NC(=O)c3c(Cl)cccc3Cl)cc2)C(=O)O)CCCC1]

The title compound was prepared using a similar procedure as described in Example 1, Step 11, starting from (S)-2-[[1-(2-aminoethyl)cyclopentanecarbonyl]amino]-3-[4-(2,6-dichlorobenzoylamino)phenyl]propionic acid (194 mg, 0.32 mmol), 3-[2-[2-[2-[2-[2-[2-[2-(2-acetylsulfanyl-ethoxy)ethoxy]ethoxy]ethoxy]ethoxy]ethoxy]ethoxy]propionic acid-2,5-dioxo-pyrrolidin-1-yl ester (190 mg, 0.32 mmol), and DIPEA (124 mg, 167 uL, 0.96 mmol), and after HPLC purification, resulted in a yellow viscous oil (220 mg, 70%). ES(+)-HRMS m/e calcd. for $C_{45}H_{65}Cl_2N_3O_{14}S$ (M+H)$^+$ 974.3637, obsd. 974.3631.

Example 5
(S)-3-[4-(2,6-dichlorobenzoylamino)phenyl]-2-[2,6-dichloro-4-[3-[3-[2-[2-[2-[2-[3-(2,5-dioxo-2,5-dihydropyrrol-1-yl)propionylamino]ethoxy]ethoxy]ethoxy]ethoxy]propionylamino]propoxy]benzoylamino]propionic acid; VLA-4 Ligand Reagent 5
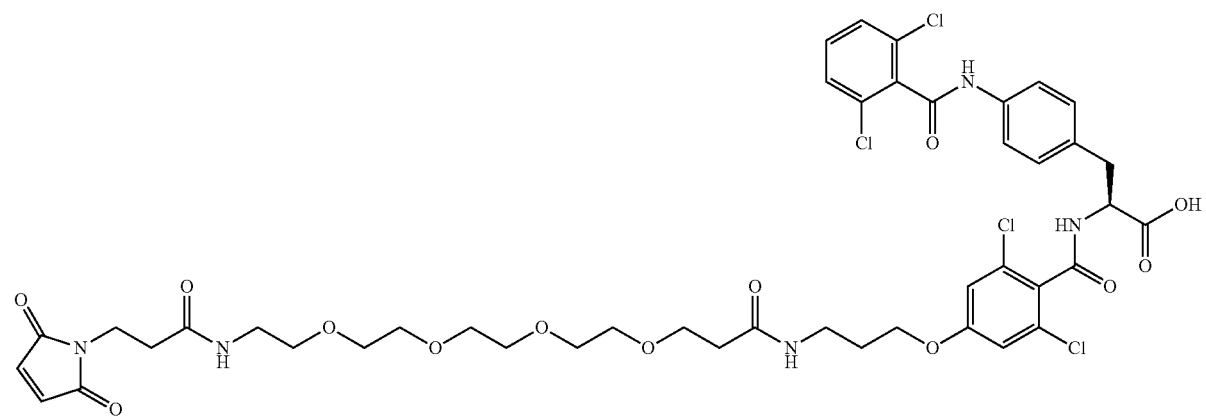 [SMILES: O=C(CCOCCOCCOCCOCCNC(=O)CCN1C(=O)C=CC1=O)NCCCOc1cc(Cl)c(C(=O)N[C@@H](Cc2ccc(NC(=O)c3c(Cl)cccc3Cl)cc2)C(=O)O)c(Cl)c1]

Step 1: Preparation of (3,5-dichlorophenoxy)-triisopropylsilane

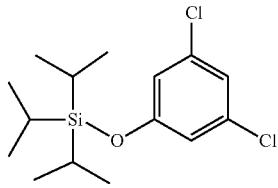 [SMILES: CC(C)[Si](Oc1cc(Cl)cc(Cl)c1)(C(C)C)C(C)C]

To a mixture of 3,5-dichlorophenol (16.3 g, 100 mmol), imidazole (14.98 g, 220 mmol), and triisopropylchlorosilane (21.21 g, 110 mmol) was added DMF (200 mL) at room temperature. The resulting brown solution was stirred for 15 h and then it was diluted with water (500 mL). The organic compound was extracted into ethyl acetate (2×100 mL) and the combined organic layer was washed with brine solution and dried over anhydrous MgSO$_4$. Filtration and concentration gave the crude residue which was purified using an ISCO (400 g) column chromatography to obtain 31.1 g (97%) of (3,5-dichlorophenoxy)-triisopropylsilane as a colorless oil. EI(+)-HRMS m/e calcd. for $C_{15}H_{24}Cl_2OSi$ (M)$^+$ 318.0973, obsd. 318.0971.

Step 2: Preparation of 2,6-dichloro-4-triisopropylsilanyloxy-benzoic acid:

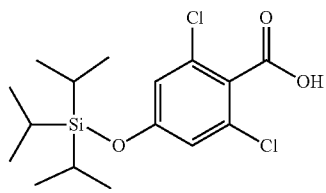 [SMILES: CC(C)[Si](Oc1cc(Cl)c(C(=O)O)c(Cl)c1)(C(C)C)C(C)C]

To a THF (110 mL) solution were added a solution of n-butyllithium (28 mL, 70 mmol, 2.5M) in hexanes and tetramethylethylenediamine (8.42 g, 10.94 mL, 72.45 mmol) at −78° C. The resulting light yellow solution was stirred for 30 minutes at this temperature and then a solution of (3,5-dichlorophenoxy)-triisopropylsilane (15.97 g, 50 mmol) in THF (20 mL) was added drop-wise for 30 minutes. The resulting light yellow solution was stirred for 3 h and then carbon dioxide gas was bubbled through the reaction mixture. During CO$_2$ bubbling, the color of the reaction mixture changed from a brown to light yellow solution within 10 minutes and the bubbling was continued for 1 h at −75 and then allowed to warm to room temperature in 30 minutes with continuous CO$_2$ bubbling. Then, it was poured into 1N HCl and the organic compound was extracted into dichloromethane (2×150 mL). The combined organic layer was washed with brine solution and dried over anhydrous MgSO$_4$. Filtration and concentration gave the crude residue which was purified using an ISCO (400 g) column chromatography to obtain 7.02 g (39%) of 2,6-dichloro-4-triisopropylsilanyloxy-benzoic acid as a white solid. ES(+)-HRMS m/e calcd. for $C_{16}H_{24}Cl_2O_3Si$ (M+H)$^+$ 363.0945, obsd. 363.0944.

Step 3: Preparation of (S)-3-[4-(2,6-dichlorobenzoylamino)phenyl]-2-(2,6-dichloro-4-triisopropylsilanyloxy-benzoylamino)propionic acid methyl ester:

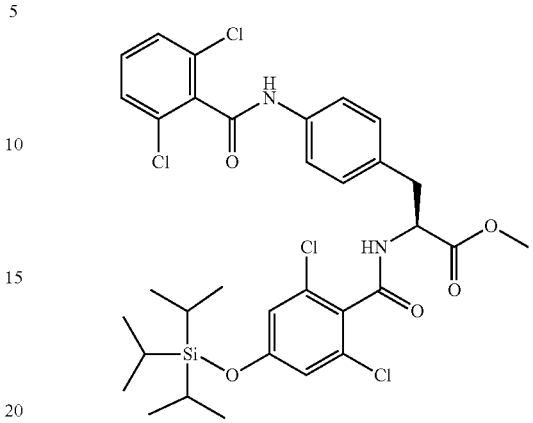

To a solution of 2,6-dichloro-4-triisopropylsilanyloxy-benzoic acid (3.63 g, 10 mmol) in toluene (50 mL) was added an excess of thionyl chloride (11.89 g, 7.2 mL, 100 mmol) at room temperature. The resulting colorless solution was heated to reflux for 5 h and then it was cooled to room temperature and the solvent and excess thionyl chloride was removed under vacuum. The resulting residue was azeotrophed one time with toluene. Then, the above 2,6-dichloro-4-triisopropylsilanyloxy-benzoic acid chloride was dissolved in dichloromethane (50 mL) and the solid (S)-2-amino-3-[4-(2,6-dichlorobenzoylamino)phenyl]propionic acid methyl ester hydrochloride salt (4.1 g, 10 mmol) and DIPEA (3.87 g, 5.26 mL, 30 mmol) were added at room temperature. The resulting solution was stirred for 15 h at room temperature and water was added (~200 mL) to the reaction mixture. Then, the organic compound was extracted into dichloromethane (2×150 mL). The combined organic layer was washed with brine solution and dried over anhydrous MgSO$_4$. Filtration and concentration gave the crude residue which was purified using an ISCO (120 g) column chromatography to obtain 6.48 g (95%) of (S)-3-[4-(2,6-dichlorobenzoylamino)phenyl]-2-(2,6-dichloro-4-triisopropylsilanyloxy-benzoylamino)propionic acid methyl ester as a white solid. ES(+)-HRMS m/e calcd. for $C_{33}H_{38}Cl_4N_2O_5Si$ (M+H)$^+$ 711.1377, obsd. 711.1377.

Step 4: Preparation of (S)-3-[4-(2,6-dichlorobenzoylamino)phenyl]-2-(2,6-dichloro-4-hydroxy-benzoylamino)propionic acid methyl ester:

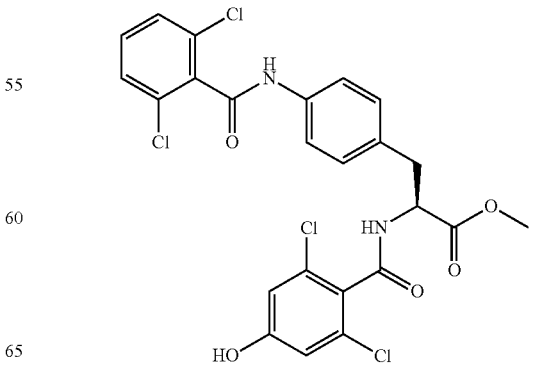

To a solution of (S)-3-[4-(2,6-dichlorobenzoylamino)phenyl]-2-(2,6-dichloro-4-triisopropylsilanyloxy-benzoylamino)propionic acid methyl ester (6.76 g, 9.48 mmol) in THF (150 mL) was added a solution of TBAF (14.22 mL, 14.22 mmol, 1M) in THF at 0° C. The resulting solution was slowly warmed to room temperature and stirred for 15 h. Then, the reaction mixture was diluted with water and the organic compound was extracted into ethyl acetate (2×150 mL). The combined organic layer was washed with brine solution and dried over anhydrous MgSO$_4$. Filtration and concentration gave the crude residue which was dissolved in ethyl acetate in hot conditions and then diluted with hexanes. The resulting solids were collected by filtration and washed with hexanes. After drying in air, 5.23 g (99%) of (S)-3-[4-(2,6-dichlorobenzoylamino)phenyl]-2-(2,6-dichloro-4-hydroxy-benzoylamino)propionic acid methyl ester was obtained as a white solid. ES(+)-HRMS m/e calcd. for $C_{24}H_{18}Cl_4N_2O_5$ (M−H)⁻ 552.9897, obsd. 552.9897.

Step 5: Preparation of (S)-2-[4-(3-tert-butoxycarbonylaminopropoxy)-2,6-dichlorobenzoylamino]-3-[4-(2,6-dichlorobenzoylamino)phenyl]propionic acid methyl ester:

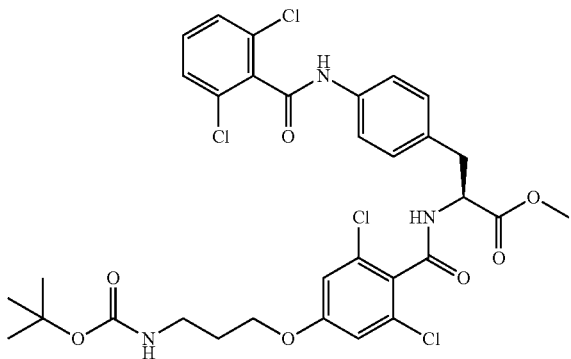 [SMILES: COC(=O)[C@H](Cc1ccc(NC(=O)c2c(Cl)cccc2Cl)cc1)NC(=O)c1c(Cl)cc(OCCCNC(=O)OC(C)(C)C)cc1Cl]

To a mixture of (S)-3-[4-(2,6-dichlorobenzoylamino)phenyl]-2-(2,6-dichloro-4-hydroxy-benzoylamino)propionic acid methyl ester (5.05 g, 9.07 mmol), 3-tert-butoxycarbonylaminopropyl bromide (2.59 g, 10.89 mmol), and potassium carbonate (3.77 g, 27.29 mmol) were added DMF (66 mL) and acetone (132 mL) at room temperature. Then, the resulting suspension was heated to reflux for 15 h at which time TLC analysis indicated the absence of starting material. Then, the reaction mixture was cooled to room temperature and diluted with water and the organic compound was extracted into ethyl acetate (2×150 mL). The combined organic layer was washed with brine solution and dried over anhydrous MgSO$_4$. Filtration and concentration gave the crude residue which was purified by ISCO (150 g) column chromatography to obtain 5.75 g (89%) of (S)-2-[4-(3-tert-butoxycarbonylaminopropoxy)-2,6-dichlorobenzoylamino]-3-[4-(2,6-dichlorobenzoylamino)phenyl]propionic acid methyl ester as a white solid. ES(+)-HRMS m/e calcd. for $C_{32}H_{33}Cl_4N_3O_7$ (M+Na)⁺ 734.0965, obsd. 734.0961.

Step 6: Preparation of (S)-2-[4-(3-aminopropoxy)-2,6-dichlorobenzoylamino]-3-[4-(2,6-dichlorobenzoylamino)phenyl]propionic acid methyl ester:

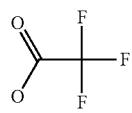

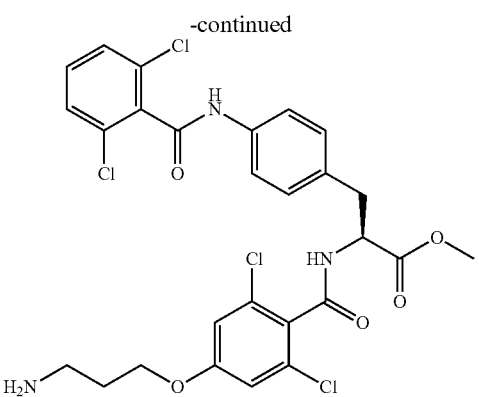

To a solution of (S)-2-[4-(3-tert-butoxycarbonylaminopropoxy)-2,6-dichlorobenzoylamino]-3-[4-(2,6-dichlorobenzoylamino)phenyl]propionic acid methyl ester (7.5 g, 7.98 mmol) in dichloromethane (100 mL) was added an excess of TFA (9.12 g, 5.9 mL, 80 mmol) at room temperature. The resulting solution was stirred for 15 h. Then, the solvent was removed under vacuum and the residue was azeotrophed one time with toluene. After drying under high vacuum, 5.8 g (99%) of (S)-2-[4-(3-aminopropoxy)-2,6-dichlorobenzoylamino]-3-[4-(2,6-dichlorobenzoylamino)phenyl]propionic acid methyl ester was obtained as a white solid. ES(+)-HRMS m/e calcd. for $C_{27}H_{25}Cl_4N_3O_5$ (M+H)⁺ 612.0621, obsd. 612.0619.

Step 7: Preparation of (S)-2-[4-(3-aminopropoxy)-2,6-dichlorobenzoylamino]-3-[4-(2,6-dichlorobenzoylamino)phenyl]propionic acid; VLA-4 Ligand 2:

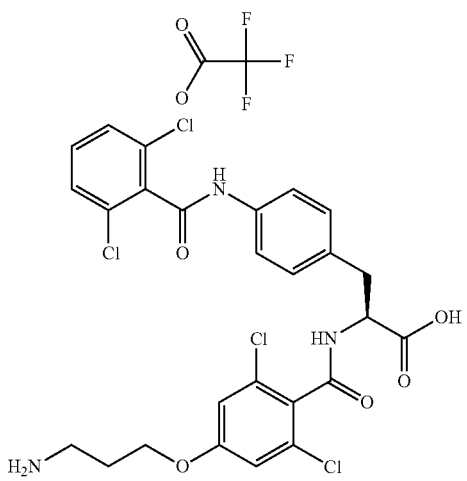

To a solution of (S)-2-[4-(3-aminopropoxy)-2,6-dichlorobenzoylamino]-3-[4-(2,6-dichlorobenzoylamino)phenyl]propionic acid methyl ester (5.8 g, 7.98 mmol,) in THF (200 mL) was added a solution of lithium hydroxide (2.4 g, 100 mmol) in water (30 mL) at room temperature. The mixture was stirred for 15 h at room temperature at which time TLC analysis of the mixture indicated the absence of starting material. Then, the solvent was removed by rotary evaporation and the residue was purified by an HPLC method to obtain 3.7 g (65% yield) of (S)-2-[4-(3-aminopropoxy)-2,6-dichlorobenzoylamino]-3-[4-(2,6-dichlorobenzoylamino)phenyl]propionic acid as a white solid. ES(+)-HRMS m/e calcd. for $C_{26}H_{23}Cl_4N_3O_5$ $(M+H)^+$ 598.0465, obsd. 598.0465.

Step 8: Preparation of (S)-3-[4-(2,6-dichlorobenzoylamino)phenyl]-2-[2,6-dichloro-4-[3-[3-[2-[2-[2-[2-[3-(2,5-dioxo-2,5-dihydropyrrol-1-yl)propionylamino]ethoxy]ethoxy]ethoxy]ethoxy]propionylamino]propoxy]benzoylamino]propionic acid; VLA-4 Ligand Reagent 5:

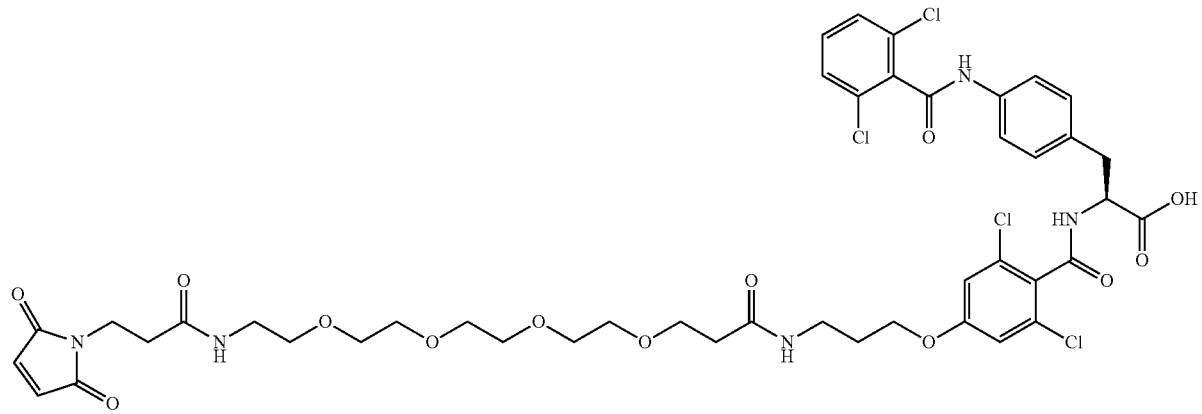 [SMILES: O=C(CCOCCOCCOCCOCCNC(=O)CCN1C(=O)C=CC1=O)NCCCOc1cc(Cl)c(C(=O)N[C@@H](Cc2ccc(NC(=O)c3c(Cl)cccc3Cl)cc2)C(=O)O)c(Cl)c1]

The title compound was prepared using a similar procedure as described in Example 1, Step 11, starting from (S)-2-[4-(3-aminopropoxy)-2,6-dichlorobenzoylamino]-3-[4-(2,6-dichlorobenzoylamino)phenyl]propionic acid (214 mg, 0.3 mmol), 3-[2-[2-[2-[[3-(2,5-dioxo-2,5-dihydro-pyrrol-1-yl)-propionylamino]-ethoxy]ethoxy]ethoxy]propionic acid-2,5-dioxo-pyrrolidin-1-yl ester (154 mg, 0.3 mmol), and DIPEA (388 mg, 522 uL, 3.0 mmol), and after HPLC purification, resulted in a white solid (52 mg, 17%).

ES(+)-HRMS m/e calcd. for $C_{44}H_{49}Cl_4N_5O_{13}$ $(M+Na)^+$ 1018.1973, obsd. 1018.1965.

Example 6

(S)-3-[4-(2,6-dichlorobenzoylamino)phenyl]-2-[2,6-dichloro-4-[3-[3-[2-[2-[2-[2-[2-[2-[2-[3-(2,5-dioxo-2,5-dihydropyrrol-1-yl)propionylamino]ethoxy]ethoxy]ethoxy]ethoxy]ethoxy]ethoxy]ethoxy]propionylamino]propoxy]benzoylamino]propionic acid; VLA-4 Ligand Reagent 6

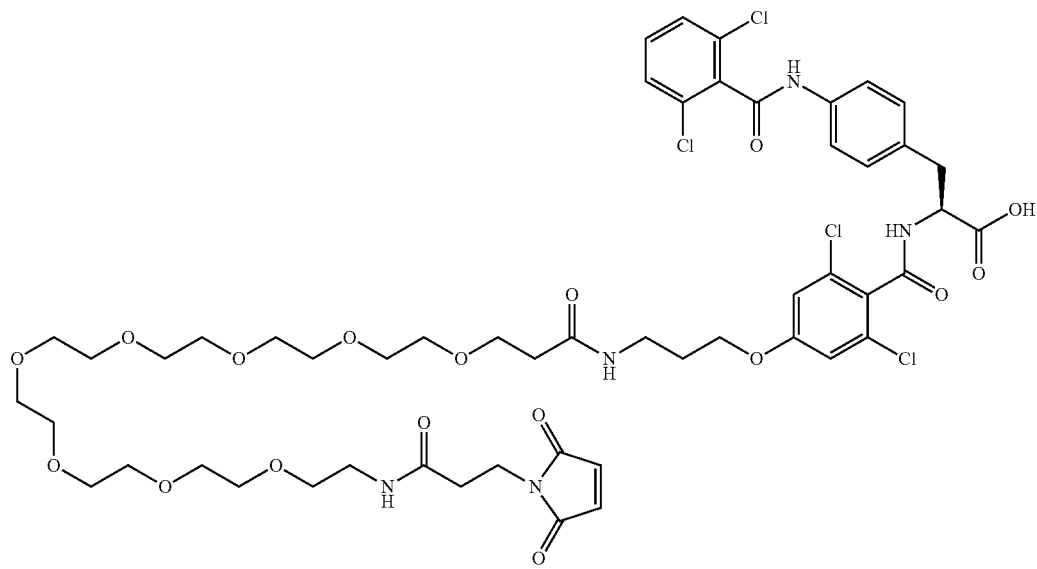 [SMILES: O=C(CCOCCOCCOCCOCCOCCOCCOCCOCCNC(=O)CCN1C(=O)C=CC1=O)NCCCOc1cc(Cl)c(C(=O)N[C@@H](Cc2ccc(NC(=O)c3c(Cl)cccc3Cl)cc2)C(=O)O)c(Cl)c1]

The title compound was prepared using a similar procedure as described in Example 1, Step 11, starting from (S)-2-[4-(3-aminopropoxy)-2,6-dichlorobenzoylamino]-3-[4-(2,6-dichlorobenzoylamino)phenyl]propionic acid (107 mg, 0.15 mmol), 3-[2-[2-[2-[2-[2-[2-[2-[[3-(2,5-dioxo-2,5-dihydro-pyrrol-1-yl)-propionylamino]ethoxy]ethoxy]ethoxy]ethoxy]ethoxy]ethoxy]ethoxy]propionic acid-2,5-dioxo-pyrrolidin-1-yl ester (100 mg, 0.145 mmol), and DIPEA (194 mg, 261 uL, 1.5 mmol), and after HPLC purification, resulted in a white solid (50 mg, 28%). ES(+)-HRMS m/e calcd. for $C_{52}H_{65}Cl_4N_5O_{17}$ $(M+Na)^+$ 1194.3022, obsd. 1194.3028.

Example 7

(S)-3-[4-(2,6-dichlorobenzoylamino)phenyl]-2-[2,6-dichloro-4-[3-[3-[2-[2-[2-[2-[2-[2-[2-[2-[2-[2-[2-[3-(2,5-dioxo-2,5-dihydropyrrol-1-yl)propionylamino]ethoxy]ethoxy]ethoxy]ethoxy]ethoxy]ethoxy]ethoxy]ethoxy]ethoxy]ethoxy]ethoxy]propionylamino]propoxy]benzoylamino]propionic acid; VLA-4 Ligand Reagent 7

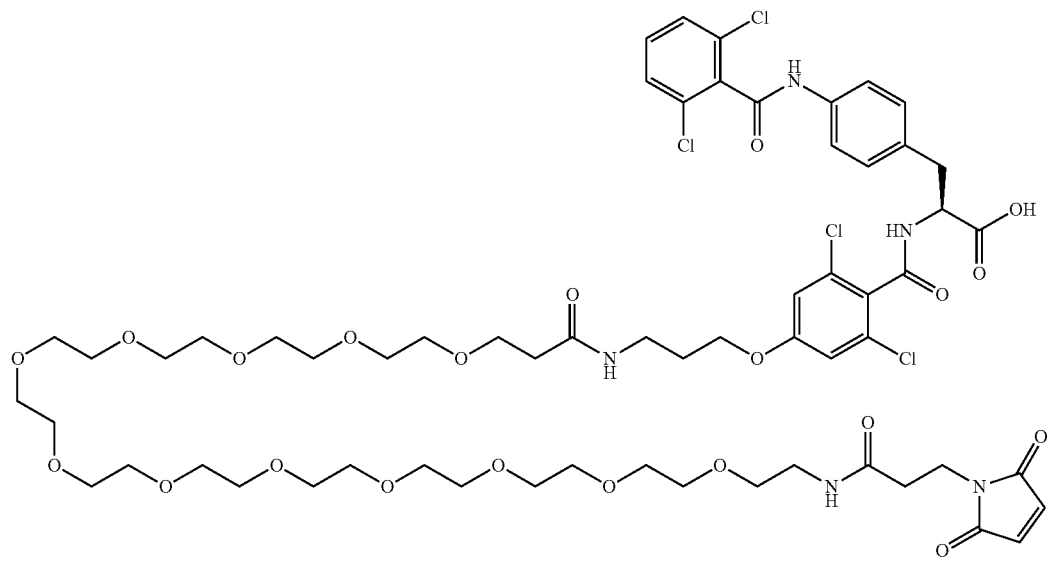 [SMILES: O=C(CCOCCOCCOCCOCCOCCOCCOCCOCCOCCOCCOCCOCCNC(=O)CCN1C(=O)C=CC1=O)NCCCOc1cc(Cl)c(C(=O)N[C@@H](Cc2ccc(NC(=O)c3c(Cl)cccc3Cl)cc2)C(=O)O)c(Cl)c1]

The title compound was prepared using a similar procedure as described in Example 1, Step 11, starting from (S)-2-[4-(3-aminopropoxy)-2,6-dichlorobenzoylamino]-3-[4-(2,6-dichlorobenzoylamino)phenyl]propionic acid (143 mg, 0.2 mmol), 3-[2-[2-[2-[2-[2-[2-[2-[2-[2-[2-[[3-(2,5-dioxo-2,5-dihydro- pyrrol-1-yl)propionylamino]ethoxy]ethoxy]ethoxy]ethoxy]ethoxy]ethoxy]ethoxy]ethoxy]ethoxy]ethoxy]propionic acid-2,5-dioxo-pyrrolidin-1-yl ester (173 mg, 0.2 mmol), and DIPEA (258 mg, 348 uL, 2.0 mmol), and after HPLC purification, resulted in a white solid (45 mg, 16.6%). ES(+)-HRMS m/e calcd. for $C_{60}H_{81}Cl_4N_5O_{21}$ (M+Na)$^+$ 1370.4070, obsd. 1370.4066.

Example 8

(S)-2-[[1-[4-[3-[2-[2-[2-[2-[3-(2,5-dioxo-2,5-dihydropyrrol-1-yl)propionylamino]ethoxy]ethoxy]ethoxy]ethoxy]propionylamino]butyl]cyclopentanecarbonyl]amino]-3-[4-(1,3,6-trimethyl-2,4-dioxo-1,2,3,4-tetrahydropyrimidin-5-yl)phenyl]propionic acid; VLA-4 Ligand Reagent 8

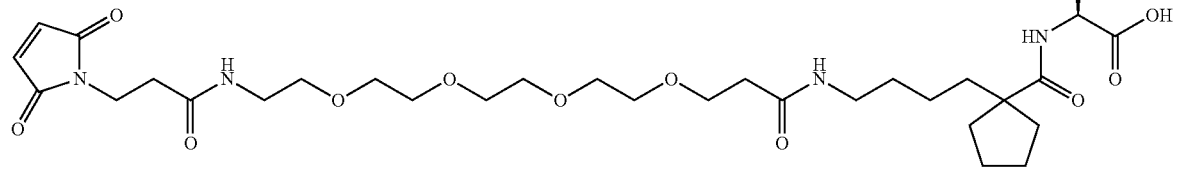

Step 1: Preparation of 1-(4-bromobutyl)cyclopentanecarboxylic acid methyl ester:

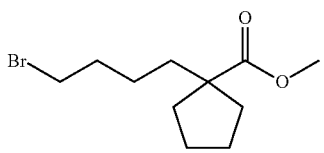

The title compound was prepared using a similar procedure as described in Example 1, Step 1, starting from diisopropylamine (21 mL, 150 mmol), n-butyllithium (58 mL, 145 mmol), cyclopentanecarboxylic acid methyl ester (13.1 g, 100 mmol), and 1,4-dibromobutane (21.59 g, 100 mmol), and after distillation, resulted in a colorless oil (12.8 g, 48%). ES(+)-HRMS m/e calcd. for $C_{11}H_{19}BrO_2$ (M+H)$^+$ 262.0568, obsd. 262.0565.

Step 2: Preparation of 1-[4-azidobutyl]cyclopentanecarboxylic acid methyl ester:

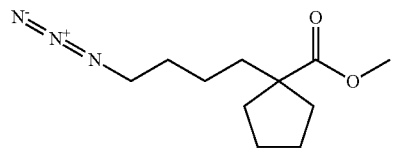 [SMILES: COC(=O)C1(CCCCN=[N+]=[N-])CCCC1]

The title compound was prepared using a similar procedure as described in Example 1, Step 2, starting from 1-[4-bromobutyl]cyclopentanecarboxylic acid methyl ester and sodium azide.

Step 3: Preparation of 1-[4-azidobutyl]cyclopentanecarboxylic acid:

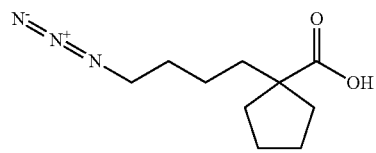 [SMILES: [N-]=[N+]=NCCCCC1(C(=O)O)CCCC1]

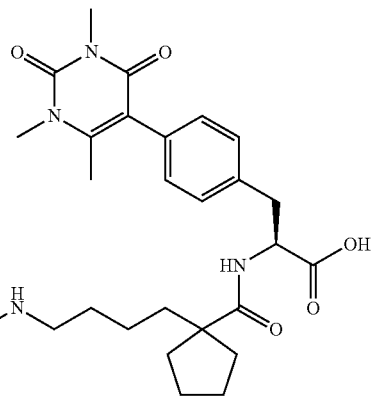

The title compound was prepared using a similar procedure as described in Example 1, Step 3, starting from 1-[4-azidobutyl]cyclopentanecarboxylic acid methyl ester and lithium hydroxide.

Step 4: Preparation of (S)-2-tert-butoxycarbonylamino-3-[4-(1,3,6-trimethyl-2,4-dioxo-1,2,3,4-tetrahydropyrimidin-5-yl)phenyl]propionic acid methyl ester:

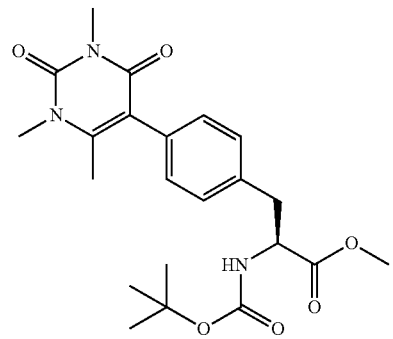 [SMILES: COC(=O)[C@H](Cc1ccc(-c2c(C)n(C)c(=O)n(C)c2=O)cc1)NC(=O)OC(C)(C)C]

To a suspension of zinc dust (52.29 g, 800 mmol) in THF (26.0 mL) was added 1,2-dibromoethane (4.58 mL, 53.2 mmol) at room temperature. This suspension was heated to 60-65° C. with a heat gun until evolution of ethylene gas ceased (observed). The suspension was cooled to room temperature, trimethylchlorosilane (3.38 mL, 26.6 mmol) was added and the mixture was stirred for 15 min. A suspension of 5-iodo-1,3,6-trimethyl uracil (74.6 g, 266 mmol) in DMA (225 mL) was warmed to obtain a clear solution and was added in one portion to the reaction mixture. After addition, the mixture was heated to 70° C. The internal temperature of the reaction mixture rose to 80-85° C. due to the exothermic reaction. The reaction mixture was stirred at 70° C. for 3-4 h at which time TLC of an aliquot which had been quenched with saturated ammonium chloride indicated the absence of starting material. The reaction mixture was diluted with THF (140 mL), was cooled to room temperature and the excess zinc dust was allowed to settle over 2-3 h.

This solution containing the zinc compound (266 mmol) was added to a solution of Pd(dba)$_2$ (4.6 g, 8 mmol), tri-o-tolylphosphine [P(Tol)$_3$] (9.0 g, 29.6 mmol) and (S)-2-tert-butoxycarbonylamino-3-(4-iodo)phenyl]propionic acid methyl ester (75.56 g, 186 mmol) in THF (280 mL) at room temperature and the light yellow mixture was stirred for 48 h at 50-55° C. The reaction mixture was poured into a saturated ammonium chloride solution and was extracted with ethyl acetate (3×750 mL). The combined extracts were washed with brine solution (1.5 L) and dried over anhydrous magnesium sulfate. Filtration of the drying agent and concentration gave the crude product, which was purified by silica gel column chromatography using a Biotage (75 m) column to obtain 57.88 g (72% yield) of (S)-2-tert-butoxycarbonylamino-3-[4-(1,3,6-trimethyl-2,4-dioxo-1,2,3,4-tetrahydropyrimidin-5-yl)phenyl]propionic acid methyl ester as an amorphous white solid. EI-HRMS m/e calcd for $C_{22}H_{29}N_3O_6$ (M+) 431.2056, found 431.2054.

Step 5: Preparation of (S)-2-amino-3-[4-(1,3,6-trimethyl-2,4-dioxo-1,2,3,4-tetrahydropyrimidin-5-yl)phenyl]propionic acid methyl ester hydrochloride salt:

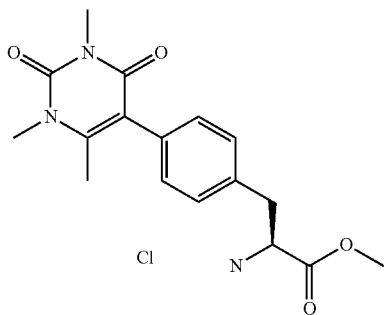 [SMILES: COC(=O)[C@@H](N)Cc1ccc(-c2c(C)n(C)c(=O)n(C)c2=O)cc1 ; Cl]

A portion of the solid (S)-2-tert-butoxycarbonylamino-3-[4-(1,3,6-trimethyl-2,4-dioxo-1,2,3,4-tetrahydropyrimidin-5-yl)phenyl]propionic acid methyl ester (7.4 g, 17.15 mmol) obtained above was treated with 4N hydrochloric acid in dioxane (17 mL, 68 mmol,) at room temperature and the solution was stirred for 1 h as a white precipitate formed. The mixture was diluted with diethyl ether and the supernatant was decanted and the residue was dried first on the rotary evaporator and then under high vacuum to afford 6.28 g (99% yield) of (S)-2-amino-3-[4-(1,3,6-trimethyl-2,4-dioxo-1,2,3,4-tetrahydropyrimidin-5-yl)phenyl]propionic acid methyl ester hydrochloride salt as an amorphous yellow solid. FAB-HRMS m/e calcd for $C_{17}H_{21}N_3O_4$ (M+H) 332.1610, found 332.1617.

Step 6: Preparation of (S)-2-[[1-(4-azidobutyl)cyclopentanecarbonyl]amino]-3-[4-(1,3,6-trimethyl-2,4-dioxo-1,2,3,4-tetrahydropyrimidin-5-yl)phenyl]propionic acid propyl ester:

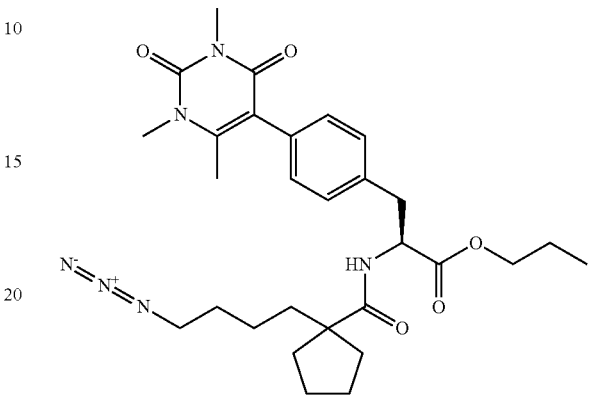

The title compound was prepared using a similar procedure as described in Example 1, Step 8, starting from (S)-2-amino-3-[4-(1,3,6-trimethyl-2,4-dioxo-1,2,3,4-tetrahydropyrimidin-5-yl)phenyl]propionic acid propyl ester (10.78 g, 30 mmol), 1-[4-azidobutyl]cyclopentanecarboxylic acid (8.24 g, 39 mmol), HBTU (14.79 g, 39 mmol), and DIPEA (11.63 g, 15.68 mL, 90 mmol), and after ISCO column chromatography purification, resulted in an amorphous off-white solid (14.1 g, 85%). ES(+)-HRMS m/e calcd. for $C_{29}H_{40}N_6O_5$ (M+H)+ 553.3133, obsd. 553.3133.

Step 7: Preparation of (S)-2-[[1-(4-azidobutyl)cyclopentanecarbonyl]amino]-3-[4-(1,3,6-trimethyl-2,4-dioxo-1,2,3,4-tetrahydropyrimidin-5-yl)phenyl]propionic acid:

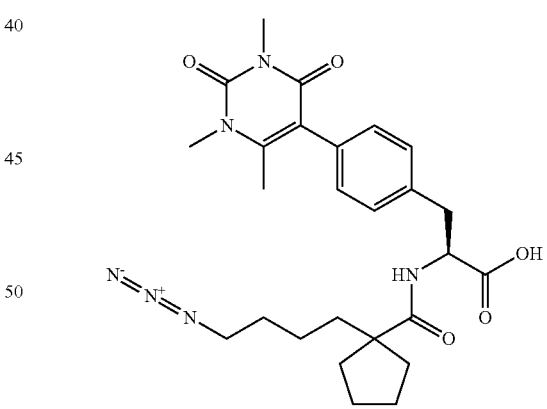

The title compound was prepared using a similar procedure as described in Example 1, Step 9, starting from (S)-2-[[1-(4-azidobutyl)cyclopentanecarbonyl]amino]-3-[4-(1,3,6-trimethyl-2,4-dioxo-1,2,3,4-tetrahydropyrimidin-5-yl)phenyl]propionic acid propyl ester (4.1 g, 7.42 mmol) and NaOH (35 mL, 35 mmol, 1M) which resulted in a white solid (3.75 g, 99%). ES(+)-HRMS m/e calcd. for $C_{26}H_{34}N_6O_5$ (M+H)+ 511.2664, obsd. 511.2664.

Step 8: Preparation of (S)-2-[[1-(4-aminobutyl)cyclopentanecarbonyl]amino]-3-[4-(1,3,6-trimethyl-2,4-dioxo-1,2,3,4-tetrahydropyrimidin-5-yl)phenyl]propionic acid; VLA-4 Ligand 3:

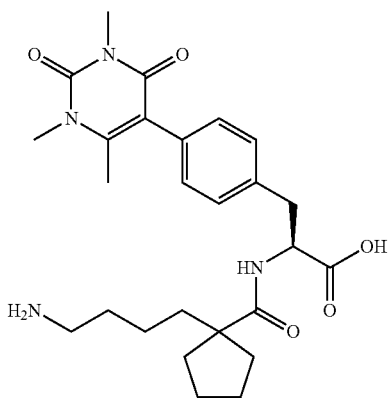 [SMILES: Cc1c(-c2ccc(C[C@H](NC(=O)C3(CCCCN)CCCC3)C(=O)O)cc2)c(=O)n(C)c(=O)n1C]

The title compound was prepared using a similar procedure as described in Example 1, Step 10, starting from (S)-2-[[1-(4-azidobutyl)cyclopentanecarbonyl]amino]-3-[4-(1,3,6-trimethyl-2,4-dioxo-1,2,3,4-tetrahydropyrimidin-5-yl)phenyl]propionic acid (1.02 g, 2 mmol) and trimethylphosphine (8 mL, 8 mmol, 1M) to obtain a white solid (0.96 g, 99%). ES(+)-HRMS m/e calcd. for $C_{26}H_{36}N_4O_5$ $(M+H)^+$ 485.2759, obsd. 485.2757.

Step 9: Preparation (S)-2-[[1-[4-[3-[2-[2-[2-[2-[3-(2,5-dioxo-2,5-dihydropyrrol-1-yl)propionylamino]ethoxy]ethoxy]ethoxy]ethoxy]propionylamino]butyl]cyclopentanecarbonyl]amino]-3-[4-(1,3,6-trimethyl-2,4-dioxo-1,2,3,4-tetrahydropyrimidin-5-yl)phenyl]propionic acid; VLA-4 Ligand Reagent 8:

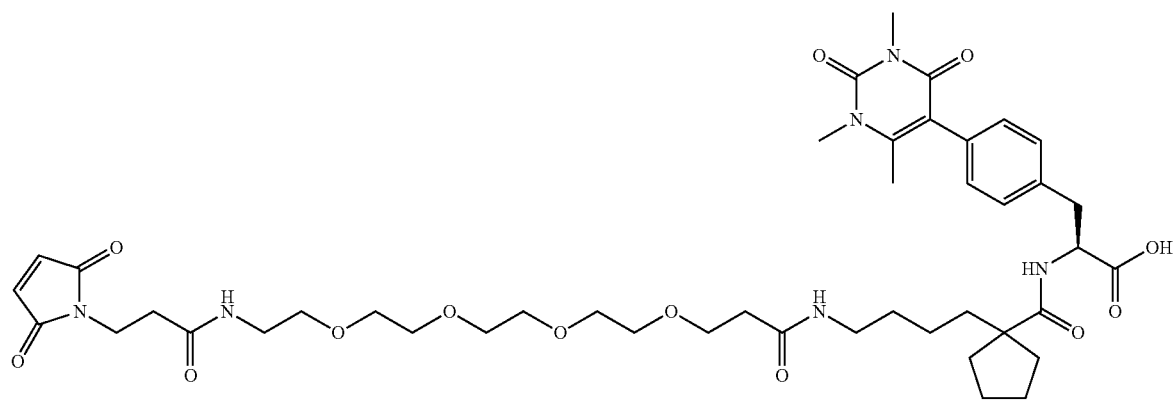 [SMILES: Cc1c(-c2ccc(C[C@H](NC(=O)C3(CCCCNC(=O)CCOCCOCCOCCOCCNC(=O)CCN4C(=O)C=CC4=O)CCCC3)C(=O)O)cc2)c(=O)n(C)c(=O)n1C]

The title compound was prepared using a similar procedure as described in Example 1, Step 11, starting from (S)-2-[[1-(4-aminobutyl)cyclopentanecarbonyl]amino]-3-[4-(1,3,6-trimethyl-2,4-dioxo-1,2,3,4-tetrahydropyrimidin-5-yl)phenyl]propionic acid (300 mg, 0.62 mmol), 3-[2-[2-[2-[[3-(2,5-dioxo-2,5-dihydro-pyrrol-1-yl)-propionylamino]-ethoxy]ethoxy]ethoxy]ethoxy]propionic acid-2,5-dioxo-pyrrolidin-1-yl ester (318 mg, 0.62 mmol), and DIPEA (160 mg, 215 uL, 1.24 mmol), and after HPLC purification, resulted in a light yellow solid (274 mg, 50%). ES(+)-HRMS m/e calcd. for $C_{44}H_{62}N_6O_{13}$ $(M+H)^+$ 883.4448, obsd. 883.4449.

Example 9

(S)-2-[2,6-Dichloro-4-[3-[3-[2-[2-[2-[2-[3-(2,5-di-oxo-2,5-dihydropyrrol-1-yl)propionylamino]ethoxy]ethoxy]ethoxy]ethoxy]propionylamino]propoxy]benzoylamino]-3-[4-(1,3,6-trimethyl-2,4-dioxo-1,2,3,4-tetrahydropyrimidin-5-yl)phenyl]propionic acid VLA-4 Ligand Reagent 9

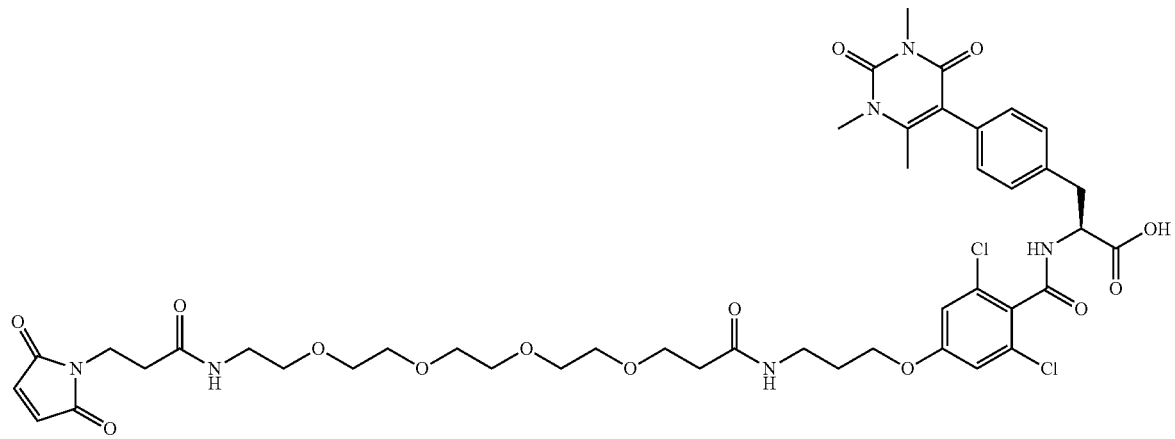 [SMILES: Cc1c(-c2ccc(C[C@H](NC(=O)c3c(Cl)cc(OCCCNC(=O)CCOCCOCCOCCOCCNC(=O)CCN4C(=O)C=CC4=O)cc3Cl)C(=O)O)cc2)c(=O)n(C)c(=O)n1C]

Step 1: Preparation of (S)-2-(2,6-dichloro-4-triisopropylsilanyloxy-benzoylamino)-3-[4-(1,3,6-trimethyl-2,4-dioxo-1,2,3,4-tetrahydropyrimidin-5-yl)phenyl]propionic acid propyl ester

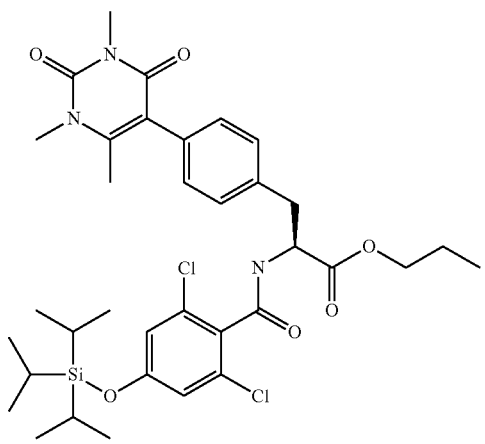 [SMILES: CCCOC(=O)[C@H](Cc1ccc(-c2c(C)n(C)c(=O)n(C)c2=O)cc1)NC(=O)c1c(Cl)cc(O[Si](C(C)C)(C(C)C)C(C)C)cc1Cl]

The title compound was prepared using a similar procedure as described in Example 1, Step 8, starting from (S)-2-amino-3-[4-(1,3,6-trimethyl-2,4-dioxo-1,2,3,4-tetrahydropyrimidin-5-yl)phenyl]propionic acid propyl ester (3.95 g, 11 mmol), 2,6-dichloro-4-triisopropylsilanyloxy-benzoic acid (3.63 g, 10 mmol), HBTU (5.42 g, 14.3 mmol), and DIPEA (4.26 g, 5.75 mL, 33.0 mmol), and after ISCO column chromatography purification, resulted in an amorphous white solid (1.7 g, 24%). ES(+)-HRMS m/e calcd. for $C_{35}H_{47}Cl_2N_3O_6Si$ (M+H)$^+$ 704.2684, obsd. 704.2683.

Step 2: Preparation of (S)-2-(2,6-dichloro-4-hydroxy-benzoylamino)-3-[4-(1,3,6-trimethyl-2,4-dioxo-1,2,3,4-tetrahydropyrimidin-5-yl)phenyl]propionic acid propyl ester:

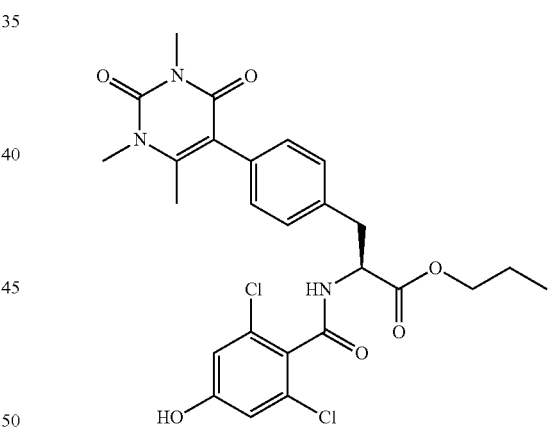

The title compound was prepared using a similar procedure as described in Example 5, Step 4, starting from (S)-2-(2,6-dichloro-4-triisopropylsilanyloxy-benzoylamino)-3-[4-(1,3,6-trimethyl-2,4-dioxo-1,2,3,4-tetrahydropyrimidin-5-yl)phenyl]propionic acid propyl ester (1.66 g, 2.35 mmol) and TBAF (3.5 mL, 3.5 mmol, 1M), and after ISCO column chromatography purification, resulted in a white solid (884 mg, 69%). ES(+)-LRMS m/e calcd. for $C_{26}H_{27}Cl_2N_3O_6$ (M+H)$^+$ 548, obsd. 548.

Step 3: Preparation of (S)-2-[4-(3-tert-butoxycarbonylaminopropoxy)-2,6-dichlorobenzoylamino]-3-[4-(1,3,6-trimethyl-2,4-dioxo-1,2,3,4-tetrahydropyrimidin-5-yl)phenyl]propionic acid propyl ester:

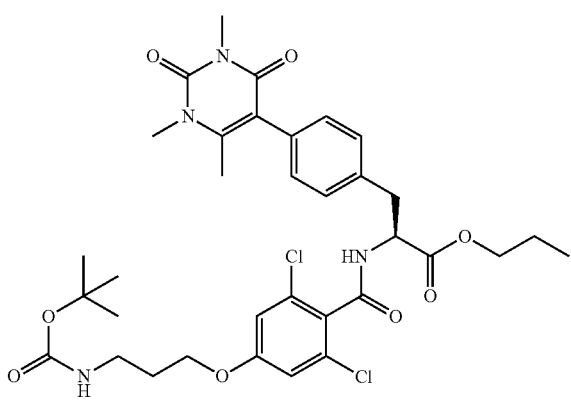 [SMILES: CCCOC(=O)[C@H](Cc1ccc(-c2c(C)n(C)c(=O)n(C)c2=O)cc1)NC(=O)c1c(Cl)cc(OCCCNC(=O)OC(C)(C)C)cc1Cl]

The title compound was prepared using a similar procedure as described in Example 5, Step 5, starting from (S)-2-(2,6-dichloro-4-hydroxy-benzoylamino)-3-[4-(1,3,6-trimethyl-2,4-dioxo-1,2,3,4-tetrahydropyrimidin-5-yl)phenyl]propionic acid propyl ester (558 mg, 1.07 mmol), 3-tert-butoxycarbonylaminopropyl bromide (306 mg, 1.28 mmol), and potassium carbonate (445 mg, 3.22 mmol), and after ISCO column chromatography purification, resulted in a white solid (654 mg, 87%). ES(+)-HRMS m/e calcd. for $C_{34}H_{42}Cl_2N_4O_8$ (M+H)$^+$ 705.2453, obsd. 705.2451.

Step 4: Preparation of (S)-2-[4-(3-aminopropoxy)-2,6-dichlorobenzoylamino]-3-[4-(1,3,6-trimethyl-2,4-dioxo-1,2,3,4-tetrahydropyrimidin-5- yl)phenyl]propionic acid propyl ester trifluoroacetate salt:

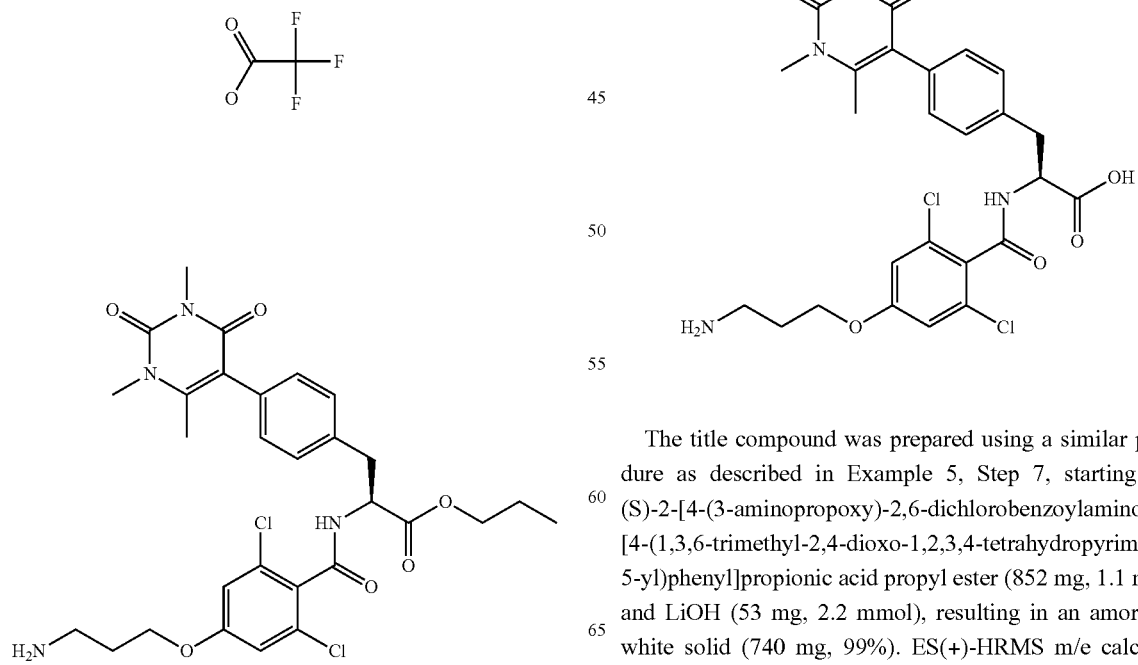

The title compound was prepared using a similar procedure as described in Example 5, Step 6, starting from (S)-2-[4-(3-tert-butoxycarbonylaminopropoxy)-2,6-dichlorobenzoylamino]-3-[4-(1,3,6-trimethyl-2,4-dioxo-1,2,3,4-tetrahydropyrimidin-5- yl)phenyl]propionic acid propyl ester (781 mg, 1.1 mmol) and TFA (1.14 g, 742 uL, 10 mmol), resulting in a hygroscopic white solid (790 mg, 99%). ES(+)-HRMS m/e calcd. for $C_{29}H_{34}Cl_2N_4O_6$ (M+H)$^+$ 605.1928, obsd. 605.1929.

Step 5: Preparation of (S)-2-[4-(3-aminopropoxy)-2,6-dichlorobenzoylamino]-3-[4-(1,3,6-trimethyl-2,4-dioxo-1,2,3,4-tetrahydropyrimidin-5- yl)phenyl]propionic acid trifluoroacetate salt:

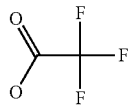

The title compound was prepared using a similar procedure as described in Example 5, Step 7, starting from (S)-2-[4-(3-aminopropoxy)-2,6-dichlorobenzoylamino]-3-[4-(1,3,6-trimethyl-2,4-dioxo-1,2,3,4-tetrahydropyrimidin-5-yl)phenyl]propionic acid propyl ester (852 mg, 1.1 mmol) and LiOH (53 mg, 2.2 mmol), resulting in an amorphous white solid (740 mg, 99%). ES(+)-HRMS m/e calcd. for $C_{26}H_{28}Cl_2N_4O_6$ (M+H)$^+$ 563.1459, obsd. 563.1455.

Step 6: Preparation of (S)-2-[2,6-dichloro-4-[3-[3-[2-[2-[2-[2-[3-(2,5-dioxo-2,5-dihydropyrrol-1-yl)propionylamino]ethoxy]ethoxy]ethoxy]ethoxy]propionylamino]propoxy]benzoylamino]-3-[4-(1,3,6-trimethyl-2,4-dioxo-1,2,3,4-tetrahydropyrimidin-5-yl)phenyl]propionic acid; VLA-4 Ligand Reagent 9:

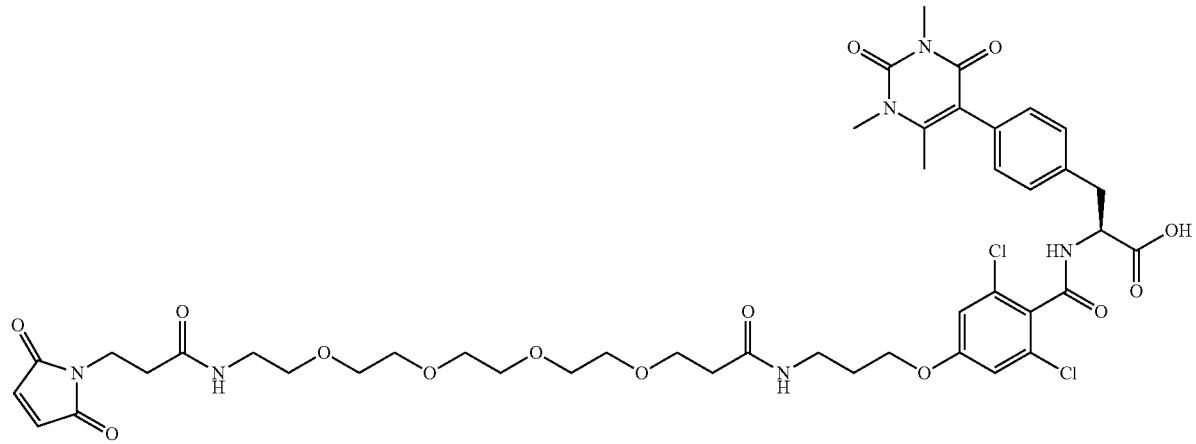 [SMILES: Cc1c(-c2ccc(C[C@H](NC(=O)c3c(Cl)cc(OCCCNC(=O)CCOCCOCCOCCOCCNC(=O)CCN4C(=O)C=CC4=O)cc3Cl)C(=O)O)cc2)c(=O)n(C)c(=O)n1C]

The title compound was prepared using a similar procedure as described in Example 1, Step 11, starting from (S)-2-[4-(3-aminopropoxy)-2,6-dichlorobenzoylamino]-3-[4-(1,3,6-trimethyl-2,4-dioxo-1,2,3,4-tetrahydropyrimidin-5-yl)phenyl]propionic acid trifluoroacetate salt (203 mg, 0.3 mmol), 3-[2-[2-[2-[[3-(2,5-dioxo-2,5-dihydro-pyrrol-1-yl)-propionylamino]-ethoxy]ethoxy]ethoxy]propionic acid-2,5-dioxo-pyrrolidin-1-yl ester (154 mg, 0.3 mmol), and DIPEA (194 mg, 261 uL, 1.5 mmol), and after HPLC purification, resulted in an amorphous white solid (175 mg, 61%). ES(+)-HRMS m/e calcd. for $C_{44}H_{54}Cl_2N_6O_{14}$ $(M+H)^+$ 961.3148, obsd. 961.3156.

Example 10

Preparation of (S)-2-[2,6-dichloro-4-[3-[3-[2-[2-[2-[2-[2-[2-[2-[2-[3-(2,5-dioxo-2,5- dihydropyrrol-1-yl)propionylamino]ethoxy]ethoxy]ethoxy]ethoxy]ethoxy]ethoxy]ethoxy]propionylamino]propoxy]benzoylamino]-3-[4-(1,3,6-trimethyl-2,4-dioxo-1,2,3,4-tetrahydropyrimidin-5-yl)phenyl]propionic acid; VLA-4 Ligand Reagent 10

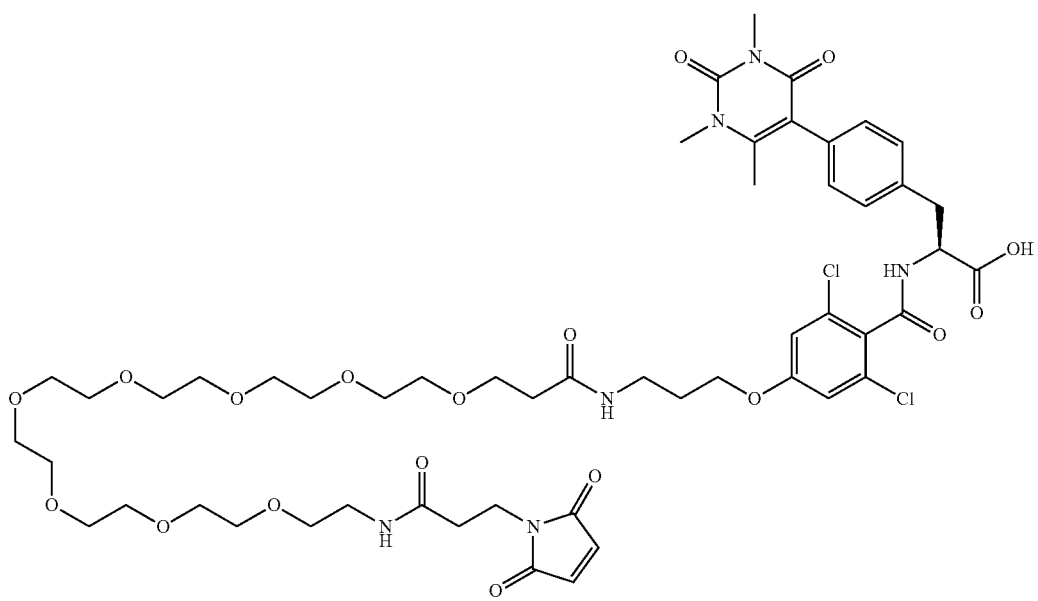 [SMILES: Cc1c(-c2ccc(C[C@H](NC(=O)c3c(Cl)cc(OCCCNC(=O)CCOCCOCCOCCOCCOCCOCCOCCOCCNC(=O)CCN4C(=O)C=CC4=O)cc3Cl)C(=O)O)cc2)c(=O)n(C)c(=O)n1C]

The title compound was prepared using a similar procedure as described in Example 1, Step 11, starting from (S)-2-[4-(3-aminopropoxy)-2,6-dichlorobenzoylamino]-3-[4-(1,3,6-trimethyl-2,4-dioxo-1,2,3,4-tetrahydropyrimidin-5-yl)phenyl]propionic acid trifluoroacetate salt (98 mg, 0.145 mmol), 3-[2-[2-[2-[2-[2-[2-[2-[[3-(2,5-dioxo-2,5-dihydro-pyrrol-1-yl)-propionylamino]ethoxy]ethoxy]ethoxy]ethoxy]ethoxy]ethoxy]propionic acid-2,5-dioxo-pyrrolidin-1-yl ester (100 mg, 0.145 mmol), and DIPEA (187 mg, 252 uL, 1.45 mmol), and after HPLC purification, resulted in a hygroscopic white solid (88 mg, 53%). ES(+)-HRMS m/e calcd. for $C_{52}H_{70}Cl_2N_6O_{18}$ $(M+H)^+$ 1137.4197, obsd. 1137.4196.

Example 11

(S)-2-[4-[(3-[2-[2-[2-[2-[3-(2,5-Dioxo-2,5-dihydro-pyrrol-1-yl)propionylamino]ethoxy]ethoxy]ethoxy]ethoxy]propionylamino)methyl]-2,6-difluorobenzoylamino]-3-[4-(1,3,6-trimethyl-2,4-dioxo-1,2,3,4-tetrahydropyrimidin-5-yl)phenyl]propionic acid trifluoracetate salt; VLA-4 Ligand Reagent 11

The title compound was prepared using a similar procedure as described in Example 1, Step 8, starting from (S)-2-amino-3-[4-(1,3,6-trimethyl-2,4-dioxo-1,2,3,4-tetrahydropyrimidin-5-yl)phenyl]propionic acid propyl ester (4.67 g, 13 mmol), 4-bromo-2,6-difluorobenzoic acid (3.12 g, 13.16 mmol), HBTU (4.99 g, 13.16 mmol), and DIPEA (6.8 mL, 39 mmol), and after ISCO column chromatography purification, resulted in an amorphous off-white solid (6.71 g, 89%). ES-HRMS m/e calcd for $C_{26}H_{26}BrF_2N_3O_5$ $(M+H)^+$ 578.1097, found 578.1096.

Step 2: Preparation of (S)-2-(4-cyano-2,6-difluorobenzoylamino)-3-[4-(1,3,6-trimethyl-2,4-dioxo-1,2,3,4-tetrahydropyrimidin-5-yl)phenyl]propionic acid propyl ester:

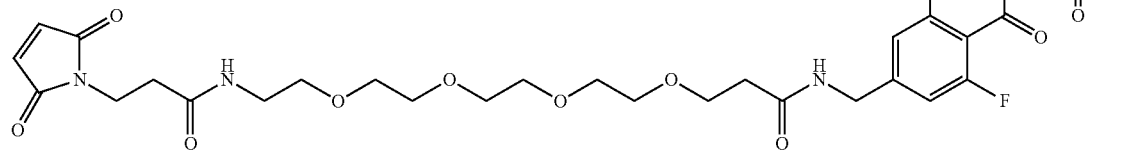

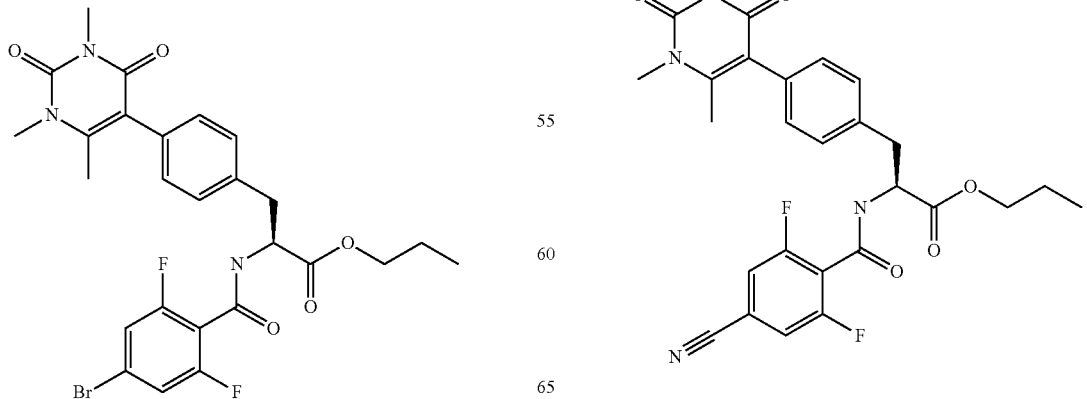

Step 1: Preparation of (S)-2-(4-bromo-2,6-difluorobenzoylamino)-3-[4-(1,3,6-trimethyl-2,4-dioxo-1,2,3,4-tetrahydropyrimidin-5-yl)phenyl]propionic acid propyl ester:

To a suspension of (S)-2-(4-bromo-2,6-difluorobenzoylamino)-3-[4-(1,3,6-trimethyl-2,4-dioxo-1,2,3,4-tetrahydropyrimidin-5-yl)phenyl]propionic acid propyl ester (5.78 g, 10 mmol), zinc cyanide (940 mg, 8 mmol), and tetrakis(triphenylphosphine)palladium (1.16 g, 1 mmol) in DMF (40 mL, distilled and degassed) at room temperature. The resulting solution was heated to 85° C. and stirred for 24 h at which time TLC analysis of the mixture indicated the absence of starting material. Then, the reaction mixture was cooled to room temperature and it was poured into water (100 mL) to afford a cloudy suspension. Then, the organic compound was extracted with ethyl acetate (2×100 mL). The combined extracts were washed with brine solution (100 mL) and dried over anhydrous magnesium sulfate. Filtration of the drying agent and concentration of the solvent gave the crude product which was purified using an ISCO (150 g) column chromatography to afford 5.2 g (99% yield) of (S)-2-(4-cyano-2,6-difluorobenzoylamino)-3-[4-(1,3,6-trimethyl-2,4-dioxo-1,2,3,4-tetrahydropyrimidin-5-yl)phenyl]propionic acid propyl ester as an amorphous white solid. ES-HRMS m/e calcd for $C_{27}H_{26}F_2N_4O_5$(M+H)$^+$ 525.1944, found 525.1942.

Step 3: Preparation of (S)-2-(4-aminomethyl-2,6-difluorobenzoylamino)-3-[4-(1,3,6-trimethyl-2,4-dioxo-1,2,3,4-tetrahydropyrimidin-5-yl)phenyl]propionic acid propyl ester:

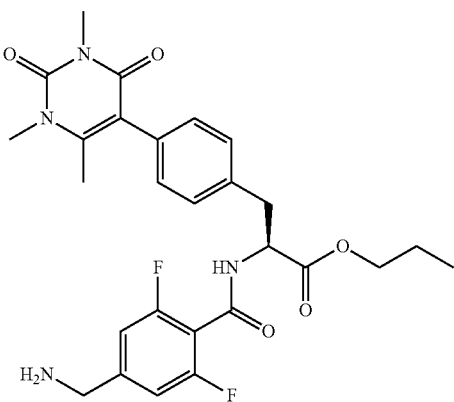 [SMILES: CCCOC(=O)[C@H](Cc1ccc(-c2c(C)n(C)c(=O)n(C)c2=O)cc1)NC(=O)c1c(F)cc(CN)cc1F]

To solution of sodium borohydride (0.29 g, 7.62 mmol, 2 eq.) in THF (5 ml) was added TFA (566 µL, 7.62 mmol, 2 eq.), the reaction was stirred for 10 min., and then a solution of (S)-2-(4-cyano-2,6-difluoro-benzoylamino)-3-[4-(1,3,6-trimethyl-2,4-dioxo-1,2,3,4-tetrahydro-pyrimidin-5-yl)-phenyl]-propionic acid propyl ester (2.0 g, 3.81 mmol) in THF (6 ml) was added drop wise (flask was rinsed w/THF (2×1 ml) and added to reaction). The reaction was stirred at room temperature under nitrogen for 1.3 h. The reaction mixture was cooled in an ice bath and quenched with water (20 ml) and a sodium chloride solution (20 ml water, 100 ml saturated solution). The aqueous mixture was extracted with DCM (2×200 ml), and then the organic layers were washed with brine, combined, and dried over magnesium sulfate, and then concentrated to yield an off white solid, 1.77 g. The crude product was suspended in isopropyl acetate (75 ml) and isopropyl alcohol (0.75 ml and TMSC1 (1 ml) was added dropwise. The reaction was stirred at room temperature for 2 h and the white precipitate was filtered and washed with isopropyl acetate and hexanes to obtain 1.5 g (63% yield) of (S)-2-(4-aminomethyl-2,6-difluorobenzoylamino)-3-[4-(1,3,6-trimethyl-2,4-dioxo-1,2,3,4-tetrahydropyrimidin-5-yl)phenyl]propionic acid propyl ester as an amorphous white solid. ES-HRMS m/e calcd for $C_{27}H_{30}F_2N_4O_5$ (M+H)$^+$ 529.2257, found 529.2258.

Step 4: Preparation of (S)-2-(4-aminomethyl-2,6-difluorobenzoylamino)-3-[4-(1,3,6-trimethyl-2,4-dioxo-1,2,3,4-tetrahydropyrimidin-5-yl)phenyl]propionic acid trifluoroacetate salt; VLA-4 Ligand 4:

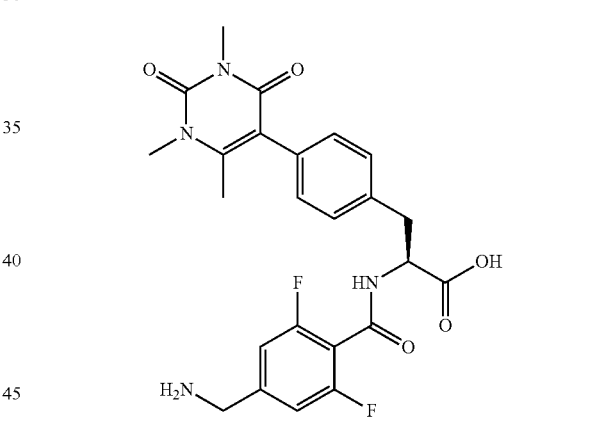

To a suspension of (S)-2-(4-aminomethyl-2,6-difluorobenzoylamino)-3-[4-(1,3,6-trimethyl-2,4-dioxo-1,2,3,4-tetrahydropyrimidin-5-yl)phenyl]propionic acid propyl ester (508 mg, 0.96 mmol) in THF (10 mL) was added a solution of lithium hydroxide (240 mg, 10 mmol) in water (2 mL) at room temperature. The mixture was stirred for 15 h at which time TLC analysis indicated the absence of starting material. Then, the THF was removed under reduced pressure and the residue was diluted with water (100 mL) and the mixture was acidified with TFA. The crude product was purified by HPLC to afford 450 mg (78% yield) of (S)-2-(4-aminomethyl-2,6-difluorobenzoylamino)-3-[4-(1,3,6-trimethyl-2,4-dioxo-1,2,3,4-tetrahydropyrimidin-5-yl)phenyl]propionic acid as a TFA salt as a white solid. ES-LRMS m/e calcd for $C_{24}H_{24}F_2N_4O_5$ (M+H)$^+$ 487, found 487.

Step 5: Preparation of (S)-2-[4-[(3-[2-[2-[2-[2-[3-(2,5-dioxo-2,5-dihydropyrrol-1-yl)propionylamino]ethoxy]ethoxy]ethoxy]propionylamino)methyl]-2,6-difluorobenzoylamino]-3-[4-(1,3,6-trimethyl-2,4-dioxo-1,2,3,4-tetrahydropyrimidin-5-yl)phenyl]propionic acid:

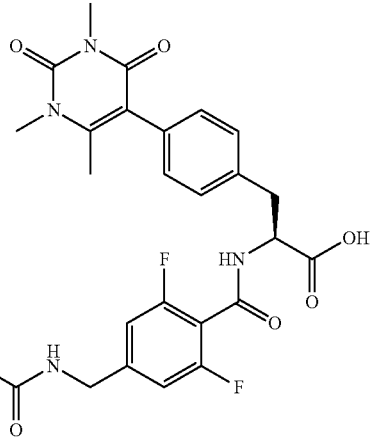
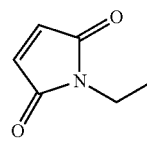

The title compound was prepared using a similar procedure as described in Example 1, Step 11, starting from (S)-2-(4-aminomethyl-2,6-difluorobenzoylamino)-3-[4-(1,3,6-trimethyl-2,4-dioxo-1,2,3,4-tetrahydropyrimidin-5-yl)phenyl]propionic acid TFA salt (120 mg, 0.2 mmol), 3-[2-[2-[2-[2-[3-(2,5-dioxo-2,5-dihydro-pyrrol-1-yl)-propionylamino]ethoxy]ethoxy]ethoxy]propionic acid-2,5-dioxo-pyrrolidin-1-yl ester (103 mg, 0.2 mmol), and DIPEA (129 mg, 174 uL, 1.0 mmol), and after HPLC purification, resulted in a white solid (75 mg, 43%). ES(+)-HRMS m/e calcd. for $C_{42}H_{50}F_2N_6O_{13}$ (M+Na)$^+$ 907.3296, obsd. 907.3296.

Example 12

Preparation of (S)-2-[4-[(3-[2-[2-[2-[2-[2-[2-[2-[3-(2,5-Dioxo-2,5-dihydropyrrol-1-yl)propionylamino]ethoxy]ethoxy]ethoxy]ethoxy]ethoxy]ethoxy]ethoxy]propionylamino) methyl]-2,6-difluorobenzoylamino]-3-[4-(1,3,6-trimethyl-2,4-dioxo-1,2,3,4-tetrahydropyrimidin-5-yl)phenyl] propionic acid trifluoracetate salt; VLA-4 Ligand Reagent 12

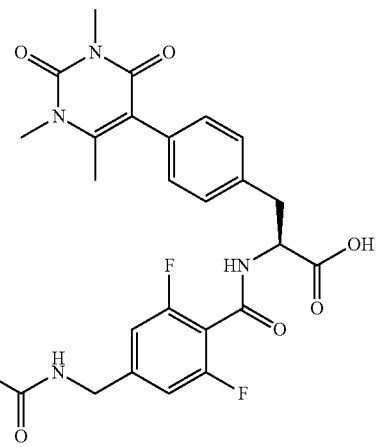
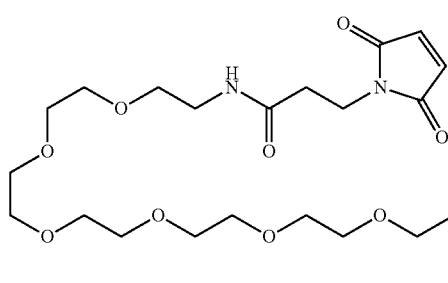

The title compound was prepared using a similar procedure as described in Example 1, Step 11, starting from (S)-2-(4-aminomethyl-2,6-difluorobenzoylamino)-3-[4-(1,3,6-trimethyl-2,4-dioxo-1,2,3,4-tetrahydropyrimidin-5-yl)phenyl]propionic acid TFA salt (121 mg, 0.2 mmol), 3-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]propionic acid-2,5-dioxo-pyrrolidin-1-yl ester (100 mg, 0.145 mmol), and DIPEA (258 mg, 348 uL, 2.0 mmol), and after HPLC purification, resulted in a white solid (80 mg, 38%). ES(+)-HRMS m/e calcd. for $C_{50}H_{66}F_2N_6O_{17}$ (M+H)$^+$ 1061.4526, obsd. 1061.4521.

Example 13

Preparation of (S)-2-[4-[[3-[2-[2-[2-[2-[2-[2-[2-[2-acetylsulfanyl-ethoxy]ethoxy]ethoxy]ethoxy]ethoxy]ethoxy]ethoxy]propionylamino]methyl]-2,6-difluorobenzoylamino]-3-[4-(1,3,6-trimethyl-2,4-dioxo-1,2,3,4-tetrahydropyrimidin-5-yl)phenyl]propionic acid; VLA-4 Ligand Reagent 13

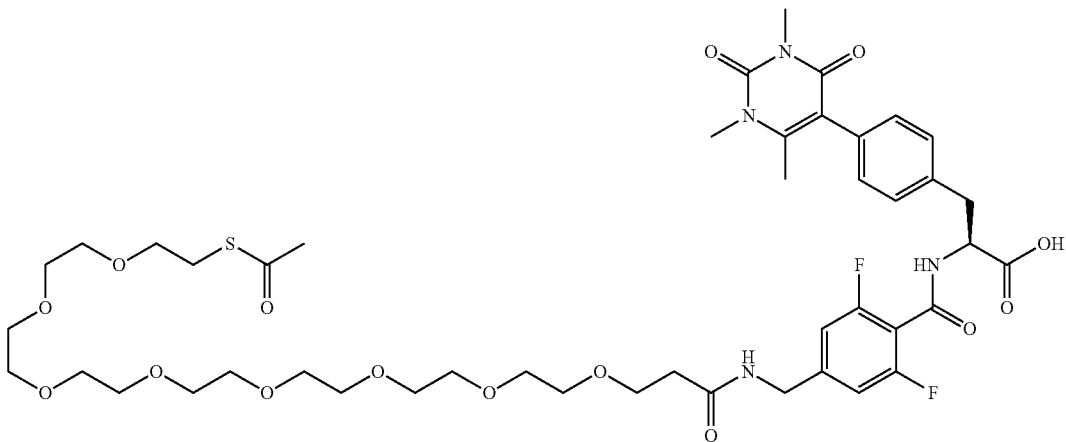 [SMILES: CC(=O)SCCOCCOCCOCCOCCOCCOCCOCCOCCC(=O)NCc1cc(F)c(C(=O)N[C@@H](Cc2ccc(-c3c(C)n(C)c(=O)n(C)c3=O)cc2)C(=O)O)c(F)c1]

The title compound was prepared using a similar procedure as described in Example 1, step 11, starting from (S)-2-(4-aminomethyl-2,6-difluorobenzoylamino)-3-[4-(1,3,6-trimethyl-2,4-dioxo-1,2,3,4-tetrahydro-pyrimidin-5-yl)phenyl]propionic acid (64 mg, 0.11 mmol), 3-[2-[2-[2-[2-[2-[2-[2-[2-acetylsulfanyl-ethoxy]ethoxy]ethoxy]ethoxy]ethoxy]ethoxy]ethoxy]ethoxy]propionic acid-2,5-dioxo-pyrrolidin-1-yl ester (64 mg, 0.11 mmol), and DIPEA (42 mg, 56 μL, 0.32 mmol), and after HPLC purification, resulted in a viscous oil (90 mg, 87%). ES(+)-LRMS m/e calcd. for $C_{45}H_{62}F_2N_4O_{15}S_1$ (M+H)+ 969, obsd 969.

Example 14

Preparation of (S)-2-[4-[[3-[3-[2-[2-[2-[2-[2-[2-[2-(2-acetylsulfanylethoxy)ethoxy]ethoxy]ethoxy]ethoxy]ethoxy]ethoxy]ethoxy]propionylamino]propionyl]-[4-[(S)-1-carboxy-2-[4-[1,3,6-trimethyl-2,4-dioxo-1,2,3,4-tetrahydropyrimidin-5-yl]phenyl]ethylcarbamoyl]-3,5-difluorobenzylamino]methyl]-2,6-difluorobenzylamino]-3-[4-[1,3,6-trimethyl-2,4-dioxo-1,2,3,4-tetrahydropyrimidin-5-yl]phenyl]propionic acid; VLA-4 Ligand Reagent 14

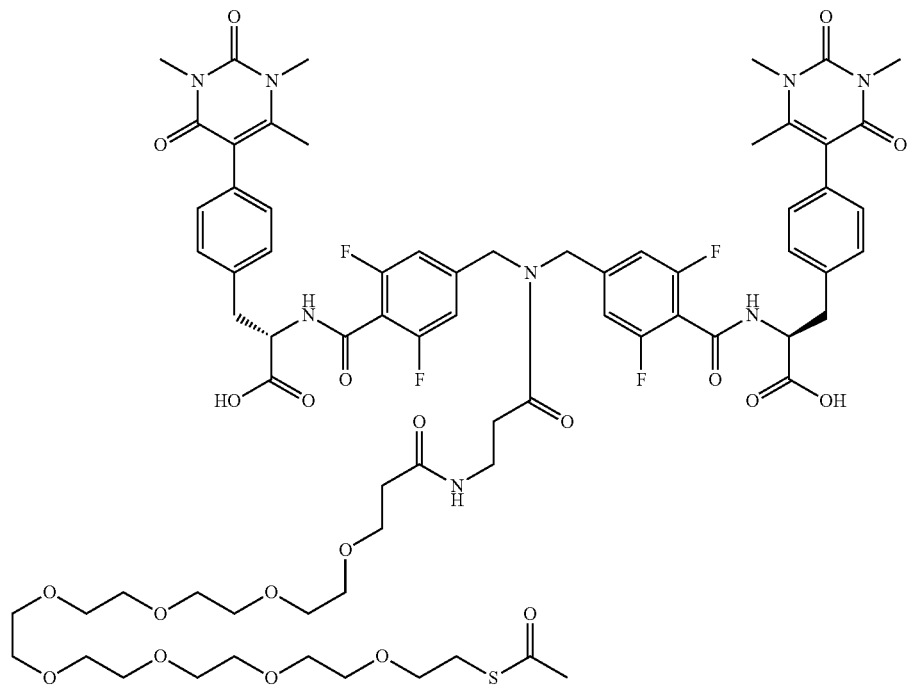 [SMILES: CC(=O)SCCOCCOCCOCCOCCOCCOCCOCCOCCC(=O)NCCC(=O)N(Cc1cc(F)c(C(=O)N[C@@H](Cc2ccc(-c3c(C)n(C)c(=O)n(C)c3=O)cc2)C(=O)O)c(F)c1)Cc1cc(F)c(C(=O)N[C@@H](Cc2ccc(-c3c(C)n(C)c(=O)n(C)c3=O)cc2)C(=O)O)c(F)c1]

Step 1: Preparation of (S)-2-[4-[[3,5-difluoro-4-[(S)-1-propoxycarbonyl-2-[4-[1,3,6-trimethyl-2,4-dioxo-1,2,3,4-tetrahydropyrimidin-5-yl]phenyl]ethylcarbamoyl]benzylamino]methyl]-2,6-difluorobenzoylamino]-3-[4-[1,3,6-trimethyl-2,4-dioxo-1,2,3,4-tetrahydropyrimidin-5-yl]phenyl]propionic acid propyl ester:

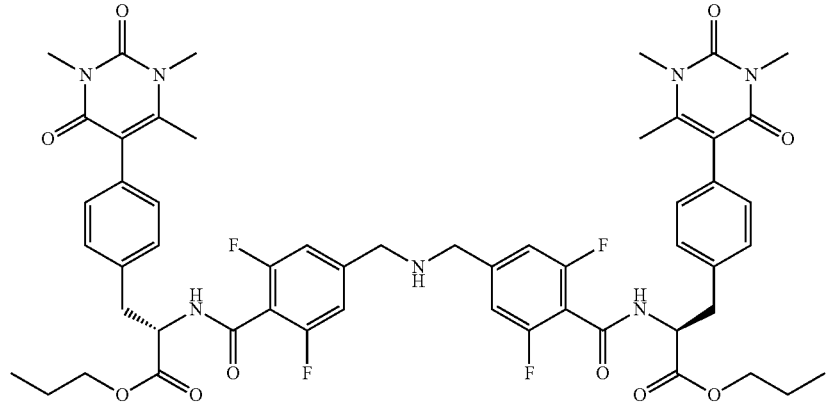 [SMILES: CCCOC(=O)[C@H](Cc1ccc(-c2c(C)n(C)c(=O)n(C)c2=O)cc1)NC(=O)c1c(F)cc(CNCc2cc(F)c(C(=O)N[C@@H](Cc3ccc(-c4c(C)n(C)c(=O)n(C)c4=O)cc3)C(=O)OCCC)c(F)c2)cc1F]

To a 100 mL flask containing (S)-2-(4-cyano-2,6-difluorobenzoylamino)-3-[4-(1,3,6-trimethyl-2,4-dioxo-1,2,3,4-tetrahydro-pyrimidin-5-yl)phenyl]propionic acid propyl ester (524 mg, 1.0 mmol) dissolved in n-propanol (20 mL) purged with nitrogen was added palladium on carbon (10%, 106 mg). The reaction was sealed, degassed with three exposures to nitrogen and house vacuum, and then exposed to a balloon of hydrogen overnight. The reaction was diluted with EA, degassed again, and exposed to hydrogen overnight. The reaction was filtered through celite, concentrated and purified by HPLC yielding the title compound (204 mg, 19%). ES(+)-LRMS m/e calcd. for $C_{54}H_{57}F_4N_7O_{10}$ $(M+H)^+$ 1041, obsd 1041.

Step 2: Preparation of (S)-2-[4-[[3,5-difluoro-4-[(S)-1-carboxy-2-[4-[1,3,6-trimethyl-2,4-dioxo-1,2,3,4-tetrahydro-pyrimidin-5-yl]phenyl]ethylcarbamoyl]benzylamino]methyl]-2,6-difluorobenzoylamino]-3-[4[1,3,6-trimethyl-2,4-dioxo-1,2,3,4-tetrahydropyrimidin-5-yl]phenyl]propionic acid:

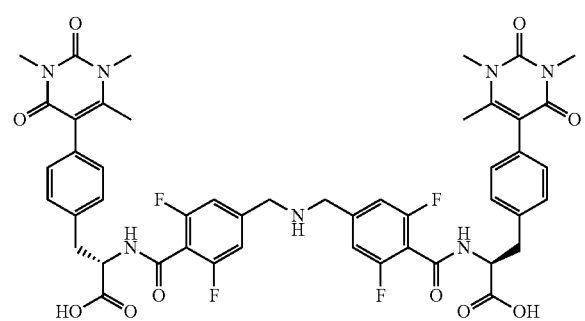

To a 200 mL flask containing (S)-2-[4-[[3,5-difluoro-4-[(S)-1-propoxycarbonyl-2-[4-[1,3,6-trimethyl-2,4-dioxo-1,2,3,4-tetrahydropyrimidin-5-yl]phenyl]ethylcarbamoyl]benzylamino]methyl]-2,6-difluorobenzoylamino]-3-[4-[1,3,6-trimethyl-2,4-dioxo-1,2,3,4-tetrahydropyrimidin-5-yl]phenyl]propionic acid propyl ester (1004 mmg, 0.97 mmol) was added THF (25 mL), water (25 mL) and LiOH (193 mg, 4.6 mmol) and the reaction stirred at room temperature overnight. The reaction was concentrated, dried from acetonitrile yielding a white solid that was mixed with DMSO (13 mL) and water (12 mL). This mixture was heated minimally, filtered and to the filtrate was added TFA (0.25 mL) resulting in a precipitate. The precipitate was diluted with water (50 mL), filtered, washed with water and hexanes and dried on high vacuum yielding the title compound as a white solid (696 mg, 75%). ES(+)-LRMS m/e calcd. for $C_{48}H_{45}F_4N_7O_{10}$ $(M+H)^+$ 956, obsd 956.

Step 3: Preparation of (S)-2-[4-[[3,5-difluoro-4-[(S)-1-methoxycarbonyl-2-[4-[1,3,6-trimethyl-2,4-dioxo-1,2,3,4-tetrahydropyrimidin-5-yl]phenyl]ethylcarbamoyl]benzylamino]methyl]-2,6-difluorobenzoylamino]-3-[4-[1,3,6-trimethyl-2,4-dioxo-1,2,3,4-tetrahydropyrimidin-5-yl]phenyl]propionic acid methyl ester:

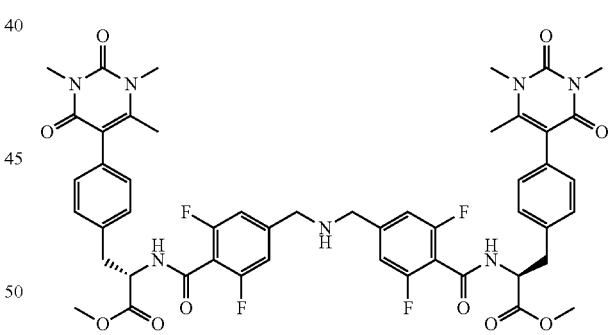

To a flask containing (S)-2-[4-[[3,5-difluoro-4-[(S)-1-carboxy-2-[4-[1,3,6-trimethyl-2,4-dioxo-1,2,3,4-tetrahydropyrimidin-5-yl]phenyl]ethylcarbamoyl]benzylamino]methyl]-2,6-difluorobenzoylamino]-3-[4-[1,3,6-trimethyl-2,4-dioxo-1,2,3,4-tetrahydropyrimidin-5-yl]phenyl]propionic acid (560 mg, 0.59 mmol) was added methanol (50 mL) and TMSCl (398 mg, 460 mL, 3.66 mmol) and the reaction was stirred overnight. Reaction was diluted with EA (10 mL), DCM (140 mL) and was washed with aqueous NaHCO₃ solution (water:saturated solution 50 mL:50 mL, 10 mL brine) and brine (100 mL). The organic layer was dried over MgSO₄, filtered and concentrated yielding the title compound as a white solid and used directly as is. ES(+)-LRMS m/e calcd. for $C_{50}H_{49}F_4N_7O_{10}$ $(M+H)^+$ 984, obsd 984.

Step 4: Preparation of (S)-2-[4-[[3-benzyloxycarbonylaminopropionyl]-3,5-difluoro-4-[(S)-1-methoxycarbonyl-2-[4-[[1,3,6-trimethyl-2,4-dioxo-1,2,3,4-tetrahydro-pyrimidin-5-yl]phenyl]ethylcarbamoyl]benzylamino]methyl]-2,6-difluorobenzoylamino]-3-[4-((1,3,6-trimethyl-2,4-dioxo-1,2,3,4-tetrahydro-pyrimidin-5-yl)phenylpropionic acid methyl ester:

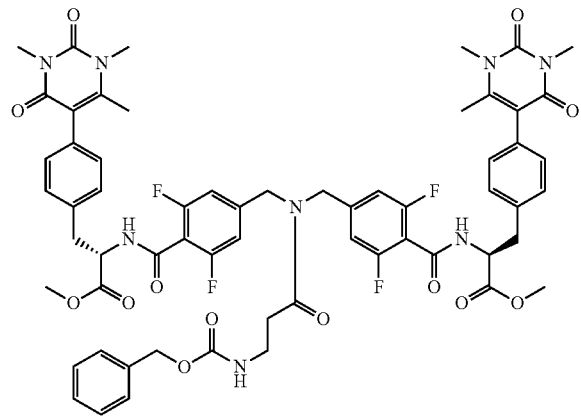

To a flask containing CBZ-beta alanine (123 mg, 0.55 mmol) and DCM (1 mL) was added drop wise oxalyl chloride (710 mg, 0.488 mL, 5.5 mmol) dissolved in DCM (5 mL). The reaction was stirred at room temperature for 2.5 h and then concentrated to a solid. The solid was resuspended in DCM (1 mL) and added drop-to-portion-wise to a solution of (S)-2-[4-[[3,5-difluoro-4-[(S)-1-methoxycarbonyl-2-[4-[1,3,6-trimethyl-2,4-dioxo-1,2,3,4-tetrahydropyrimidin-5-yl]phenyl]ethylcarbamoy]benzylamino]methyl]-2,6-difluorobenzoylamino]-3-[4-[1,3,6-trimethyl-2,4-dioxo-1,2,3,4-tetrahydropyrimidin-5-yl]phenyl]propionic acid methyl ester (0.59 mmol) in DMF (5 mL) and DIPEA (131 mg, 0.178 mL, 1.0 mmol) with additional rinsing of DCM (2×0.4 mL) and the reaction was stirred at room temperature over the weekend. The reaction was diluted with EA (200 mL), washed with aqueous NaHCO$_3$ (water:saturated solution 100 ml:100 mL) and brine (100 mL), dried over MgSO$_4$, filtered, concentrated, and purified by flash chromatography with increasing concentrations of a 10% MeOH/DCM in DCM up to 30%. The title compound was isolated as a white solid (400 mg, 67%). ES(+)-LRMS m/e calcd. for $C_{61}H_{60}F_4N_8O_{13}$ (M+H)$^+$ 1189, obsd 1189.

Step 5: Preparation of (S)-2-[4-[[3-benzyloxycarbonylaminopropionyl]-3,5-difluoro-4-[(S)-1-carboxy-2-[4-[[1,3,6-trimethyl-2,4-dioxo-1,2,3,4-tetrahydro-pyrimidin-5-yl]phenyl]ethylcarbamoyl]benzylamino]methyl]-2,6-difluorobenzoylamino]-3-[4-((1,3,6-trimethyl-2,4-dioxo-1,2,3,4-tetrahydro-pyrimidin-5-yl)phenylpropionic acid:

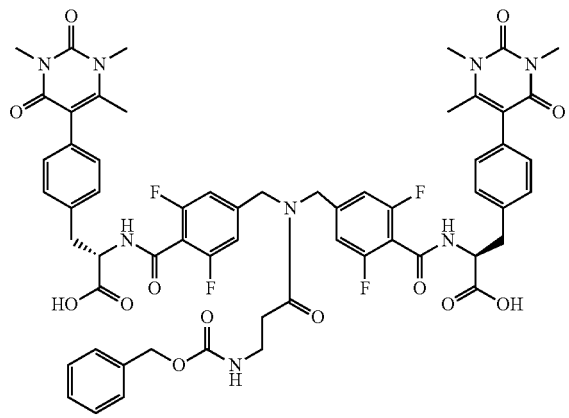

The title compound was prepared using a similar procedure as described in Example 5, Step 7, starting from (S)-2-[4-[[3-benzyloxycarbonylaminopropionyl]-3,5-difluoro-4-[(S)-1-methoxycarbonyl-2-[4-[[1,3,6-trimethyl-2,4-dioxo-1,2,3,4-tetrahydro-pyrimidin-5-yl]phenyl]ethylcarbamoyl]benzylamino]methyl]-2,6-difluorobenzoylamino]-3-[4-(1,3,6-trimethyl-2,4-dioxo-1,2,3,4-tetrahydro-pyrimidin-5-yl)phenylpropionic acid methyl ester (380 mg, 0.32 mmol), THF (8 mL), water (8 mL), LiOH (51 mg, 1.21 mmol), and 1N HCl, and after precipitation, dissolution, and concentration, resulted in a white solid (325 mg). ES(+)-LRMS m/e calcd. for $C_{59}H_{56}F_4N_8O_{13}$ (M+H)$^+$ 1161, obsd 1161.

Step 6: Preparation of (S)-2-[4-[[3-aminopropionyl]-3,5-difluoro-4-[(S)-1-carboxy-2-[4-[[1,3,6-trimethyl-2,4-dioxo-1,2,3,4-tetrahydro-pyrimidin-5-yl]phenyl]ethylcarbamoyl]benzylamino]methyl]-2,6-difluorobenzoylamino]-3-[4-((1,3,6-trimethyl-2,4-dioxo-1,2,3,4-tetrahydro-pyrimidin-5-yl)phenylpropionic acid; VLA-4 Ligand 6:

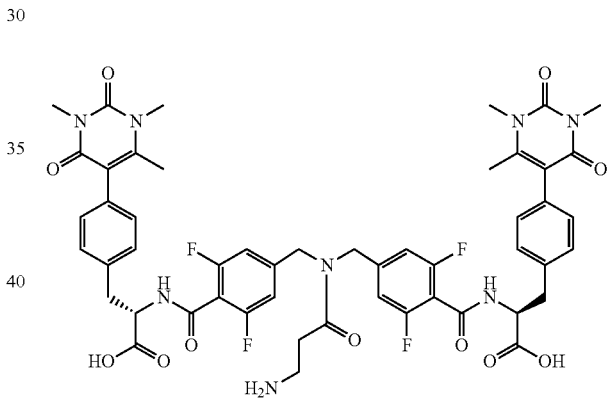

The title compound was prepared using a similar procedure as described in Example 14, Step 1, starting from (S)-2-[4-[[3-benzyloxycarbonylaminopropionyl]-3,5-difluoro-4-[(S)-1-carboxy-2-[4-[[1,3,6-trimethyl-2,4-dioxo-1,2,3,4-tetrahydro-pyrimidin-5-yl]phenyl]ethylcarbamoyl]benzylamino]methyl]-2,6-difluorobenzoylamino]-3-[4-((1,3,6-trimethyl-2,4-dioxo-1,2,3,4-tetrahydro-pyrimidin-5-yl)phenylpropionic acid (313 mg, 0.27 mmol), palladium on carbon (10%), and hydrogen at 1 atmosphere pressure. The title compound was obtained, after four exposures (3×65 mg, 0.061 mmol, room temperature 3 h, 4 h, 18 h; and 205 mg, 0.19 mmol, 40° C. 4.5 h) and filtration, as an off-white solid (79 mg, 28%). ES(+)-LRMS m/e calcd. for $C_{51}H_{50}F_4N_8O_{11}$ (M+H)$^+$ 1027, obsd 1027.

Step 7: Preparation of (S)-2-[4-[[3-[3-[2-[2-[2-[2-[2-[2-[2-(2-acetylsulfanylethaoxy)ethoxy]ethoxy]ethoxy]ethoxy]ethoxy]ethoxy]propionylamino]propionyl]-[4-[(S)-1-carboxy-2-[4-[1,3,6-trimethyl-2,4-dioxo-1,2,3,4-tetrahydropyrimidin-5-yl]phenyl]ethylcarbamoyl]-3,5-difluorobenzylamino]methyl]-2,6-difluorobenzylamino]-3-[4-[1,3,6-trimethyl-2,4-dioxo-1,2,3,4-tetrahydropyrimidin-5-yl]phenyl]propionic acid:
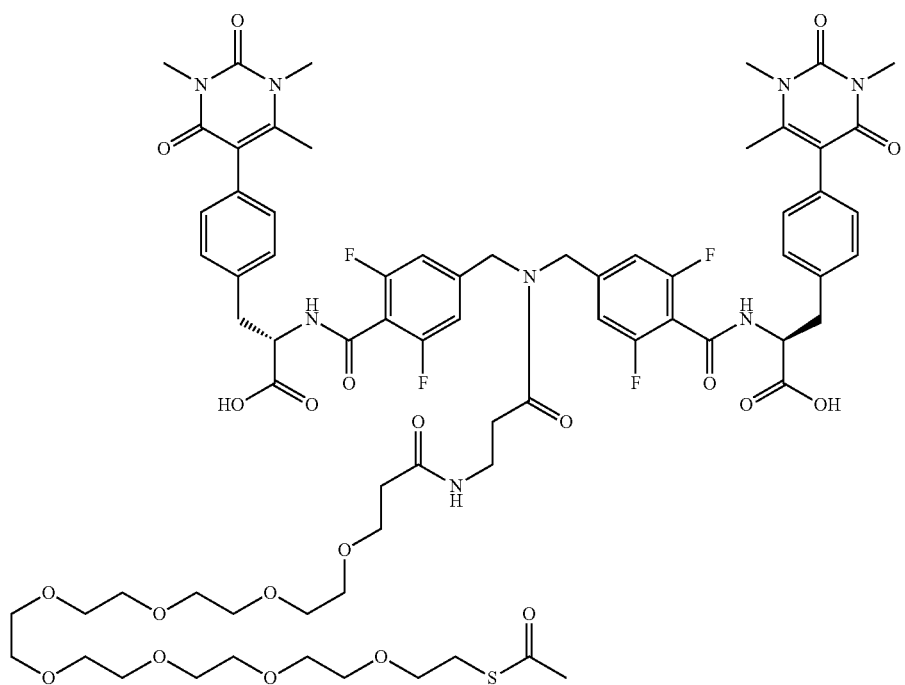 [SMILES: CC(=O)SCCOCCOCCOCCOCCOCCOCCOCCOCCC(=O)NCCC(=O)N(Cc1cc(F)c(C(=O)N[C@@H](Cc2ccc(-c3c(C)n(C)c(=O)n(C)c3=O)cc2)C(=O)O)c(F)c1)Cc1cc(F)c(C(=O)N[C@@H](Cc2ccc(-c3c(C)n(C)c(=O)n(C)c3=O)cc2)C(=O)O)c(F)c1]

The title compound was prepared using a similar procedure as described in Example 1, step 11 starting from (S)-2-[4-[[3-aminopropionyl]-3,5-difluoro-4-[(S)-1-carboxy-2-[4-[[1,3,6-trimethyl-2,4-dioxo-1,2,3,4-tetrahydro-pyrimidin-5-yl]phenyl]ethylcarbamoyl]benzylamino]methyl]-2,6-difluorobenzoylamino]-3-[4-((1,3,6-trimethyl-2,4-dioxo-1,2,3,4-tetrahydro-pyrimidin-5-yl) phenylpropionic acid (84.3 mg, 0.082 mmol), 3-[2-[2-[2-[2-[2-[2-[2-acetylsulfanyl-ethoxy]-ethoxy]ethoxy]ethoxy]ethoxy]ethoxy]ethoxy]propionic acid-2,5-dioxo-pyrrolidin-1-yl ester (49.1 mg, 0.082 mmol), and DIPEA (31 mg, 43 µL, 0.246 mmol) and after HPLC purification, resulted in a white solid (57 mg, 46%). ES(+)-LRMS m/e calcd. for $C_{72}H_{88}F_4N_8O_{21}S_1$ (M/2+H)$^+$ 755, obsd 755.

Preparation of Fluorescein (FITC) Labeled Targeting Reagents

The targeting reagents may be derivatized with fluorophores that may be useful for studying their binding tracking to cells that express receptors to the targeting small molecules. Such molecules may be made in either or both of two methods. First, it is possible to perform the reaction of the targeted maleimides with 2-[(5-fluoroseinyl)aminocarbonyl]ethylmercaptane. Alternatively, the one-pot reaction of the integrin antagonist small molecule targeting ligands, with 2-[(5-fluoroseinyl)aminocarbonyl]ethylmercaptane and the bi-functional PEG reagent which is shown in Schemes 17 and 18.

Example of Method a)

Preparation of (S)-N-[4-[3-[3-[2-[2-[2-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]ethoxy]ethoxy]ethoxy]propionylamino]propoxy]-phenyl]-3-[2-[3-(guanidino)-benzoylamino]-acetylamino]-succinamic acid-FITC

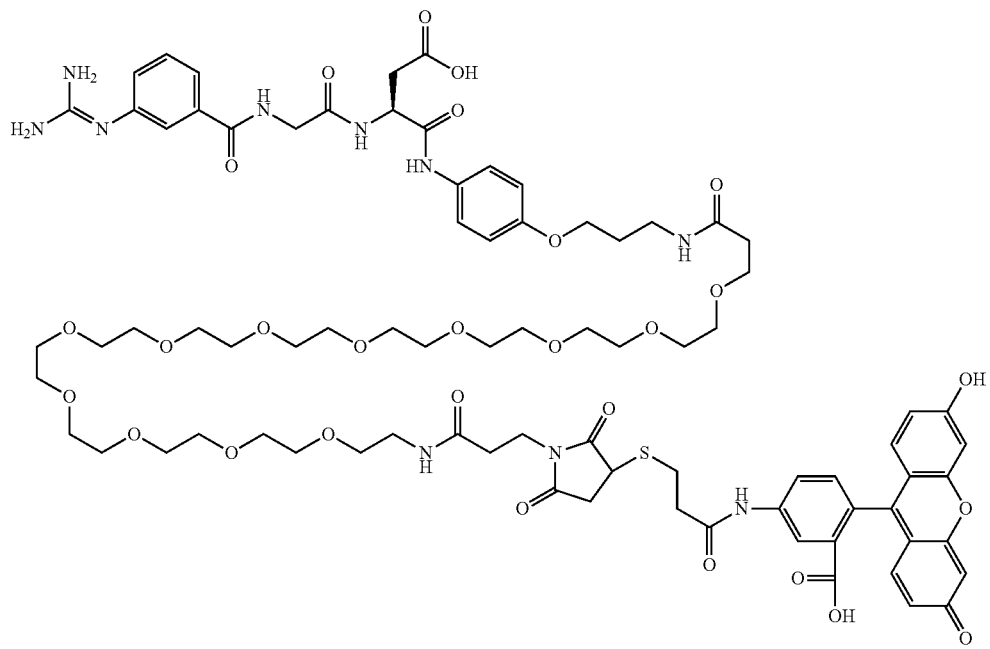 [SMILES: NC(N)=Nc1cccc(C(=O)NCC(=O)N[C@@H](CC(=O)O)C(=O)Nc2ccc(OCCCNC(=O)CCOCCOCCOCCOCCOCCOCCOCCOCCOCCOCCOCCOCCNC(=O)CCN3C(=O)CC(SCCC(=O)Nc4ccc(-c5c6ccc(=O)cc-6oc6cc(O)ccc56)c(C(=O)O)c4)C3=O)cc2)c1]

To an yellow suspension of (S)-N-[4-[3-[3-[2-[2-[2-[2-[2-[2-[2-[2-[2-[2-[2-[2-[3-(2,5-dioxo-2,5-dihydro-pyrrol-1-yl)-propionylamino]ethoxy]ethoxy]ethoxy]ethoxy]ethoxy]ethoxy]ethoxy]ethoxy]ethoxy]ethoxy]ethoxy]-propionylamino]propoxy]-phenyl]-3-[2-[3-(guanidino)-benzoylamino]-acetylamino]-succinamic acid (37.5 mg, 0.03 mmol) and 2-[(5-fluoroseinyl)aminocarbonyl]ethyl-mercaptane (FITC reagent) (15.6 mg, 0.036 mml) in methanol (5 mL) was added an excess of DIPEA (38.7 mg, 52 uL, 0.3 mmol) at room temperature under nitrogen atmosphere. The resulting light yellow suspension was stirred for 2 h at which time LCMS analysis indicated the absence of starting material. Then, the excess DIPEA was removed under vacuum and the desired product was isolated by purification using HPLC to obtain 25 mg (50% yield) of (S)-N-[4-[3-[3-[2-[2-[2-[2-[2-[2-[2-[2-[2-[2-[2-[3-(2,5-dioxo- 2,5-dihydro-pyrrol-1-yl)-propionylamino]ethoxy]ethoxy]ethoxy]ethoxy]ethoxy]ethoxy]ethoxy]ethoxy]ethoxy]ethoxy]ethoxy]-propionylamino]propoxy]-phenyl]-3-[2- [3-(guanidino)-benzoylamino]-acetylamino]-succinamic acid-FITC derivative as a brown solid.

ES(+)-HRMS m/e calcd. for $C_{80}H_{104}N_{10}O_{28}S$ $(M+2H)^{2+}$ 843.3444, obsd. 843.3437.

LCMS data=M+H, 1687.6

Example of Method b)

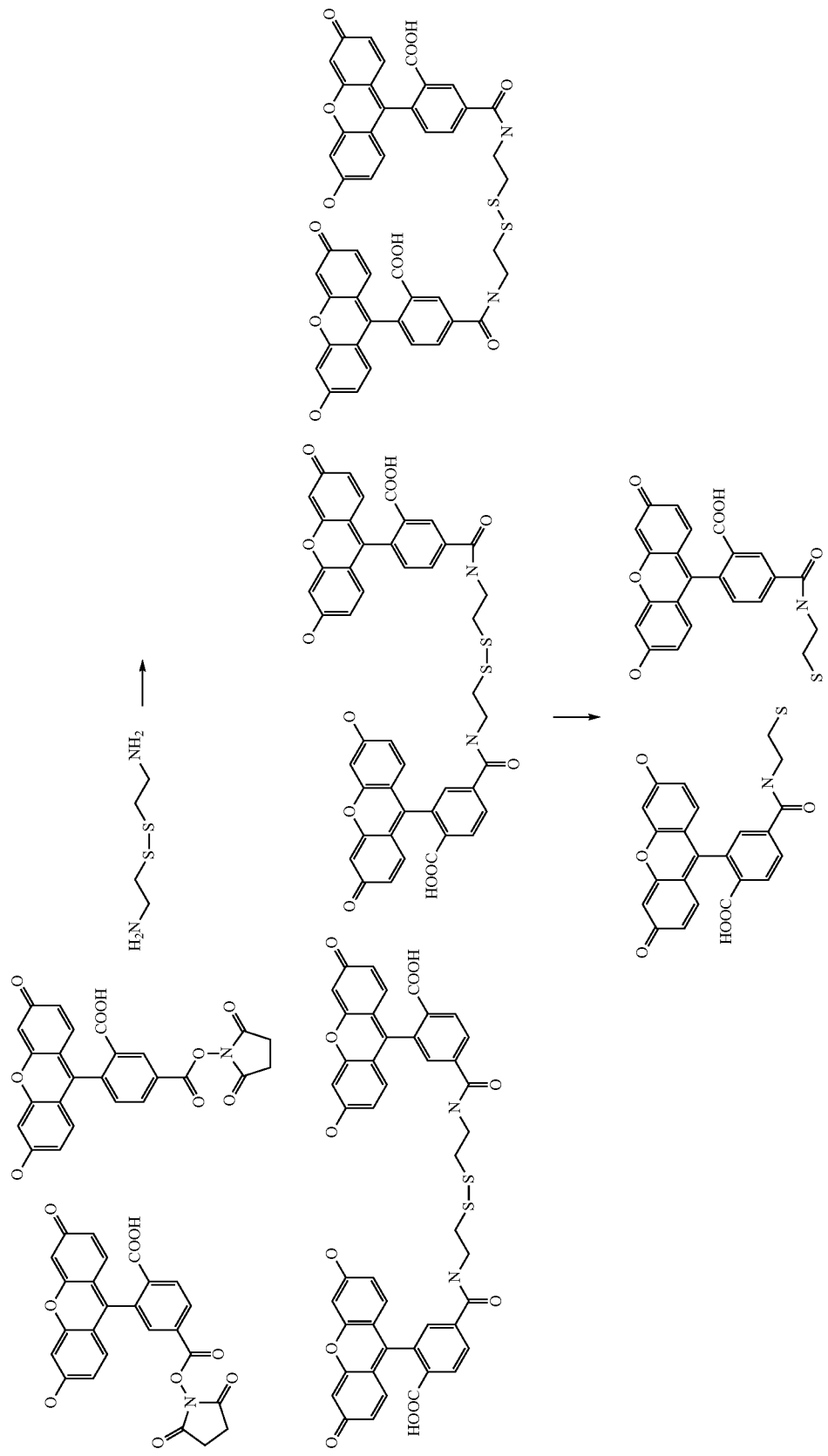

Step 1. Cystamine dihydrochloride (68 mg, 0.301 mmol) and DIEA (110 µL, 2.1 eq.) were dissolved in DMF (10 mL), followed by addition of NHS-fluorescein, a mixture of 5- and 6-carboxyfluorescein (300 mg, 0.634 mmol) and the resulting reaction mixture was stirred overnight at room temperature. Then it was diluted with ethyl acetate and washed three times with water and one time with brine. The extract was dried over anhydrous sodium sulfate, concentrated under reduced pressure, redissolved in small amount of methanol and ethyl acetate, and then triturated with diethyl ether to obtain 140 mg of fluorescein-cystamine adduct as a bright orange solid.

Step 2. The fluorescein-cystamine adduct (80 mg, 0.092 mmol) was dissolved in a 3:1 mixture of methanol and water (4 mL) and TCEP hydrochloride (80 mg, 3 eq.) was added. The resulting reaction mixture was stirred at room temperature for 2 h. The product was purified by HPLC to yield 78 mg of the product. LRMS (ESI) 435.0

Preparation of Fluorescein-Labeled Small Molecule-PEG Conjugates chased from Proligo (Hamburg, Germany). Specifically, the following amidites were used: (5'-O-dimethoxytrityl-N$^6$-(benzoyl)-2'-O-t-butyldimethylsilyl-adenosine-3'-O-(2-cyanoethyl-N,N-diisopropylamino) phosphoramidite, 5'-O-dimethoxytrityl-N$^4$-(acetyl)-2'-O-t-butyldimethylsilyl-cytidine-3'-O-(2-cyanoethyl-N,N-diisopropylamino) phosphoramidite, (5'-O-dimethoxytrityl-N$^2$-(isobutyryl)-2'-O-t-butyldimethylsilyl-guanosine-3'-O-(2-cyanoethyl-N,N-diisopropylamino) phosphoramidite, and 5'-O-dimethoxytrityl-2'-O-t-butyldimethylsilyl-uridine-3'-O-(2-cyanoethyl-N,N-diisopropylamino) phosphoramidite. 2'-O-Methylphosphoramidites carried the same protecting groups as the regular RNA amidites. All amidites were dissolved in anhydrous acetonitrile (100 mM) and molecular sieves (3 Å) were added. To generate the sulfhydryl linker at the 5'-end of the oligomer the 1-O-Dimethoxytrityl-hexyl-disulfide, 1'-[(2-cyanoethyl)-(N,N-diisopropyl)]-phosphoramidite linker from Glen Research (Sterling, Va., USA) was used. Prior to small molecule conjugation the disulfide linker was reduced using Tris-(2-carboxyethyl)phosphine (TCEP, see Scheme 18

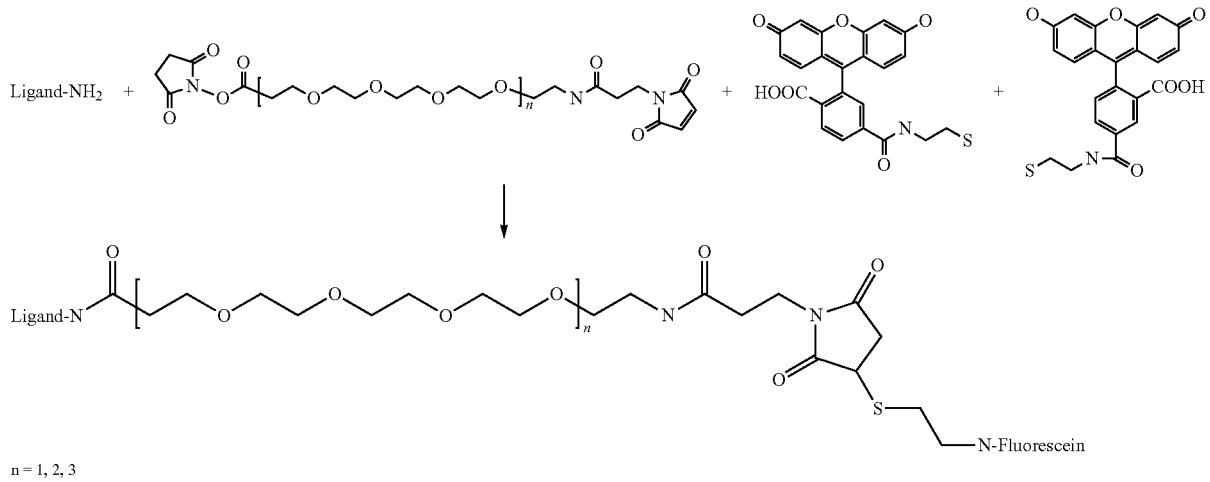

n = 1, 2, 3

General procedure: To a solution of ligand (1 eq.) in DMSO was added DIEA (2 eq.) and SM(PEG)$_{4n}$ (1 eq.). The resulting reaction mixture was stirred at room temperature for 1 h. Next, fluorescein with thiol handle (1 eq.) was added and the reaction mixture was stirred for an additional 10 min. The product was purified by HPLC.

Procedures for Covalent Attachment to Small Molecule Integrin Targeting Ligands to 5'-thiol-siRNA Oligonucleotides siRNA Preparation.
Oligoribonucleotide Synthesis Oligoribonucleotides were synthesized according to the phosphoramidite technology on solid phase employing an ABI 394 synthesizer (Applied Biosystems) at the 10 µmol scale.

siRNA sense strand: SEQ ID NO. 1
siRNA antisense strand: SEQ ID NO.2

The corresponding siRNAs are directed against the house keeping gene AHA1. Syntheses were performed on a solid support made of controlled pore glass (CPG, 520 Å, with a loading of 75 µmol/g, obtained from Prime Synthesis, Aston, Pa., USA). Regular RNA phosphoramidites, 2'-O-Methyl-phosphoramidites as well as ancillary reagents were purbelow). For 5'-end labeling with the Nu547 fluorophore the corresponding phosphoramidite obtained from Thermo Fisher (Milwaukee, Wis.) was employed. 5-Ethyl thiotetrazole (ETT, 500 mM in acetonitrile) was used as activator solution. Coupling times were 6 minutes. In order to introduce phosphorothioate linkages a 100 mM solution of 3-ethoxy-1,2,4-dithiazoline-5-one (EDITH, obtained from Link Technologies, Lanarkshire, Scotland) in anhydrous acetonitrile was employed.

Cleavage and Deprotection of Support Bound Oligomer

After finalization of the solid phase synthesis, the dried solid support was transferred to a 15 mL tube and treated with methylamine in methanol (2M, Aldrich) for 180 min at 45° C. After centrifugation the supernatant was transferred to a new 15 mL tube and the CPG was washed with 1200 µL N-methylpyrolidin-2-one (NMP, Fluka, Buchs, Switzerland). The washing was combined with the methanolic methylamine solution and 450 µL Triethylamine trihydrofluoride (TEA.3HF, Alfa Aesar, Karlsruhe, Germany) was added. This mixture was brought to 65° C. for 150 min. After cooling to room temperature 0.75 mL NMP and 1.5 mL of ethoxytrimethylsilane (Fluka, Buchs, Switzerland) was added. 10 min later, the precipitated oligoribonucleotide was collected by centrifugation, the supernatant was discarded and the solid was reconstituted in 1 mL buffer A (see below).

Purification of Oligoribonucleotides

Crude oligoribonucleotides were purified by strong anion exchange (SAX) HPLC employing a preparative 22×250 mm DNA Pac 100 column (Dionex, Idstein, Germany) on an AKTA Explorer system (GE Healthcare). Buffer A consisted of 10 mM NaClO$_4$, 1 mM EDTA, 10 mM Tris, pH 7.4, 6M Urea and 20% acetonitrile. Buffer B had 500 mM NaClO$_4$ in Buffer A. A flow rate of 4.5 mL/min was employed. UV traces at 260 and 280 nm were recorded. A gradient of 20% B to 45% B within 55 min was employed. Appropriate fractions were pooled and precipitated with 3 M NaOAc, pH=5.2 and 70% Ethanol.

Crude Nu547 labeled oligomers were purified by RP HPLC using a XTerra Prep MS C8 10×50 mm column (Waters, Eschborn, Germany) on an AKTA Explorer system (GE Healthcare). Buffer A was 100 mM triethylammonium acetate (Biosolve, Valkenswaard, The Netherlands) and buffer B contained 50% acetonitrile in buffer A. A flow rate of 5 mL/min was employed. UV traces at 260, 280 and 547 nm (in case of Nu547 labeled oligoribonucleotide) were recorded. A gradient of 5% B to 60% B within 58 column volumes (CV) was employed. Appropriate fractions were pooled and precipitated with 3M NaOAc, pH=5.2 and 70% Ethanol.

Finally, the purified oligomer was desalted by size exclusion chromatography on a column containing Sephadex G-25 (GE Healthcare). The concentration of the solution was determined by absorbance measurement at 260 nm in a UV photometer (Beckman Coulter, Krefeld, Germany). Until annealing the individual strands were stored as frozen solutions at −20° C.

Preparation of Small Molecule RNA Conjugates

Small molecules equipped with a maleimide functionality were covalently conjugated to the RNA through a thioether linkage. To enable this chemistry, ~60 mg of the RNA containing the 5'-disulfide linker was reduced in water (5 mL) to the corresponding thiol using 1 mL TCEP (0.5 M in water, obtained from Sigma Aldrich). Once analytical anion exchange HPLC indicated completion of the reaction (~2 h at room temperature) the RNA was precipitated with 30 mL ethanol/3M NaOAc (pH 5.4) 32:1 (v/v) over night at −20° C. The pellet was collected by centrifugation and used for the subsequent small molecule conjugation.

In a typical conjugation reaction 10 mg RNA was dissolved in 2 mL sodium phosphate buffer (0.1 M, pH 7.0). To this solution the small molecule (0.12 mM) in ACN/NMP 1:1 (v/v) was added over a period of 5 minutes. Once RP LC-ESI MS showed consumption of the input RNA the mixture was diluted with water (~10 mL) and ~40 mL ethanol/3M NaOAc (pH 5.4) 32:1 (v/v) was added to precipitate the conjugated RNA over night at −20° C. The pellet was collected by centrifugation, dissolved in water and if necessary purified by anion exchange HPLC pursuing the procedure given above. If the conjugate is sufficiently pure the reaction mixture was filtered through a size exclusion column (Sephadex G-25, GE Healthcare).

Annealing of Oligoribonucleotides to Generate siRNA

Complementary strands were annealed by combining equimolar RNA solutions. The mixture was lyophilized and reconstituted with an appropriate volume of annealing buffer (100 mM NaCl, 20 mM sodium phosphate, pH 6.8) to achieve the desired concentration. This solution was placed into a water bath at 95° C. which was cooled to rt within 3 h. Table 3: siRNA sequence information; lower case letters:

2'-OMe nucleotide; s: phosphorothioate linkage; dT: deoxythymidine; (C6SSC6): C-6 disulfide linker; (Cy5): cyanine 5 dye.

The following assay was conducted to assess the potency of inhibition of VLA-4-targeted compounds of this invention in a VLA-4/VCAM binding assay in Jurkat cell.

The following adhesion assay has been reported previously and used in this invention with minor modification. See U.S. Pat. Nos. 6,229,011 and 6,380,387 both of which are incorporated herein by reference in their entirety. The functional in vitro potency of the VLA-4 (α4β1) targeting lipids (from the examples) was determined using a Jurkat cell-based assay (below) since Jurkat cells express high levels of VLA-4 on their membrane surface. Each assay was conducted in a 96-well plate with VCAM-1 used as the counter ligand for the cells (i.e., VCAM-1 was bound to the surface of the wells).

More specifically, 96-well high-binding F96 Maxisorp immuno microtiter plates (Nunc) were coated overnight with 25 ng/well of VCAM-1. On the day of the experiment, plates were blocked for 1 hour with PBS buffer containing 1% nonfat dry milk to eliminate nonspecific binding. The plates were then washed with DPBS (Dulbecco's Phosphate Buffered Saline) and blotted dry. Any excess liquid was carefully aspirated from the wells.

As a control, the small molecule antagonist (140) for inhibiting VLA-4 referred to above was added to control wells in buffer containing 4% DMSO and diluted down the plate, typically in a concentration range of 1000 nM to 0.2 nM. Jurkat Clone E6-1 cells (ATCC) were labeled with 100 µg/ml 6-carboxyfluorescein diacetate, a fluorescent dye, and then activated with RPMI 1640 medium containing 0.5 mM of the divalent cation Mn$^{2+}$ and 0.05% bovine serum albumin. It is noted that this activation is needed to achieve maximal binding for the ligand and may simulate the activation of integrins by cytokines and chemokines in vivo. The control compound (27) was determined to have an IC$_{50}$ of about 12 nM (i.e. 50% of the cells did not bind to VCAM-1 on the surface of the wells since the VLA-4 receptors of the cells were presumably bound to or associated with the control compound).

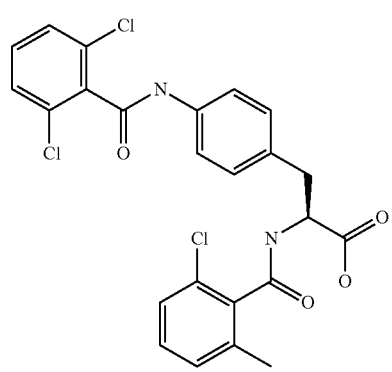

140

To assess VLA-4 inhibition of the VLA-4 targeted compounds of this invention (from the examples), Jurkat cells (expressing high levels of VLA-4) were added to the VCAM-1-coated plates to a final concentration of 2×10$^5$ cells/well in 96-well plates and allowed to incubate with the test compounds (derivatized siRNA, small molecules) for 45 minutes at 37° C. After removing unbound cells by gently washing the wells with PBS, the fluorescence signal from the bound cells was read on a Tecan Safire2 microplate reader at 450 nm. Points were plotted and the $IC_{50}$s of each test compound were determined by regression analysis using the linear portion of the concentration- response curve. These results are shown below in Tables 4 and 5.

Evidence of Cellular Permeability and Localization of Small Molecule Derivatives for Covalently Linked Integrin Antagonists to FITC Fluorophores and siRNA for Targeted Delivery Procedure AML MV4-11 cells in growth medium (RPMI 1640 with 10% FBS) were incubated with Duplex-27 (500 nM) for 1 hour at 37° C. For determining VLA-4 independent binding, 140 (10 μM) was included in one condition to block VLA-4 dependent binding. After incubation, the cells were then washed twice with D-PBS and fixed in 1% paraformaldehyde for 10 minutes. The uptake of siRNA was analyzed by imaging flow cytometry using ImageStreamx (Aminis Corporation, Seattle). The results are shown in Table A and in FIGS. 6-9.

TABLE A

| Compound (concentration) | Mean Cy3 intensity |
|---|---|
| Nothing | 638 |
| 140 (10 μM) | 663 |
| Duplex-27 (500 nM) | 4007 |
| 140 (10 μM) + Duplex-27 (500 nM) | 2273 |

Assay of 5'-Sense Strand Modified siRNA for Knock-Down of AHA1 mRNA in Cellular Systems Materials and Methods Reference gene: GAPDH
Cell line: H1299_Nut-One
Plating density: 5,000 cells/well
Plating format: 96-well
Time from plating to treatment: 0
Control treatment: mock, untreated, control siRNA
Transfection reagent: DharmaFect1
Transfection Method Reverse TF
TF Reagent volume/well 0.15 mL
siRNA final concentration 50 nM
Assay method: Day 1 manual/Day 2 Washer
Reverse transfection: H1299 cells were transfected with indicated siRNA at final concentration of 50 nM using DharmaFect-1 transfection reagent at 0.15 μl/well. Cells were then plated into 96-well plate at 5000 cells/well and incubated at 37° C. for 48 hours.

Figure 10:
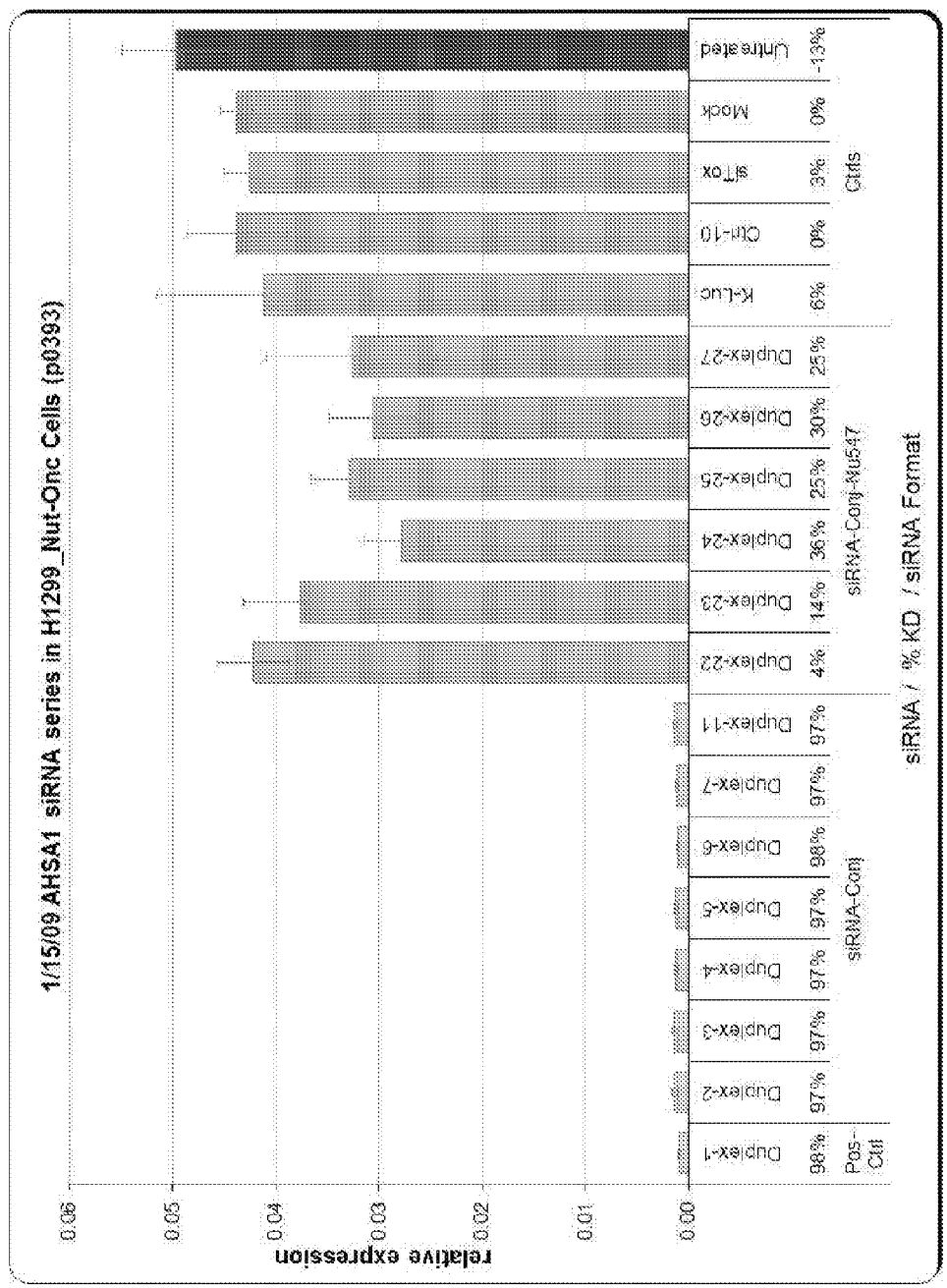
FIG. 10 shows the reduction of AHA1 expression in H1299 cells when treated with siRNA duplexes which have been derivatized on the 5'-sense strand with an integrin targeting small molecule. The y-axis indicates the observed expression level of AHA1. The lower bar indicates a greater degree of knock-down (a higher degree of siRNA transfection); a high bar, a lesser degree of knock-down (i.e., a lesser degree of siRNA transfection). Duplexes in blue have targeting modifications on the 5'-end of the sense strand; those in pink have targeting modifications on the 5'-end of the sense strand as well as Nu547 fluorophore attached to the 5'-end of the antisense strand.
Figure 11:
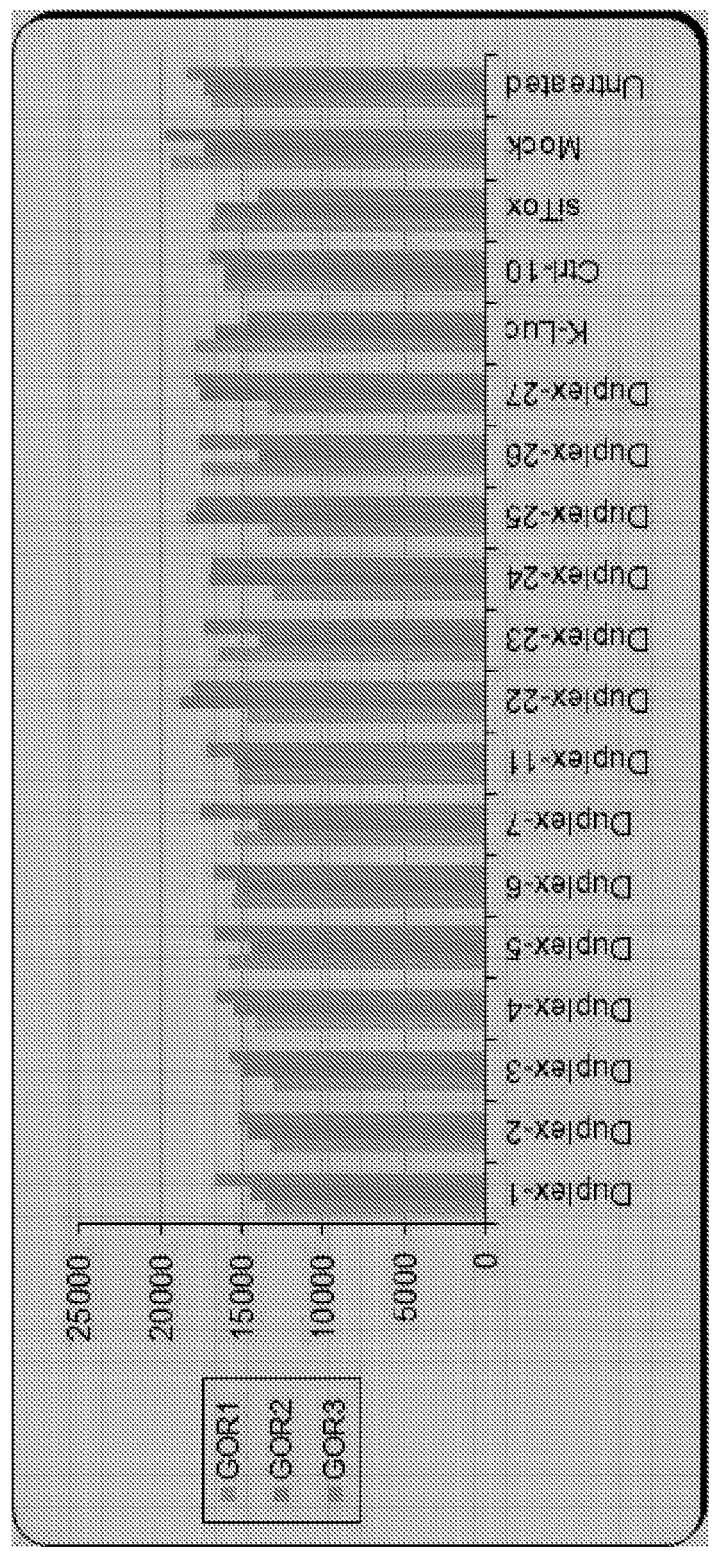
FIG. 11 shows the levels of GAPDH mRNA expression, a marker of cell health. The similarity of the expression levels for those cells treated with derivatized siRNA to that of the mock and untreated cells is an indication of the lack of cellular toxicity at the treatment concentration and duration.

The efficacy of siRNA knock-down was measured with a Branched DNA Assay as reported by the vendor; the results of such knockdown are shown in FIG. 10. The relative cell viability was assessed by the absolute expression of GAPDH in the same well (FIG. 11).

Unless stated to the contrary, all compounds in the examples were prepared and characterized as described. All patents and publications cited herein are hereby incorporated by reference in their entirety.

The invention claimed is:

1. A compound of formula I:

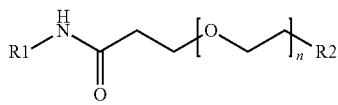

Formula I or a pharmaceutically acceptable salt or ester thereof; wherein n is 1-24 and wherein:

R1 is selected from the group consisting of:

(1) a compound of the formula:

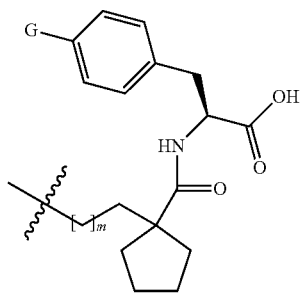

wherein m is 0-3 and G is selected from the group consisting of:

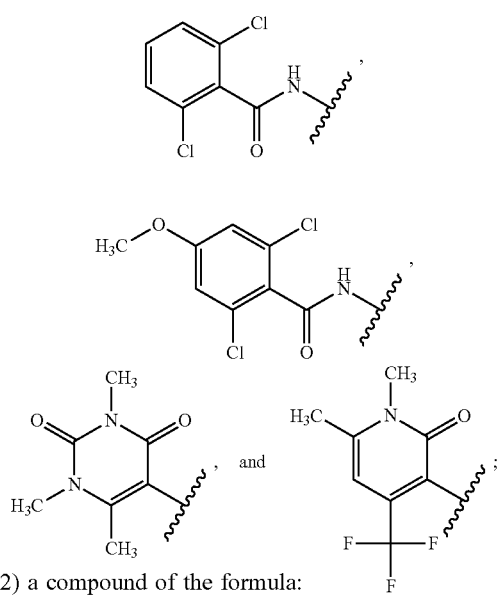

(2) a compound of the formula:

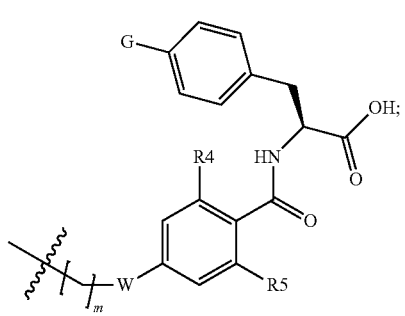

wherein m is 0-3, R4 and R5 are independently hydrogen or halogen, W is O or CH$_2$, and G is selected from the group consisting of:

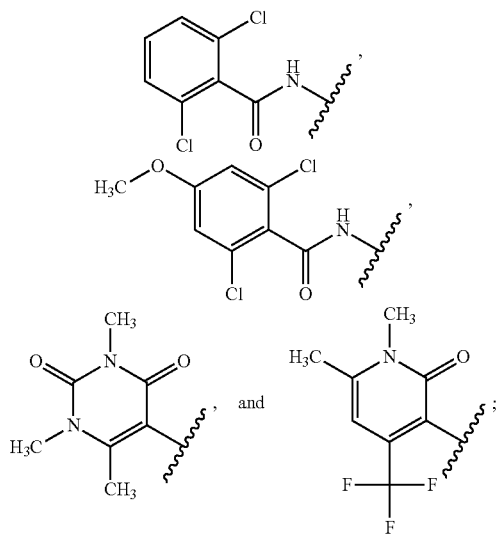

(3) a compound of the formula:

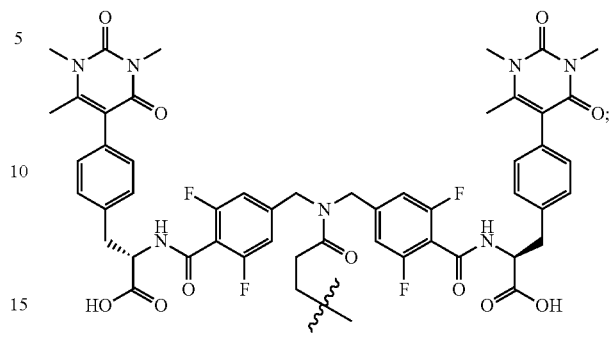

R2 is selected from the group consisting of:

(1) a compound of the formula:

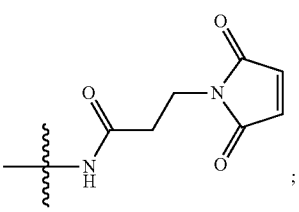 [SMILES: *NC(=O)CCN1C(=O)C=CC1=O]

(2) a compound of the formula:

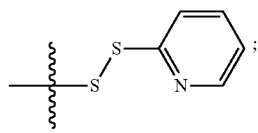

(3) a compound of the formula:

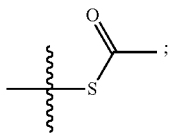 [SMILES: *SC(C)=O]

and (4) a compound of the formula:

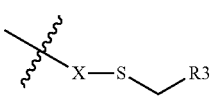

wherein R3 is a conjugated moiety and X represents either sulfur or a compound of the formula:

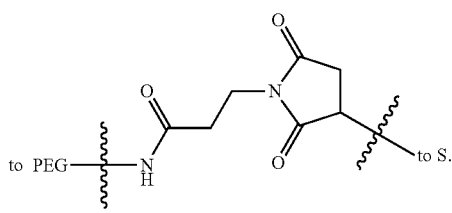

2. A compound according to claim 1, wherein R1 is a compound of the formula:

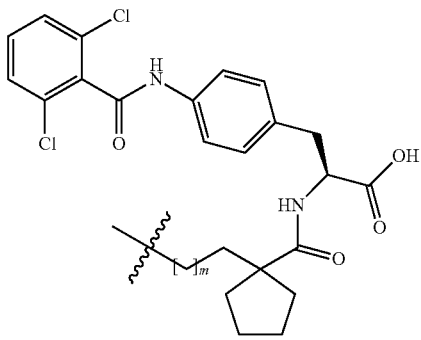

wherein m is 0-3.

3. A compound according to claim 1, wherein R1 is a compound of the formula:

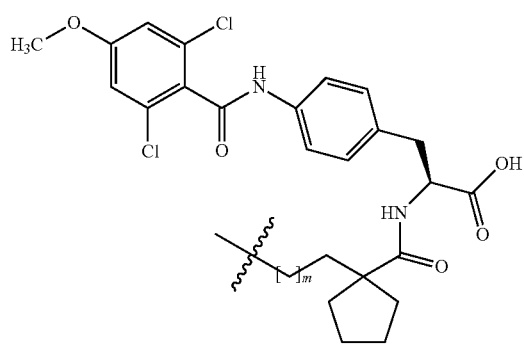

wherein m is 0-3.

4. A compound according to claim 1, wherein R1 is a compound of the formula:

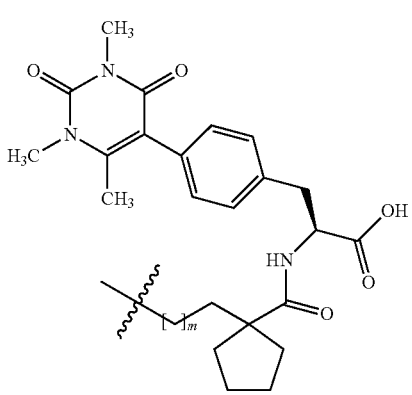

wherein m is 0-3.

5. A compound according to claim 1, wherein R1 is a compound of the formula:

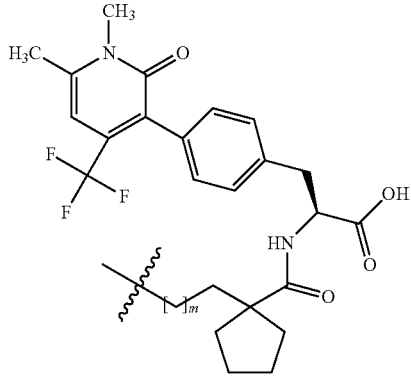

wherein m is 0-3.

6. A compound according to claim 1, wherein R1 is a compound of the formula:

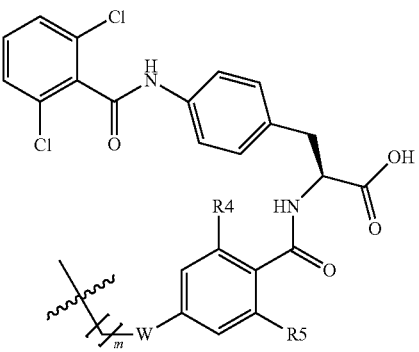

wherein m is 0-3, R4 and R5 are hydrogen or halogen, and W is O or $CH_2$.

7. A compound according to claim 1, wherein R1 is a compound of the formula:

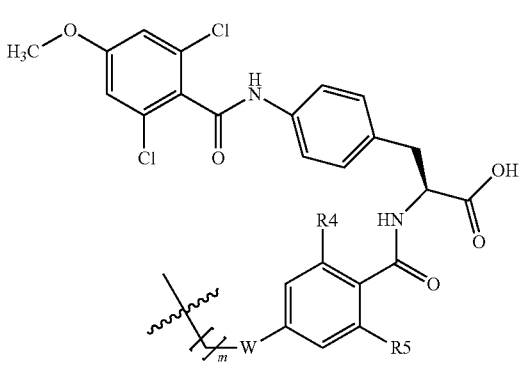

wherein m is 0-3, R4 and R5 are hydrogen or halogen, and W is O or $CH_2$.

8. A compound according to claim 1, wherein R1 is a compound of the formula:

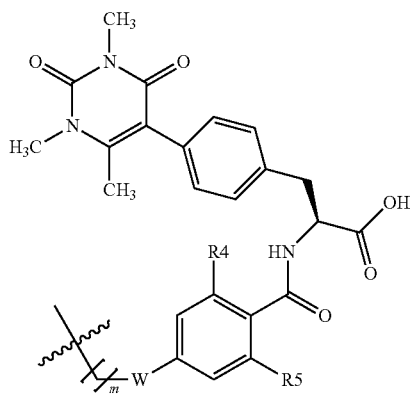

wherein m is 0-3, R4 and R5 are hydrogen or halogen, and W is O or CH$_2$.

9. A compound according to claim 1, wherein R1 is a compound of the formula:

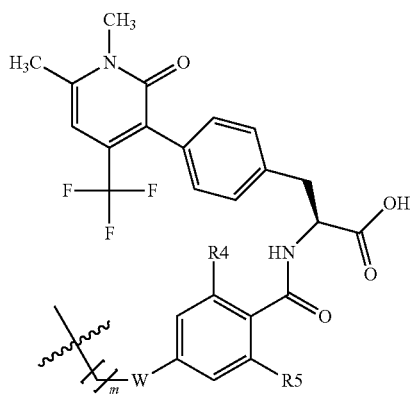

wherein m is 0-3, R4 and R5 are hydrogen or halogen, and W is O or CH$_2$.

10. A compound according to claim 1, wherein R1 is a compound of the formula:

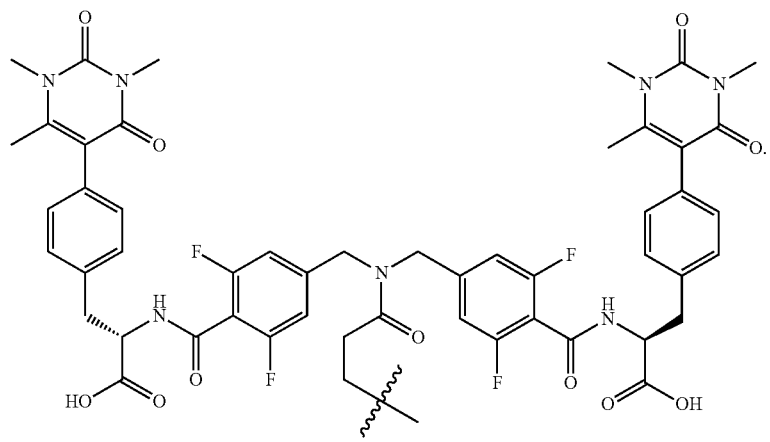 [SMILES: *CCC(=O)N(Cc1cc(F)c(C(=O)N[C@@H](Cc2ccc(-c3c(C)n(C)c(=O)n(C)c3=O)cc2)C(=O)O)c(F)c1)Cc1cc(F)c(C(=O)N[C@@H](Cc2ccc(-c3c(C)n(C)c(=O)n(C)c3=O)cc2)C(=O)O)c(F)c1]

11. A compound according to claim 1, wherein R2 is a compound of the formula:

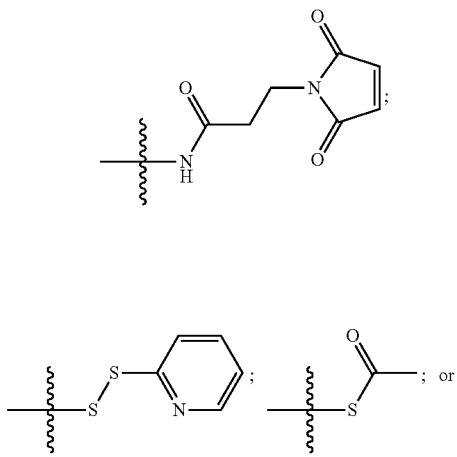

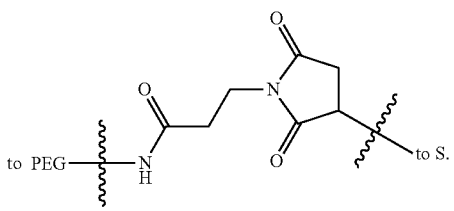

wherein R3 is a single or double stranded oligonucleotide and X represents either sulfur or a compound of the following formula:

12. A compound according to claim 2, wherein R2 is a compound of the formula:

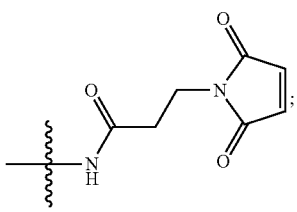

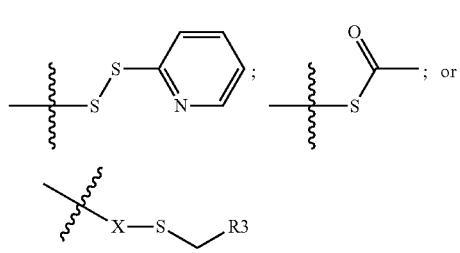

wherein R3 is a single or double stranded oligonucleotide and X represents either sulfur or a compound of the following formula:

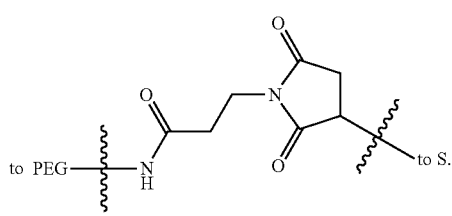

13. A compound according to claims 3, wherein R2 is a compound of the formula:

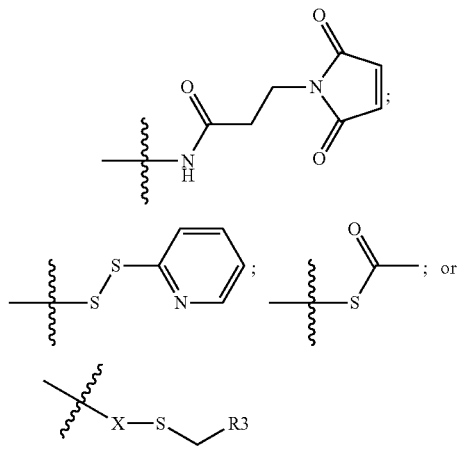

wherein R3 is a single or double stranded oligonucleotide and X represent either sulfur or a compound of the following formula:

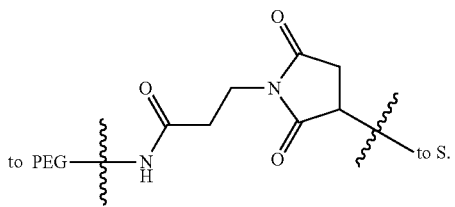

14. A compound according to claim 4, wherein R2 is a compound of the formula:

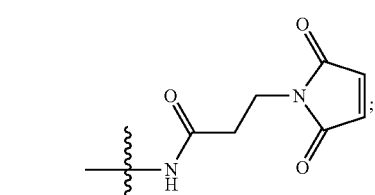

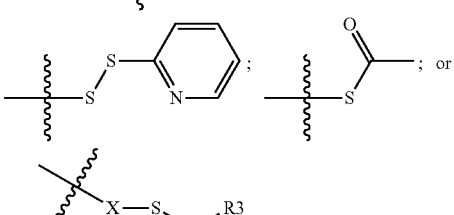

wherein R3 is a single or double stranded oligonucleotide and X represents either sulfur or a compound of the following formula:

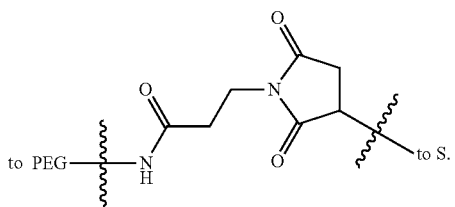

15. A compound according to claim 5, wherein R2 is a compound of the formula:

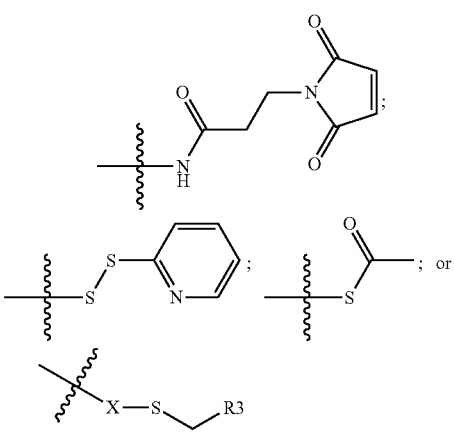

wherein R3 is a single or double stranded oligonucleotide and X represents either sulfur or a compound of the following formula:

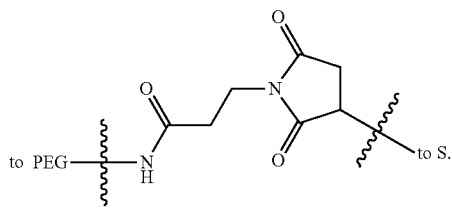

16. A compound according to claim 6, wherein R2 is a compound of the formula:

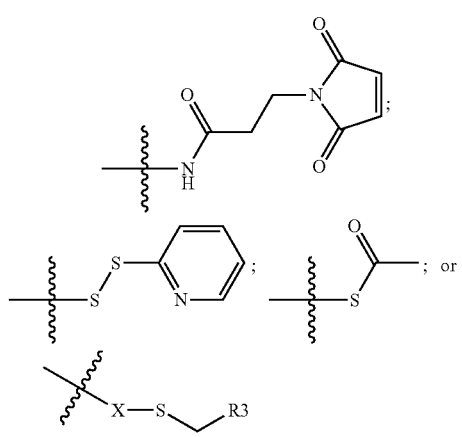

wherein R3 is a single or double stranded oligonucleotide and X represents either sulfur or a compound of the following formula:

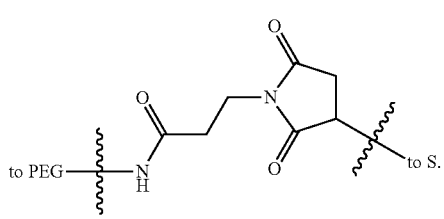

17. A compound according to claim 7, wherein R2 is a compound of the formula:

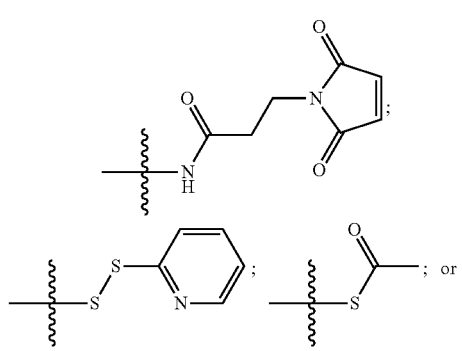

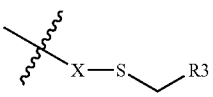

wherein R3 is a single or double stranded oligonucleotide and X represents either sulfur or a compound of the following formula:

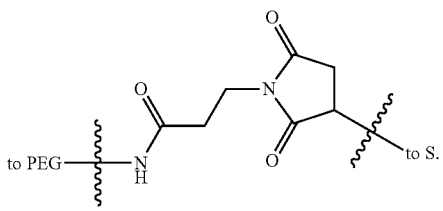

18. A compound according to claim 8, wherein R2 is a compound of the formula:

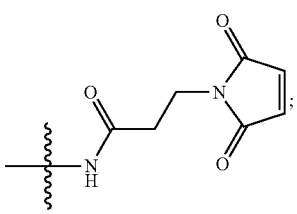

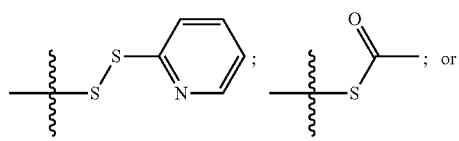

wherein R3 is a single or double stranded oligonucleotide and X represents either sulfur or a compound of the following formula:

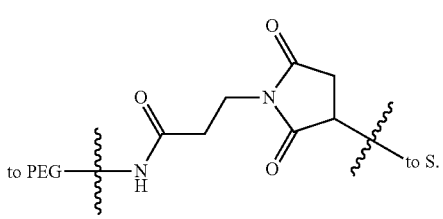

19. A compound according to claim 9, wherein R2 is a compound of the formula:

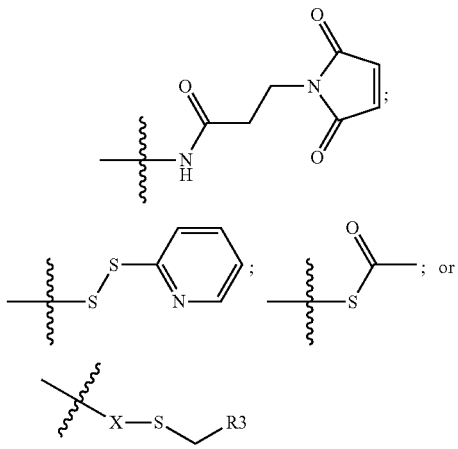

wherein R3 is a single or double stranded oligonucleotide and X represents either sulfur or a compound of the following formula:

20. A compound according to claim 10, wherein R2 is a compound of the formula:

wherein R3 is a single or double stranded oligonucleotide and X represents either sulfur or a compound of the following formula:

21. A compound according to claim 11, wherein R3 is a siRNA molecule.

22. A compound according to claim 1, selected from the group consisting of:
- (S)-3-[4-(2,6-dichlorobenzoylamino)phenyl]-2-[[1-[2-[3-[2-[2-[2-[2-[3-(2,5-dioxo-2,5-dihydropyrrol-1-yl)propionylamino]ethoxy]ethoxy]ethoxy]ethoxy]propionylamino]ethyl]cyclopentanecarbonyl]amino]propionic acid;
- (S)-3-[4-(2,6-dichlorobenzoylamino)phenyl]-2-[[[1 -[2-[3-[2-[2-[2-[2-[2-[2-[3-(2,5-dioxo-2,5-dihydropyrrol-1-yl)propionylamino]-ethoxy]ethoxy]ethoxy]ethoxy]ethoxy]ethoxy]ethoxy]propionylamino]ethyl]cyclopentyl]carbonyl]amino]propionic acid;
- (S)-3-[4-(2,6-dichlorobenzoylamino)phenyl]-2-[[1-[2-[3-[2-[2-[2-[2-[2-[2-[2-[2-[2-[3-(2,5-dioxo-2,5-dihydropyrrol-1-yl)propionylamino]-ethoxy]ethoxy]ethoxy]ethoxy]ethoxy]ethoxy]ethoxy]ethoxy]ethoxy]ethoxy]propionylamino]ethyl]cyclopentanecarbonyl]amino]propionic acid; and
- (S)-2-[[1-[2-[3-[2-[2-[2-[2-[2-[2-[2-(2-acetylsulfanyl-ethoxy)ethoxy]ethoxy]ethoxy]ethoxy]ethoxy]ethoxy]propionylamino]-ethyl]-cyclopentanecarbonyl]-amino]-3-[4-(2,6-dichlorobenzoylamino)phenyl]propionic acid.

23. A compound of claim 1, selected from the group consisting of:
- (S)-3-[4-(2,6-dichlorobenzoylamino)phenyl]-2-[2,6-dichloro-4-[3-[3-[2-[2-[2-[2-[3-(2,5-dioxo-2,5-dihydropyrrol-1-yl)propionylamino]ethoxy]ethoxy]ethoxy]ethoxy]propionylamino]propoxy]benzoylamino]propionic acid;
- (S)-3-[4-(2,6-dichlorobenzoylamino)phenyl]-2-[2,6-dichloro-4-[3-[3-[2-[2-[2-[2-[2-[2-[2-[3-(2,5-dioxo-2,5-dihydropyrrol-1-yl)propionylamino]ethoxy]ethoxy]ethoxy]ethoxy]ethoxy]ethoxy]ethoxy]propionylamino]propoxy]benzoylamino]propionic acid;
- (S)-3-[4-(2,6-dichlorobenzoylamino)phenyl]-2-[2,6-dichloro-4-[3-[3-[2-[2-[2-[2-[2-[2-[2-[2-[2-[2-[3-(2,5-dioxo-2,5-dihydropyrrol-1-yl)propionylamino]ethoxy]ethoxy]ethoxy]ethoxy]ethoxy]ethoxy]ethoxy]ethoxy]ethoxy]ethoxy]ethoxy]propionylamino]propoxy]benzoylamino]propionic acid; and
- (S)-2-[[1-[4-[3-[2-[2-[2-[2-[3-(2,5-dioxo-2,5-dihydropyrrol-1-yl)propionylamino]ethoxy]ethoxy]ethoxy]ethoxy]propionylamino]butyl]cyclopentanecarbonyl]amino]-3-[4-(1,3,6-trimethyl-2,4-dioxo-1,2,3,4-tetrahydropyrimidin-5-yl)phenyl]propionic acid.

24. A compound of claim 1, selected from the group consisting of:
- (S)-2-[2,6-Dichloro-4-[3-[3-[2-[2-[2-[2-[3-(2,5-dioxo-2,5-dihydropyrrol-1-yl)propionylamino]ethoxy]ethoxy]ethoxy]ethoxy]propionylamino]propoxy]benzoylamino]-3-[4-(1,3,6-trimethyl-2,4-dioxo-1,2,3,4-tetrahydropyrimidin-5-yl)phenyl]propionic acid;

(S)-2-[2,6-dichloro-4-[3-[3-[2-[2-[2-[2-[2-[2-[2-[2-[3-(2,5-dioxo-2,5-dihydropyrrol-1-yl)propionylamino]ethoxy]ethoxy]ethoxy]ethoxy]ethoxy]ethoxy]ethoxy]propionylamino]propoxy]benzoylamino]-3-[4-(1,3,6-trimethyl-2,4-dioxo-1,2,3,4-tetrahydropyrimidin-5-yl)phenyl]propionic acid; and (S)-2-[4-[(3-[2-[2-[2-[2-[3-(2,5-Dioxo-2,5-dihydropyrrol-1-yl)propionylamino]ethoxy]ethoxy]ethoxy]propionylamino)methyl]-2,6-difluorobenzoylamino]-3-[4-(1,3,6-trimethyl-2,4-dioxo-1,2,3,4-tetrahydropyrimidin-5-yl)phenyl]propionic acid trifluoracetate salt.

25. A compound of claim 1, selected from the group consisting of:

(S)-2-[4-[(3-[2-[2-[2-[2-[2-[2-[2-[2-[3-(2,5-Dioxo-2,5-dihydropyrrol-1-yl)propionylamino]ethoxy]ethoxy]ethoxy]ethoxy]ethoxy]ethoxy]ethoxy]ethoxy]propionylamino) methyl]-2,6-difluorobenzoylamino]-3-[4-(1,3,6-trimethyl-2,4-dioxo-1,2,3,4-tetrahydropyrimidin-5-yl)phenyl]propionic acid trifluoracetate salt;

(S)-2-[4-[[3-[2-[2-[2-[2-[2-[2-[2-2-acetylsulfanyl-ethoxy]ethoxy]ethoxy]ethoxy]ethoxy]ethoxy]ethoxy]propionylamino]methyl]-2,6-difluorobenzoylamino]-3-[4-(1,3,6-trimethyl-2,4-dioxo-1,2,3,4-tetrahydropyrimidin-5-yl)phenyl]propionic acid; and (S)-2-[4-[[3-[3-[2-[2-[2-[2-[2-∂2-(2-acetylsulfanylethaoxy)ethoxy]ethoxy]ethoxy]ethoxy]ethoxy]ethoxy]ethoxy]propionylamino]propionyl]-[4-[(S)-1-carboxy-2-[4-[1,3,6-trimethyl-2,4-dioxo-1,2,3,4-tetrahydropyrimidin-5-yl]phenyl]ethylcarbamoyl]-3,5-difluorobenzylamino]methyl]-2,6-difluorobenzylamino]-3-[4-[1,3,6-trimethyl-2,4-dioxo-1,2,3,4-tetrahydropyrimidin-5-yl]phenyl]propionic acid.

26. A compound of claim 1, which is: (S)-N-[4-[3-[3-[2-[2-[2-[2-[2-[2-[2-[2-[2-[2-[2-[3-(2,5-dioxo-2,5-dihydropyrrol-1-yl)-propionylamino]ethoxy]ethoxy]ethoxy]ethoxy]ethoxy]ethoxy]ethoxy]ethoxy]ethoxy]ethoxy]propionylamino]propoxy]-phenyl]-3-[2-[3-(guanidino)-benzoylamino]-acetylamino]-succinamic acid-FITC.

27. A pharmaceutical composition comprising a compound according to claim 1 and a pharmaceutically acceptable carrier.

28. A pharmaceutical composition comprising a compound according to claim 2 and a pharmaceutically acceptable carrier.

29. A pharmaceutical composition comprising a compound according to claim 3 and a pharmaceutically acceptable carrier.

30. A pharmaceutical composition comprising a compound according to claim 4 and a pharmaceutically acceptable carrier.

31. A pharmaceutical composition comprising a compound according to claim 5 and a pharmaceutically acceptable carrier.

32. A pharmaceutical composition comprising a compound according to claim 6 and a pharmaceutically acceptable carrier.

33. A pharmaceutical composition comprising a compound according to claim 7 and a pharmaceutically acceptable carrier.

34. A pharmaceutical composition comprising a compound according to claim 8 and a pharmaceutically acceptable carrier.

35. A pharmaceutical composition comprising a compound according to claim 9 and a pharmaceutically acceptable carrier.

36. A pharmaceutical composition comprising a compound according to claim 10 and a pharmaceutically acceptable carrier.

37. A pharmaceutical composition comprising a compound according to claim 11 and a pharmaceutically acceptable carrier.

38. A pharmaceutical composition comprising a compound according to claim 12 and a pharmaceutically acceptable carrier.

39. A pharmaceutical composition comprising a compound according to claim 13 and a pharmaceutically acceptable carrier.

40. A pharmaceutical composition comprising a compound according to claim 14 and a pharmaceutically acceptable carrier.

41. A pharmaceutical composition comprising a compound according to claim 15 and a pharmaceutically acceptable carrier.

42. A pharmaceutical composition comprising a compound according to claim 16 and a pharmaceutically acceptable carrier.

43. A pharmaceutical composition comprising a compound according to claim 17 and a pharmaceutically acceptable carrier.

44. A pharmaceutical composition comprising a compound according to claim 18 and a pharmaceutically acceptable carrier.

45. A pharmaceutical composition comprising a compound according to claim 19 and a pharmaceutically acceptable carrier.

46. A pharmaceutical composition comprising a compound according to claim 20 and a pharmaceutically acceptable carrier.

47. A pharmaceutical composition comprising a compound according to claim 21 and a pharmaceutically acceptable carrier.

48. A pharmaceutical composition comprising a compound according to claim 22 and a pharmaceutically acceptable carrier.

49. A pharmaceutical composition comprising a compound according to claim 23 and a pharmaceutically acceptable carrier.

50. A pharmaceutical composition comprising a compound according to claim 24 and a pharmaceutically acceptable carrier.

51. A pharmaceutical composition comprising a compound according to claim 25 and a pharmaceutically acceptable carrier.

52. A pharmaceutical composition comprising a compound according to claim 26 and a pharmaceutically acceptable carrier.

* * * * *